(12) United States Patent
Sachs et al.

(10) Patent No.: US 10,961,511 B2
(45) Date of Patent: Mar. 30, 2021

(54) CULTURE MEDIUM FOR EXPANDING BREAST EPITHELIAL STEM CELLS

(71) Applicant: Koninklijke Nederlandse Akademie Van Wetenschappen, Utrecht (NL)

(72) Inventors: Lars Norman Sachs, Utrecht (NL); Ana Gracanin, Utrecht (NL); Jarno Drost, Utrecht (NL)

(73) Assignee: Koninklijke Nederlandse Akademie Van Wetenschappen

( * ) Notice: Subject to any disclaimer, the term of this patent is extended or adjusted under 35 U.S.C. 154(b) by 0 days.

(21) Appl. No.: 15/529,150

(22) PCT Filed: Nov. 27, 2015

(86) PCT No.: PCT/EP2015/077988
§ 371 (c)(1),
(2) Date: May 24, 2017

(87) PCT Pub. No.: WO2016/083612
PCT Pub. Date: Jun. 2, 2016

(65) Prior Publication Data
US 2017/0342385 A1 Nov. 30, 2017

(30) Foreign Application Priority Data

Nov. 27, 2014 (GB) .................... 1421094.2

(51) Int. Cl.
*C12N 5/00* (2006.01)
*C12N 5/095* (2010.01)
*C12N 5/071* (2010.01)

(52) U.S. Cl.
CPC ......... *C12N 5/0695* (2013.01); *C12N 5/0631* (2013.01); *C12N 5/00* (2013.01); *C12N 2501/115* (2013.01); *C12N 2501/415* (2013.01)

(58) Field of Classification Search
None
See application file for complete search history.

(56) References Cited

U.S. PATENT DOCUMENTS

| | | | |
|---|---|---|---|
| 5,981,483 A | 11/1999 | Dennis et al. | |
| 6,743,626 B2 | 6/2004 | Baum et al. | |
| 8,642,339 B2 | 2/2014 | Sato et al. | |
| 8,685,726 B2 * | 4/2014 | Schulz | C07K 14/475 435/325 |
| 2003/0003088 A1 | 1/2003 | Tsao et al. | |
| 2003/0129751 A1 | 7/2003 | Grikscheit et al. | |
| 2003/0138951 A1 | 7/2003 | Yin | |
| 2004/0175367 A1 | 9/2004 | Herlyn et al. | |
| 2004/0191902 A1 | 9/2004 | Hambor et al. | |
| 2004/0229355 A1 | 11/2004 | Chen et al. | |
| 2007/0010008 A1 | 1/2007 | Tseng et al. | |
| 2007/0036769 A9 | 2/2007 | Li et al. | |
| 2007/0122903 A1 | 5/2007 | Rezania et al. | |
| 2008/0112890 A1 | 5/2008 | Lelkes et al. | |
| 2008/0113433 A1 | 5/2008 | Robins et al. | |
| 2008/0166327 A1 | 7/2008 | Asahara et al. | |
| 2008/0182328 A1 | 7/2008 | Snyder et al. | |
| 2008/0233088 A1 | 9/2008 | Guha et al. | |
| 2008/0242594 A1 | 10/2008 | McKay et al. | |
| 2009/0275067 A1 | 11/2009 | Taniguchi et al. | |
| 2010/0047853 A1 | 2/2010 | Kuo et al. | |
| 2011/0191868 A1 * | 8/2011 | Gupta | G01N 33/5011 800/8 |
| 2012/0196312 A1 | 8/2012 | Sato et al. | |
| 2012/0207744 A1 | 8/2012 | Mendlein et al. | |
| 2013/0005737 A1 | 1/2013 | Prabhu et al. | |
| 2013/0008956 A1 | 1/2013 | Ashfield | |
| 2013/0052729 A1 | 2/2013 | Pourquie et al. | |
| 2013/0089562 A1 | 4/2013 | French et al. | |
| 2013/0280809 A1 | 10/2013 | Efe et al. | |
| 2014/0243227 A1 * | 8/2014 | Clevers | C12N 5/067 506/9 |
| 2017/0191030 A1 | 7/2017 | Huch Ortega et al. | |
| 2017/0275592 A1 | 9/2017 | Sachs et al. | |
| 2020/0172861 A1 | 6/2020 | Ortega et al. | |

FOREIGN PATENT DOCUMENTS

| | | |
|---|---|---|
| EP | 0953633 A1 | 11/1999 |
| EP | 2412800 A1 | 2/2012 |
| EP | 2772534 A1 | 9/2014 |
| WO | 2004050827 A2 | 6/2004 |
| WO | 2004087896 A3 | 11/2004 |
| WO | 2005040391 A1 | 5/2005 |
| WO | 2005120547 A1 | 12/2005 |
| WO | 2007127454 A3 | 4/2008 |
| WO | 2008046649 A1 | 4/2008 |
| WO | 2008101215 A1 | 8/2008 |
| WO | 2009022907 A2 | 2/2009 |
| WO | 2010011352 A2 | 1/2010 |
| WO | 2010016766 A3 | 5/2010 |

(Continued)

OTHER PUBLICATIONS

Huschtscha et al. Journal of Cell Science; 2009, 122 (16), pp. 2989-2995.*

International Search Report and Written Opinion of International Application No. PCT/EP2015/077988, dated Jan. 21, 2016, (13 pages).

Bottenstein et al., "Growth of a rat neuroblastoma cell line in serum-free supplemented medium," Proc. Natl. Acad. Set USA vol. 76, No. I, pp. 514-517, Jan. 1979.

Brewer et al., "Optimized Survival of Hippocampal Neurons in B27—Supplemented Neurobasal™, a New Serum-free Medium Combination," Journal of Neuroscience Research, vol. 35, p. 567-576 (1993).

Carraway et al, "Neuregulin-2, a new ligand of ErbB3/ErbB4—receptor tyrosine kinases," Nature, vol. 387, May 29, 1997.

(Continued)

*Primary Examiner* — Vera Afremova
(74) *Attorney, Agent, or Firm* — McNeill Baur PLLC

(57) ABSTRACT

The invention relates to improved culture methods for expanding epithelial stem cells and obtaining organoids, to culture media involved in said methods, and to uses of said organoids.

15 Claims, 20 Drawing Sheets

Specification includes a Sequence Listing.

(56) References Cited

FOREIGN PATENT DOCUMENTS

| WO | 201090513 | 8/2010 |
| --- | --- | --- |
| WO | 2010129294 A2 | 11/2010 |
| WO | 2012044992 A2 | 4/2012 |
| WO | 2012014076 A3 | 9/2012 |
| WO | 2012087965 A3 | 10/2012 |
| WO | 2012140274 A2 | 10/2012 |
| WO | 2012168930 A2 | 12/2012 |
| WO | 2012168930 A3 | 4/2013 |
| WO | 2013054112 A1 | 4/2013 |
| WO | 2013061608 A1 | 5/2013 |
| WO | 2013093812 A2 | 6/2013 |
| WO | 2014066649 A1 | 5/2014 |
| WO | 2014124527 A1 | 8/2014 |
| WO | 2014127170 A1 | 8/2014 |
| WO | 2014127219 A1 | 8/2014 |
| WO | 2014145389 | 9/2014 |
| WO | 2014159356 A1 | 10/2014 |
| WO | 2014170411 A1 | 10/2014 |
| WO | 2015173425 | 11/2015 |
| WO | 2016016894 A1 | 2/2016 |
| WO | 2016056999 A1 | 4/2016 |
| WO | 2016083612 A1 | 6/2016 |
| WO | 2016083613 A2 | 6/2016 |
| WO | 2017149025 A1 | 9/2017 |
| WO | 2017220586 A1 | 12/2017 |

OTHER PUBLICATIONS

De Gouville et al., "Inhibition of TGF-β signaling by an ALK5 inhibitor protects rats from dimethylnitrosamine-induced liver fibrosis," British Journal of Pharmacology (2005) 145, p. 166-177.

De Lau et al., "Lgr5 homologues associate with Wnt receptors and mediate R-spondin signalling," Nature, vol. 476, p. 293-298, Aug. 18, 2011.

Dontu et al., "Role of Notch signaling in cell-fate determination of human mammary stem/progenitor cells," Breast Cancer Research, vol. 6, No. 6, p. R605-R615 (2004).

Dorrell et al., "Surface Markers for the Murine Oval Cell Response," Hepatology. Oct. 2008 ; 48(4): p. 1282-1291.

Fuchs, Ota, "Inhibition of TGF-β signaling for the Treatment of Tumo Metastasis and Fibrotic Diseases," Current Signal Transduction Therapy, vol. 6, p. 29-43 (2011).

Hayashi et al., "Establishment and characterization of a parietal endoderm-like cell line derived from Engelbreth-Holm—Swarm tumor (EHSPEL), a possible resource for an engineered basement membrane matrix," Matrix Biology 23(2004) p. 47-62.

Hsieh et al., "Truncated Mammalian Notch1 Activates CBF1/RBPJk—Repressed Genes by a Mechanism Resembling That of Epstein-Barr Virus EBNA2," Molecular and Cellular Biology, Mar. 1996, p. 952-959.

Igaraishi et al,. "Characterization of Recombinant Human Fibroblast Growth Factor (FGF)-10 Reveals Functional Similarities with Keratinocyte Growth Factor (FGF-7)," The Journal of Biological Chemistry vol. 273, No. 21, Issue of May 22, pp. 13230-13235 (1998).

Jeong et al., "Neuregulin-1 induces cancer stem cell characteristics in breast cancer cell lines," Oncology Reports 32: p. 1218-1224 (2014).

Kirikoshi et al., "WNT10a and WNT6, Clustered in Human Chromosome 2q35 Region with Head-to-Tail Manner, Are Strongly Coexpressed in SW480 Cells," Biochemical and Biophysical Research Communications 283, pp. 798-805 (2001).

Lee et al., "Neuregulin Autocrine Signaling Promotes Self-Renewal of Breast Tumor-Initiating Cells by Triggering HER2/HER3 Activation," Cancer Res; 74(1), pp. 341-352 (Jan. 1, 2014).

Macchiarini et al., "Clinical transplantation of a tissue-engineered airway," Lancet 2008; 372:9655, pp. 2023-2030.

Ornitz et al., "Regulation of the Fibroblast Growth Factor Receptor 3 Promoter and Intron I Enhancer by Sp1 Family Transcription Factors," The Journal of Biological Chemistry, vol. 273, No. 9, Issue of Feb. 27, pp. 5349-5357, 1998.

Pasic et al, "Sustained activation of the HER1-ERK1/2—RSK signaling pathway controls myoepithelial cell fate in human mammary tissue," Genes and Development 25:1641-1653 (2011).

Smith and Waterman, "Comparison of Biosequences," Advances in Applied Mathematics 2, pp. 482-489 (1981).

Verbeke et al., "Humanization of the mouse mammary gland by replacement of the luminal layer with genetically engineered preneoplastic human cells," Breast Cancer Research (2014) 16:504, 20 pages.

The WNT Family of Secreted Proteins, R&D Systems Catalog, 2004, 7 pages.

Wouters et al., "Evolution of distinct EGF domains with specific functions," Protein Science (2005), 14:1091-1103.

Yu et al., "Ex vivo culture of circulating breast tumor cells for individualized testing of drug susceptibility," Science, Jul. 11, 2014; 345(6193): 216-220.

Zilberberg et al., "A rapid and sensitive bioassay to measure bone morphogenetic protein activity," BMC Cell Biology 2007,8:41.

International Search Report and Written Opinion for International Application No. PCT/EP2015/077988, dated Apr. 20, 2016 (13 pages).

Afroze et al., "The physiological roles of secretin and its receptor," Ann Transl Med 2013;1(3):29.

Anders and Huber, "Differential expression analysis for sequence count data," Genome Biology 2010, 11:R106.

Cheng et al., "Central and Peripheral Administration of Secretin Inhibits Food Intake in Mice through the Activation of the Melanocortin System," Neuropsychopharmacology (2011) 36, 459-471.

Cuny et al., "Structure-activity relationship study of bone morphogenetic protein (BMP) signaling inhibitors," Bioorg Med Chem Lett. Aug. 1, 2008; 18(15): 4388-4392.

Eden et al., "GOrilla: a tool for discovery and visualization of enriched GO terms in ranked gene lists," BMC Bioinformatics 2009, 10:48.

Egerod et al., A Major Lineage of Enteroendocrine Cells Coexpress CCK, Secretin, GIP, GLP-1, PYY, and Neurotensin but Not Somatostatin Endocrinology, Dec. 2012, 153(12):5782-5795.

Farin et al., "Visualization of a short-range Wnt gradient in the intestinal stem-cell niche," Nature:340 Feb. 18, 2016 (15 pages).

Ghosh et al., "Activity Assay of Epidermal Growth Factor Receptor Tyrosine Kinase Inhibitors in Triple-Negative Breast Cancer Cells Using Peptide-Conjugated Magnetic Beads," Assay and Drug Development Technologies, 11(1):44-51; Jan./Feb. 2011.

Grun et al., "Single-cell messenger RNA sequencing reveals rare intestinal cell types," Nature vol. 525, pp. 251-255 (Sep. 10, 2015).

Gunawardene et al., "Classification and functions of enteroendocrine cells of the lower gastrointestinal tract," Int. J. Exp. Path. (2011), 92, 219-231.

Hashimshony et al., "CEL-Seq: Single-Cell RNA-Seq by Multiplexed Linear Amplification," Cell Reports 2,666-673, Sep. 27, 2012.

Heuberger et al., "Shp2/MAPK signaling controls goblet/paneth cell fate decisions in the intestine," 111: (9);3472-3477 (2014).

Hofer and Drenckhahn, "Cytoskeletal markers allowing discrimination between brush cells and other epithelial cells of the gut including enteroendocrine cells," Cell Biol (1996) 105:405-412.

Howitt et al., "Tuft cells, taste-chemosensory cells, orchestrate parasite type 2 immunity in the gut," Science. Mar. 18, 2016; 351(6279): 1329-1333.

Janssen, and Depoortere, "Nutrient sensing in the gut: new roads to therapeutics? Trends in endocrinology and metabolism," 24, p. 92-100 (2013).

Koo et al., "Stem Cells Marked by the R-Spondin Receptor LGR5," Gastroenterology 2014;147:289-302.

Latorre et al., "Enteroendocrine Cells: A Review of Their Role in Brain-Gut Communication," Neurogastroenterol Motil. May 2016 ; 28(5): 620-630.

Lee et al., "Lung stem cell differentiation in mice directed by endothelial cells via a BMP4-NFATc1-Thrombospondin-1 axis," Cell. Jan. 30, 2014; 156(3): 440-455.

(56) References Cited

OTHER PUBLICATIONS

Manandhar et al., "Glucagon-like Peptide-1 (GLP-1) Analogs: Recent Advances, New Possibilities, and Therapeutic Implications," J. Med. Chem. 2015, 58, 1020-1037.

Munoz et al., "The Lgr5 intestinal stem cell signature: robust expression of proposed quiescent '+4' cell markers," The EMBO Journal (2012) 31,3079-3091.

Nakamura et al., "Anti-patched-1 Antibodies Suppress Hedgehog Signaling Pathway and Pancreatic Cancer Proliferation," Anticancer Research 27: 3743-3748 (2007).

Nakamura et al., "Crosstalk between Wnt and Notch signaling in intestinal epithelial cell fate decision," Journal of Gastroenterology, 2007, vol. 42, No. 9, p. 705.

Nakanishi et al., "Dclk1 distinguishes between tumor and normal stem cells in the intestine," 45:1 p. 98-105 (Jan. 2013).

Pin et al., "Modelling the Spatio-Temporal Cell Dynamics Reveals Novel Insights on Cell Differentiation and Proliferation in the Small Intestinal Crypt," PLoS One, PLoS One 7(5): e37115, 14 pages (May 2012).

Sangiorgi and Capecchi, "Bmi1 is expressed in vivo in intestinal stem cells," Nat Genet. Jul. 2008 ; 40(7): 915-920.

Sato et al., "Paneth cells constitute the niche for Lgr5 stem cells in intestinal crypts," Nature. Jan 20, 2011; 469(7330): 415-418.

Shibue et al., "Fatty acid-binding protein 5 regulates diet-induced obesity via GIP secretion from enteroendocrine K cells in response to fat ingestion," Am J Physiol Endocrinol Metab 308: E583-E591, 2015.

Takeda et al., "Inter-conversion between intestinal stem cell populations in distinct niches," Science. Dec. 9, 2011; 334(6061): 1420-1424.

Terry et al., "Impaired enteroendocrine development in intestinal-specific Islet1 mouse mutants causes impaired glucose homeostasis," Am J Physiol Gastrointest Liver Physiol 307: G979-G991, Sep. 11, 2014.

Tetteh et al., "Replacement of Lost Lgr5-Positive Stem Cells through Plasticity of Their Enterocyte-Lineage Daughters," Cell Stem Cell 18, 203-213, Feb. 4, 2016.

Macchiarini et al. "Clinical transplantation of a tissue-engineered airway," The Lancet, vol. 372, Issue 9655, pp. 2023-2030, 2008.

Van ES et al., "DII1 marks early secretory progenitors in gut crypts that can revert to stem cells upon tissue damage," Nat Cell Biol. Oct. 2012; 14(10): 1099-1104.

Van ES et al., "Notch/γ—Secretase inhibition turns proliferative cells in intestinal crypts and adenomas into goblet cells," vol. 435; 5 pages, Jun. 2005.

Barker et al., "Identification of stem cells in small intestine and colon by marker gene Lgr5," Nature, vol. 449,pp. 1003-1008 (Oct. 25, 2007).

Barker et al., "Lgr5+ve Stem Cells Drive Self-Renewal in the Stomach and Build Long-Lived Gastric Units in Vitro," Cell Stem Cell, vol. 6, pp. 25-36 (Jan. 8, 2010).

Buczacki et al., "Intestinal label-retaining cells are secretory percusors expressing Lgr5," Nature, vol. 495, No. 7493, pp. 65-69, Feb. 27, 2013.

Clotman et al., Control of liver cell fate decision by a gradient of TGFβ signaling modulated by Onecut transcription factors (2005) Genes Dev. 19(16): 1849-54.

Cole et al., "Measuring GSK3 Expression and Activity in Cells," (2008) Methods Mol Biol. 468:45-65.

De Lau et al., "The R-spondin/Lgr5/Rnf43 module: regulator of Wnt signal strength," Genes and Development, 28:305-316 (2014).

Dekkers et al., "A functional CFTR assay using primary cystic fibrosis intestinal organoids," Nature Medicine vol. 19, No. 7 (Jul. 2013); 10 pages.

Eccles, "The epidermal growth factor receptor/Erb-B/HER family in normal and malignant breast biology," International Journal of Developmental Biology, University of the Basque Country Pres., vol. 55, No. 7-9, pp. 685-696 (Jan. 1, 2011).

Farin et al., "Basic and Translational-Alimentary Tract," (2012) Gastroenterology 143:1518-1529.

Gerbal-Chaloin et al., "The WNT/b-Catenin Pathway Is a Transcriptional Regulator of CYP2E1, CYP1A2, and Aryl Hydrocarbon Receptor GeneExpression in Primary Human Hepatocytes," (2014) Molecular Pharmacology 86:624-634.

Hou et al., "Pluripotent Stem Cells Induced from Mouse Somatic Cells by Small-Molecule Compounds," Science Express, 10.1126/science.1239278; 8 pages (Jul. 18, 2013). http://www.sciencemag.org/content/early/recent.

Huch et al., "Urokinase-Type Plasminogen Activator Receptor Transcriptionally Controlled Adenoviruses Eradicate Pancreatic Tumors and Liver Metastasis in Mouse Models," NeoPlasia, vol. 11, No. 6, pp. 518-528 (Jun. 2009).

Hynds et al., "The Relevance of Human Stem Cell-Derived Organoid Models for Epithelial Translational Medicine," Europe PMC Funders Group Stem Cells (Mar. 2013); 11 pages.

International Search Report and Written Opinion for International Application No. PCT/EP2015/060815, dated Jul. 28, 2015 (15 pages).

International Search Report and Written Opinion for International Application No. PCT/EP2015/077990, dated Jul. 6, 2016 (17 pages).

International Search Report and Written Opinion of International Application No. PCT/EP2017/054797, dated May 31, 2017 (9 pages).

International Search Report and Written Opinion of International Application No. PCT/EP2017/065101, dated Oct. 6, 2017 (13 pages).

Kan et al., "MPp53-mediated growth suppression in response to Nutlin-3 in cyclin D1 transformed," Cancer Research (Nov. 2007) 9 pages.

Kogata et al., Neuregulin 3 and Erbb Signalling Networks in Embryonic Mammary Gland Development, J Mammary Gland Biology Neoplasia (2013) 18: pp. 149-154.

Korinek et al., "Activation of ??—Catenin-Tcf Signalling in Colon Cancer by Mutation in ??—Catenin or APC," Science (Apr. 1997), 5 pages.

Robinton et al., "The promise of induced pluripotent stem cells in research and therapy," NIH Public Access Nature 481, (May 13, 2013); 24 pages.

Little et al., "Engineering Biomaterials for Synthetic Neural Stem Cell Microenvironments," (2008) Chem. Rev 108, 1787-1796.

Yin et al: "Niche-dependent high-purity cultures of Lgr5+ intestinal stem cells and their progeny" 2014 Nature Methods 11(1): 106-112.

Namkung et al., "Small-molecule activators of TMEM16A, a calcium-activated chloride channel, stimulate epithelial chloride secretion and instestinal constraction," The FASEB Journal (Nov. 25, 2011) 18 pages.

Oeztuerk-Winder et al., "Regulation of Human Lung Alveolar Multipotent Cells by a Novel p38a MAPK/miR-17-92 axis," The EMBO Journal 31, (2012) pp. 3431-3441.

Saha et al., "Designing synthetic materials to control stem cell phenotype," (2007) Curr Opin Chem Biol. 11(4): 381-387.

Saha et al., "Substrate Modulus Directs Neural Stem Cell Behavior," (2008) Biophysical Journal 95: 4426-4438.

Sato et al. "Single Lgr5 stem cells build crypt villus structures in vitro without a mesenchymal niche," Nature, vol. 459, May 14, 2009, pp. 262-265.

Sato et al., "Long-term Expansion of Epithelial Organoids From Human Colon, Adenoma, Adenocarcinoma, and Barrett's Epithelium," Gastroenterology, vol. 14, pp. 1762-1772 (2011).

Snykers et al., "In Vitro Differentiation of Embryonic and Adult Stem Cells into Hepatocytes: State of the Art," Stem Cells vol. 27, pp. 577-605 (2009).

Spence et al., "Directed differentiation of human pluripotent stem cells into intestinal tissue in vitro," Nature, vol. 470, No. 7332, pp. 105-109 (Feb. 3, 2011).

Stepniak et al., "c-Jun/AP-1 controls liver regeneration by repressing p53/p21 and p38 MAPK activity," (2006) Genes Dev. 20(16):2306-14.

Tisato et al., "Upregulation of SOCS-1 by Nutlin-3 in acute myeloid leukemia cells but not in primary normal cells," Clinics (2014) pp. 68-74.

(56) References Cited

OTHER PUBLICATIONS

Trierweiler et al., "The transcription factor c-JUN/AP-1 promotesHBV-related liver tumorigenesis in mice," Cell Death and Differentiation 23, 576-582 (2016).
Vaughan et al., "Lineage-negative Progenitors Mobilize to Regenerate Lung Epithelium after Major Injury," HHS Public Access Nature (Jan. 29, 2015); 25 pages.
Voronkov et al., "Wnt/beta-Catenin Signaling and Small Molecule Inhibitors," Current Pharmaceutical Design, 19, pp. 634-664, (2013).
Yang et al., Beta-catenin signaling in murine liver zonation and regeneration: A Wnt-Wnt situation! (2014) Hepatology 60(3):964-976.
Yoshimura et al., "Vascular endothelial cells and smooth muscle cells mediate carbachol-induced hepatocyte proliferation via muscarinic receptors and IP3/PKC signaling cascades," Cell Biol Int. Apr. 2009;33(4):516-23.
Zauli et al., "MDM2 Antagonist Nutlin-3 Suppresses the Proliferation and Differentiation of Human Pre-Osteoclasts Through a p53-Dependent Pathway," Journal of Bone and Mineral Research vol. 22, No. 10; (2007) 10 pages.
Zimmerman, "Lung organoid culture," Differentiation; Research in Biological Diversity, vol. 36, No. 1, pp. 86-109 (1987).
Zong et al., "Notch signaling controls liver development by regulating biliary differentiation," Development 136, pp. 1727-1739 (2009).
Zuo et al., "P63 + Krt5 + distal airway stem cells are essential for lung regeneration," Nature (2014) 17 pages.
Abud et al., "Growth of intestinal epithelium in organ culture is dependent on EGF signalling" Experimental Cell Research, Academic Press (303), 2005, pp. 252-262.
Bjerknes et al: "Intestinal epithelial stem cells and progenitors" Methods in Enzymology, Academic Press Inc. (419), Jan. 1, 2006, pp. 337-383.
Booth et al.: "Maintenance of functional stem cells in isolated and cultured adult intestinal epithelium" Experimental Cell Research, Academic Press (249), Jun. 15, 1999, pp. 359-366.
Brockbank et al., "Cryopreservation Guide", https://www.thermofisher.co.nz/Uploads/file/Scientific/Applications/Equipment-Furniture/Cryopreservation-Guide. PDF, 2007, pp. 1-30.
Cambridge Dictionary, definition for "sealed", http://dictionary.cambridge.org/us/dictionary/english/sealed , Sep. 24, 2016, p. 1.
Capaccio et al, "Modern management of obstructive salivary diseases", Acta Otorhinolaryngologica Italica (27), 2007, pp. 161-172.
Crawford et al., "The Notch Response Inhibitor DAPT Enhances Neuronal Differentiation in Embryonic Stem Cell-Derived Embryoid Bodies Independently of Sonic Hedgehog Signaling," Developmental Dynamics (236), 2007, pp. 886-892.
Crosnier et al., "Organizing cell renewal in the intestine: stem cells, signals and combinatorial control", Nature reviews—Genetics (7), May 2006, pp. 349-359.
Dong et al., "The Epithelial—Mesenchymal Transition Promotes Transdifferentiation of Subcutaneously Implanted Hepatic Oval Cells Into Mesenchymal Tumor Tissue," Stem Cells and Development (18)(9), 2009, pp. 1293-1298.
Fuchs, "Inhibition of TGF—Signaling for the Treatment of Tumor Metastasis and Fibrotic Diseases," Current Signal Transduction Therapy, vol. 6, No. 1, Jan. 2011, pp. 29-43(15).
Harada et al., "Rapid formation of hepatic organoid in collagen sponge by rat small hepatocytes and hepatic nonparenchymal cells," Journal of Hepatology (39), (2003) pp. 716-723.
Haramis et al., "De novo crypt formation and juvenile polyposis on BMP inhibition in mouse intestine." Science (303) (5664), Mar. 12, 2004, pp. 1684-1686.
Pasic et al., "Sustained activation of the HER1-ERK1/2-RSK signaling pathways controls myoepithelial cell fate in human mammary tissue." Genes & Development 25:1641-1653 (2011), and Supplementary Material (18 pages).
Supek et al., "REVIGO Summarizes and Visualizes Long Lists of Gene Ontology Terms," PLoS One 6(7):e21800, Jul. 2011, 9 pages.

Kemp et al., "The Roles of Wnt Signaling in Early Mouse Development and Embryonic Stem Cells", Functional Development and Embryology, 2007, pp. 1-13.
Kim et al., "Mitogenic Influence of Human R-Spondin1 on the Intestinal Epithelium" Science (309), Aug. 19, 2005, pp. 1256-1259.
Yoshida et al, "Fine Structural Identification of Organoid Mouse Lung Cells Cultured on a Pigskin Substrate," In Vitro, 1980, vol. 16, No. 11, p. 994-1006.
Lemaigre et al., "Mechanisms of Liver Development: Concepts for Understanding Liver Disorders and Design of Novel Therapies", Gastroenterology (137)(1), Jul. 1, 2009, pp. 62-79.
Malorni et al., "The antioxidant N-acetyl-cysteine protects cultured epithelial cells from menadione-induced cytopathology", Chemico-Biological Interactions (96), 1995, pp. 113-123.
Martin-Belmonte et al., "Cell-Polarity Dynamics Controls the Mechanism of Lumen Formation in Epithelial Morphogenesis", Current Biology (18), 2008, pp. 507-513.
McEwen et al., "Regulation of the Fibroblast Growth Factor Receptor 3 Promoter and Intron I Enhancer by Sp1 Family Transcription Factors," The Journal of Biological Chemistry, vol. 273, No. 9, pp. 5349-5357 (Feb. 27, 1998).
MediLexicon Dictionary, http://www.medilexicon.com/medicaldictionary.php?t=63274 , "Organoid", 2006, p. 1.
Mitaka, Toshihiro, "Reconstruction of hepatic organoid by hepatic stem cells", J. Hepatobiliary Pancreat Sug (9)(6), Jan. 1, 2002, pp. 697-703.
Naftalin et al, "Progesterone stimulation of fluid absorption by the rat uterine gland", Reproduction (123) 2002, pp. 633-638.
Petersen et al, "Interaction with basement membrane serves to rapidly distinguish growth and differentiation pattern of normal and malignant human breast epithelial cells," Proc. Natl. Acad. Sci. (89), Oct. 1992, pp. 9064-9068.
Sarkozi et al., "Oncostatin M is a novel inhibitor of TGF-B1-induced matricellular protein expression," Am J Physiol Renal Physiol (301), 2011, pp. F1014-F1025.
Sato et al.,"Long-term Expansion of Epithelial Organoids From Human Colon, Adenoma, Adenocarcinoma, and Barrett's Epithelium," Gastroenterology, vol. 141, No. 5, Nov. 2011, pp. 1762-1772.
Semler et al., "Mechanochemical Manipulation of hepatocyte Aggregation Can Selectively Induce or Repress Liver-Specific Function", Biotechnology and Bioengineering (69)(4), Sep. 1999, pp. 359-369.
Snykers et al., "Differentiation of neonatal rat epithelial cells from biliary origin into immature hepatic cells by sequential exposure to hepatogenic cytokines and growth factors reflecting liver development", Toxicology in Vitro (21), Apr. 4, 2007, pp. 1325-1331.
Tanimizu et al., "Notch signaling controls hepatoblast differentiation by altering the expression of liver-enriched transcription factors," Journal of Cell Science (117)(15), 2004, pp. 3165-3174.
Tojo et al., "The ALK-5 inhibitor A-83-01 inhibits Smad signaling and epithelial-to-mesenchymal transition bytransforming growth factor-?," Cancer Sci (96)(11), 2005, pp. 791-800.
Tsai et al., "LGR4 and LGR5 Function Redundantly During Human Endoderm Differentiation", Cellular and Molecular Gastroenterology and Hepatology (2), 2016, pp. 648-662.
Vincan et al., "Frizzled-7 dictates three-dimensional organization of colorectal cancer cell carcinoids", Oncogene (26) 2007, pp. 2340-2352.
Williams et al., "The Role of the Wnt Family of Secreted Proteins in Rat Oval Stem" Cell-Based Liver Regeneration Wnt1 Drives Differentiation, American Journal of Pathology (176)(6), Jun. 2010, pp. 2732-2742.
Yang et al., "In vitro trans-differentiation of adult hepatic stem cells into pancreatic endocrine hormoneproducing cells," PNAS (99)(12), Jun. 11, 2002, pp. 8078-8083.
Zaret et al., "Genetic programming of liver and pancreas progenitors: lessons for stem-cell differentiation," Nature Reviews (9), May 2009, pp. 329-340.
Zhu et al., "Chemical Strategies for Stem Cell Biology and Regenerative Medicine", The Annual Review of Biomedical Engineering (13)(1), Apr. 20, 2011, pp. 73-90.

(56) References Cited

OTHER PUBLICATIONS

"Secreted frizzled-related protein 1 also known as SFRP1 is a protein which in humans is encoded by the SFRP1 gene," from http://en.wikipedia.org/wiki/Secreted_frizzled-related)_protein_1 on Oct. 14, 2013, 7 pages.

Morin et al., "Activation of β-Catenin-Tcf-Signaling in Colon Cancer by Mutations in β-Catenin or APC," Science, vol. 275, pp. 1787-1790, Mar. 21, 1997.

Sachs et al., "A Living Biobank of Breast Cancer Organoids Captures Disease Heterogenity," Cell 172, pp. 373-386, Jan. 11, 2018.

Gui et al., "Heregulin protects mesenchymal stem cells from serum deprivation and hypoxia-induced apoptosis," Mol Cell Biochem, 305:171-178 (2007).

* cited by examiner

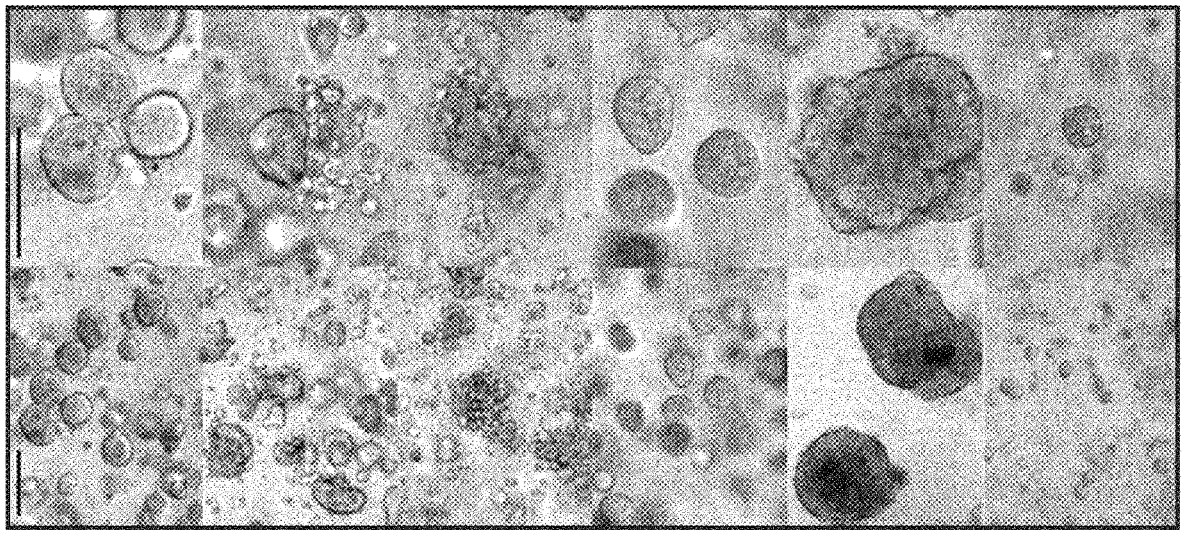
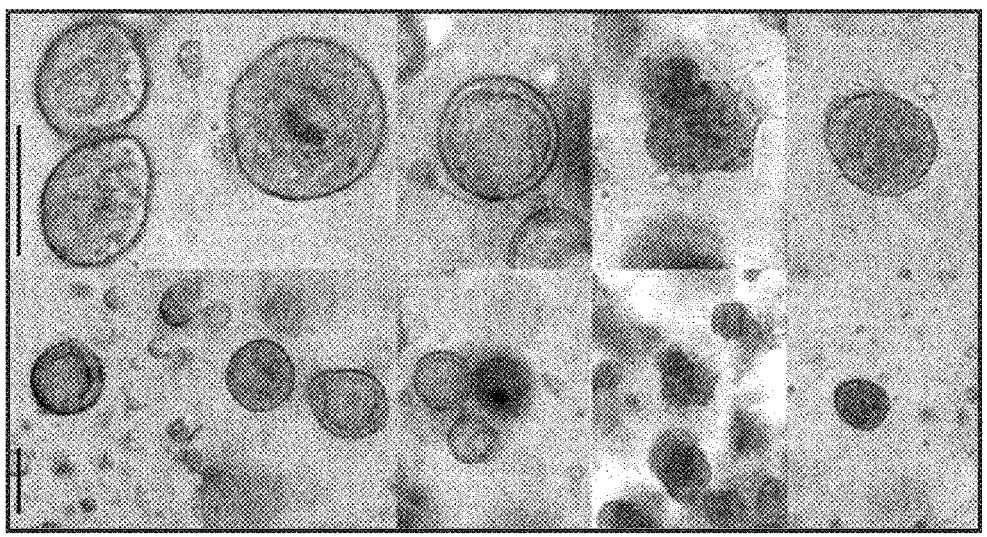
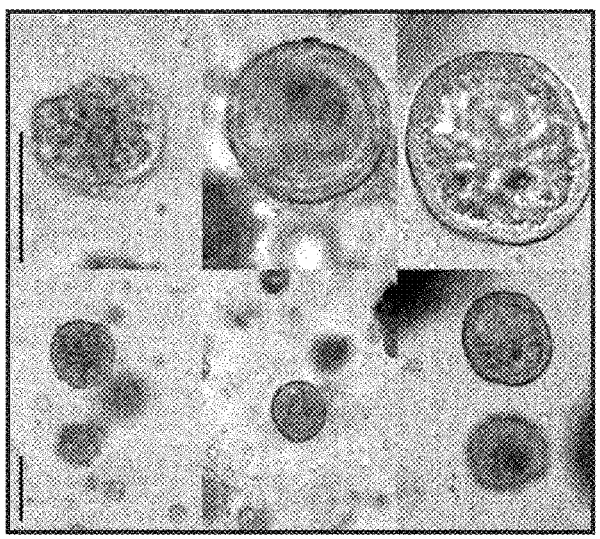
FIG. 2

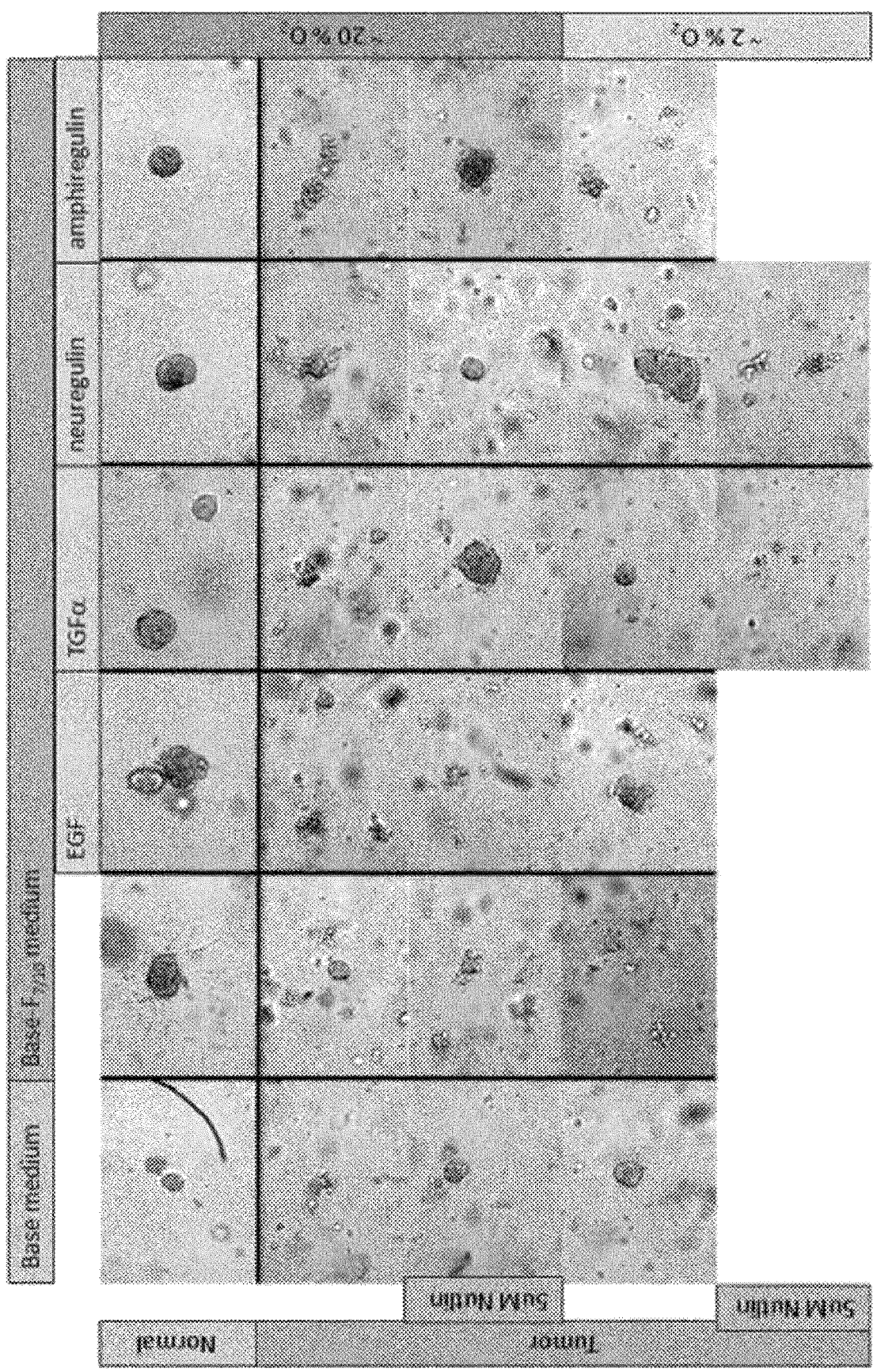
FIG. 3A (contd.)

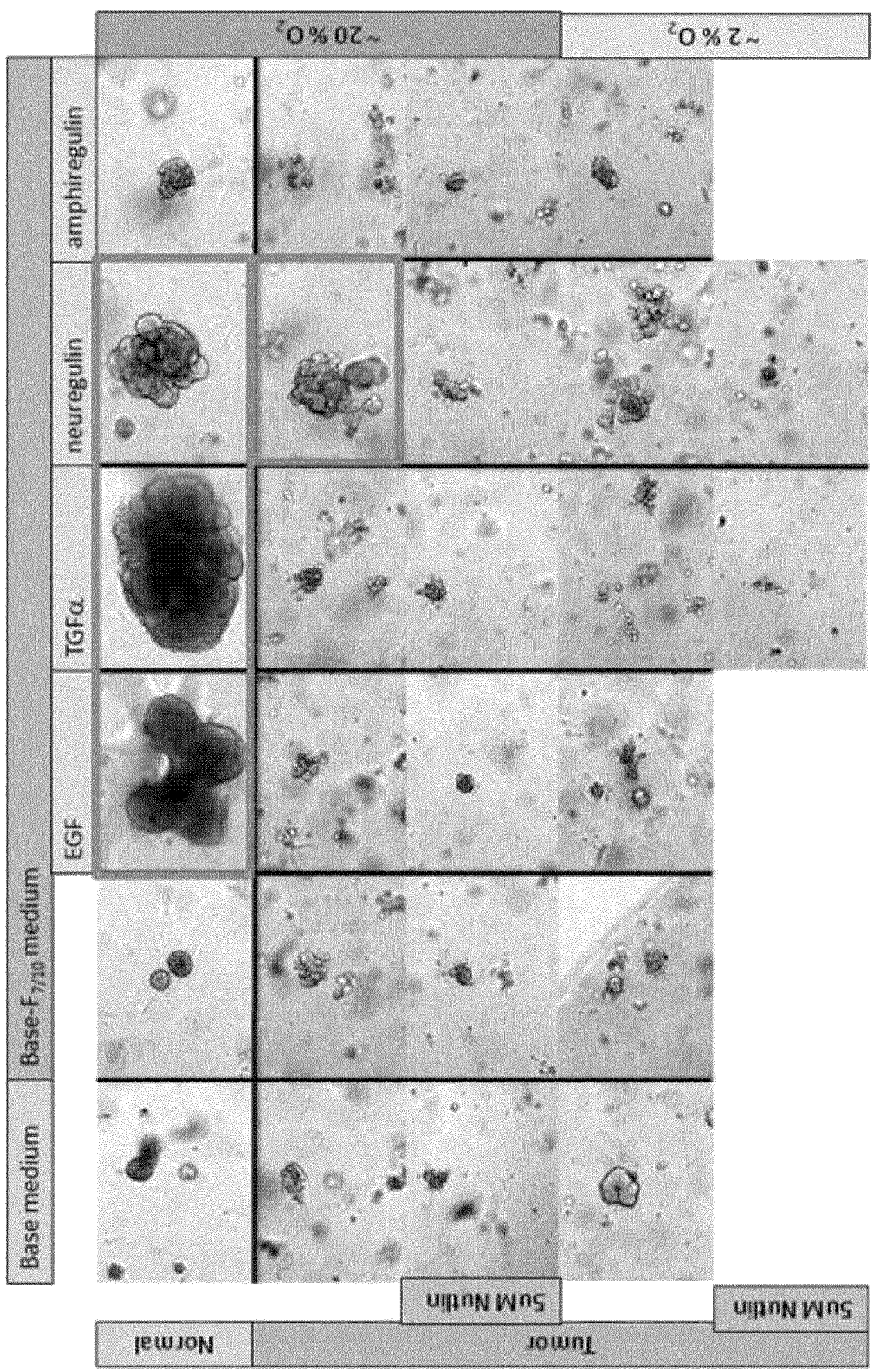
FIG. 3B(contd.)

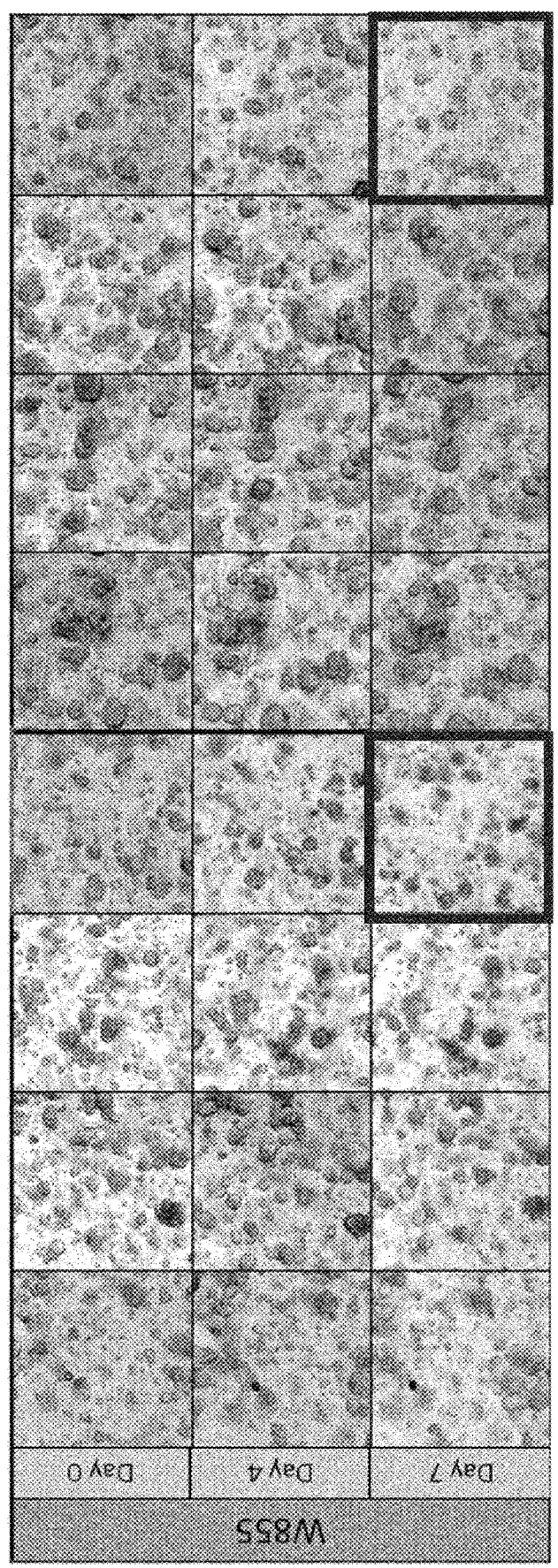
FIG. 8(contd.)

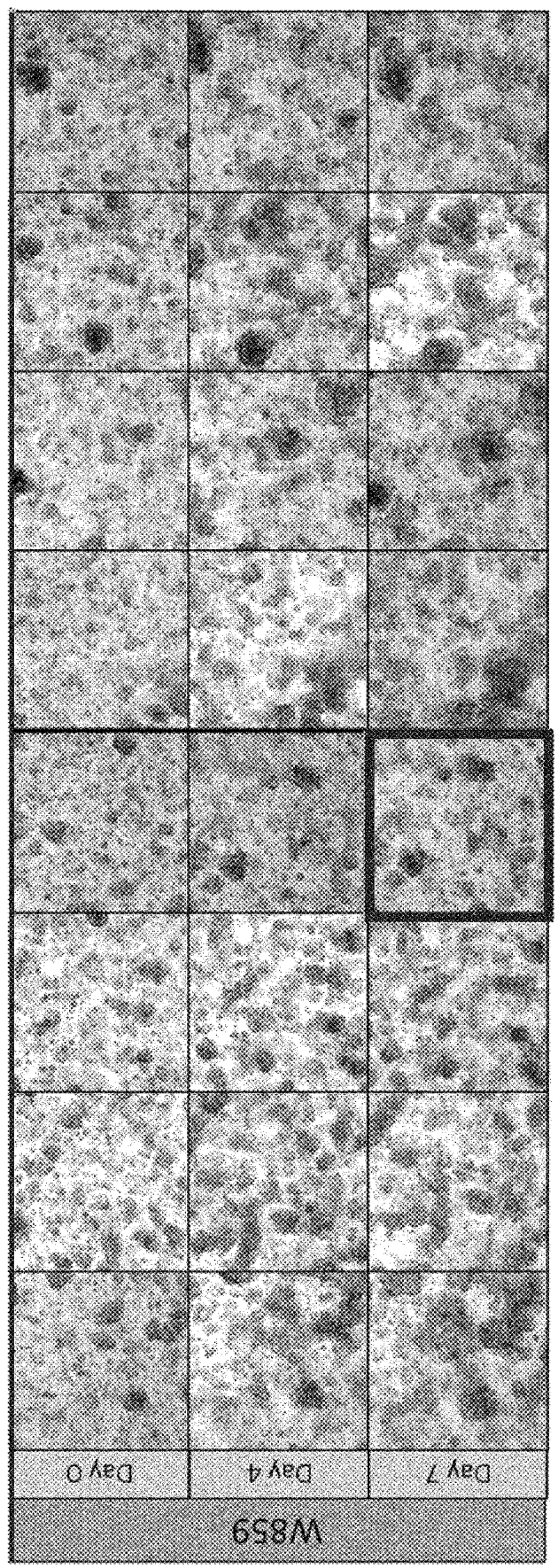
FIG. 8(contd.)

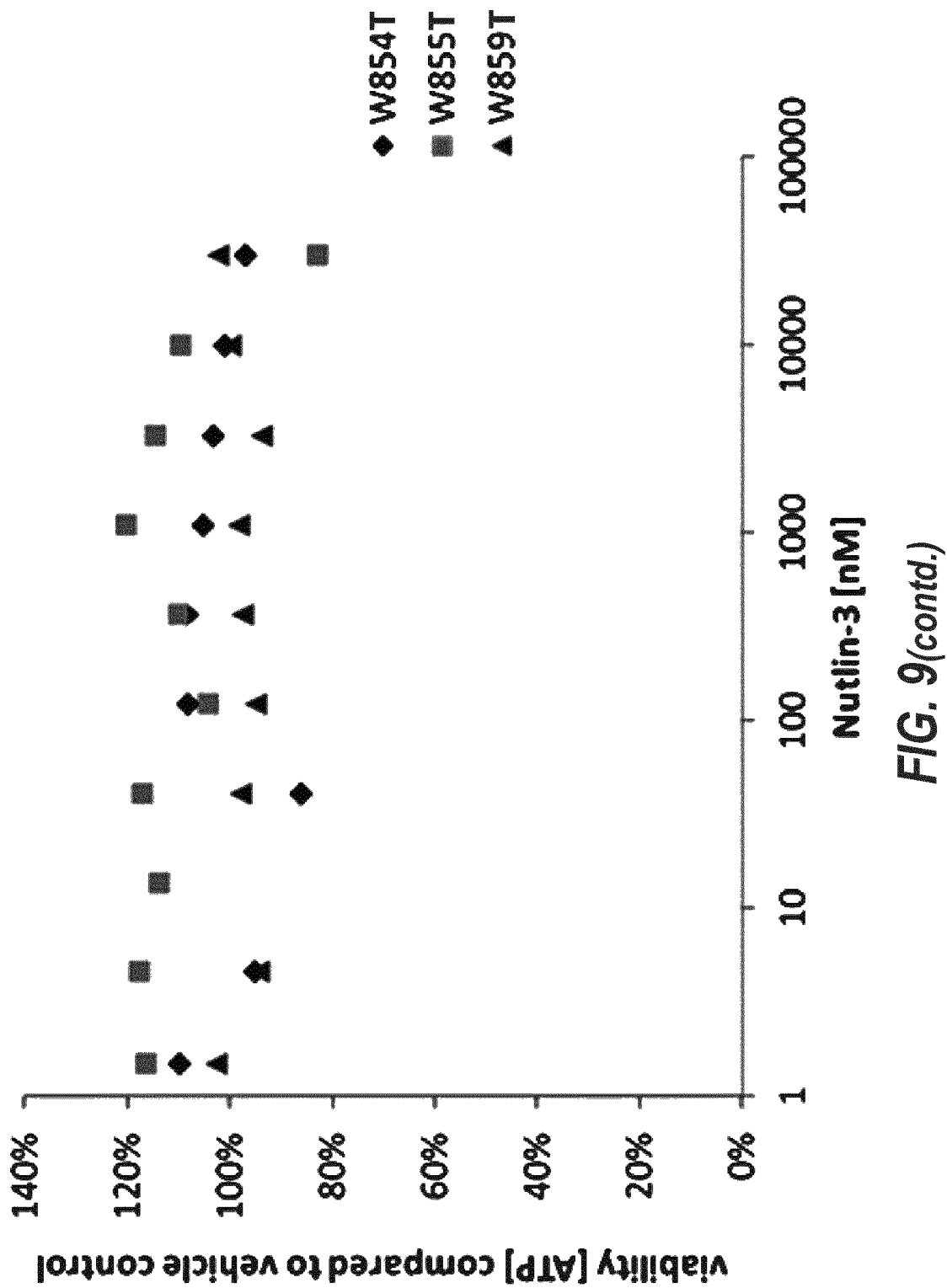
FIG. 9(contd.)

FIG. 13

| Sampling date | Type (N_normal, T_tumor) | ID | P0 P1 P2 P3 P4 P5 P6 P7 P8 P9 P10 P11 | Stage | Histopathology (diff_differentiated, inv_invasive, ca_carcinoma, NST_no special type) | ER | PR | HER2 | culture evaluation |
|---|---|---|---|---|---|---|---|---|---|
| 140128 | T | W854 | expanding | pT2 pN1a LV1 R0, G3 | poorly diff. inv. ca (ductal NST) | negative | negative | positive 3+ | expanding |
| 140203 | N | W855 | expanding | | | positive | positive | negative 0 | promising |
| 140203 | T | W855 | expanding | pT2 pN3a LV1 R1, G2 | mod. diff. inv. ca (ductal NST) | positive | positive | negative 0 | established |
| 140204 | N | W856 | differentiated | | | positive | positive | positive 2+ | terminated |
| 140204 | T | W856 | stopped expanding | pT2 pN0 L0 R0, G2 | mod. diff. inv. ca (ductal NST) | positive | positive | positive 2+ | terminated |
| 140205 | N | W859 | slowly growing | | | negative | negative | negative 1+ | established |
| 140205 | T | W859 | expanding | pT2 pN0 L0 R0, G3 | poorly diff. inv. ca (ductal NST) | negative | negative | negative 1+ | terminated |
| 140210 | N | Z424 | differentiated | | | positive | positive | positive 3+ | promising |
| 140210 | T | Z424 | slowly growing | pT2 pN3a LV1 R0, G2 | mod. diff. inv. ca (ductal NST) | positive | positive | positive 3+ | terminated |
| 140213 | N | W861 | very few | | | positive | positive | negative 0 | |
| 140213 | T | W861 | very few | pT2, pN0 L0 R0, G2 | mod. diff. inv. ca (ductal NST) | positive | positive | negative 0 | |
| 140306 | N | W866 | differentiated | | | negative | negative | negative 1+ | terminated |
| 140306 | T | W866 | differentiated | pT3, pN2a M0, L1 V0 R0, G3 | poorly diff. inv. ca (ductal NST) | negative | negative | negative 1+ | terminated |
| 140429 | N | R1099 | expanding | | | positive | positive | negative 0 | terminated |
| 140429 | T | R1099 | dormant | | | positive | positive | negative 0 | terminated |
| 140506 | N | R1100 | | | | negative | negative | negative | |
| 140506 | T | R1100 | | pT1c, pN0, M0, L1 V0, R0, G3 | poorly diff. inv. ca (ductal NST) | negative | negative | negative | promising |

FIG. 13 (CONTD.)

| Date | N/T | ID | Growth | TNM | Histology | ER | PR | HER2 | Status |
|---|---|---|---|---|---|---|---|---|---|
| 140527 | N | W894 | | | | | | | |
| 140527 | T | W894 | expanding | pT2,pN0,L1,V1,R0,G2 | poorly diff. inv. ca (ductal NST) | positive | negative | negative 1+ | promising |
| 140603 | N | W895 | | | | | | | |
| 140603 | T | W895 | expanding | pT2, pN0, L0, V0, R1, G3 | poorly diff. inv. ca (ductal NST) | positive | positive | negative 0 | promising |
| 140605 | N | W896 | very few | | | | | | |
| 140605 | T | W896 | very few | | | | | | |
| 140610 | N | W899 | 3D | | | | | | |
| 140610 | T | W899 | expanding | pT2, pN2a, L0, V0, R0, G3 | poorly diff. inv. ca (ductal NST) | positive | positive | negative | promising |
| 140610 | N | W900 | few | | | | | | |
| 140610 | T | W900 | expanding | pT3, pN3a, L0, V1, R0, G2 | mod. diff. inv. ca (NST) | positive | positive | negative 1+ | promising |
| 140617 | N | R1117 | 3D | | | | | | |
| 140617 | T | R1117 | slowly growing | ypT3, ypN1a, L1, V1, Rx, G2 | mod. diff. inv. ca | positive | negative | negative | promising |
| 140620 | N | W1003 | 3D | | | | | | |
| 140620 | T | W1003 | slowly growing | pT1c, pN0, cM0, L0, V0, R0, G2 | poorly diff. inv. ca (lobular) | positive | positive | positive 2+ | |
| 140625 | N | W1005 | | | | | | | |
| 140625 | T | W1005 | slowly growing | pT3, pN0, cM0, L0, V0, R0, G2 | mod. diff. inv. ca | positive | positive | negative 0 | |
| 140626 | N | W1007 | 3D | | | | | | |
| 140626 | T | W1007 | expanding | pT2, pN1a, L0, V0, R0, G2 | mod. diff. inv. ca (NST) | positive | positive | negative 1+ | promising |
| 140702 | N | W1009 | 3D | | | | | | |
| 140702 | T | W1009 | expanding | pT2, N1a, L1, V1, R1, G3 | poorly diff. inv. ca (NST) | positive | positive | negative 0 | promising |
| 140707 | N | W1012 | 3D | | | | | | |
| 140707 | T | W1012 | expanding | pT3, pN3a, L1, V1, R1, G2 | mod. diff. inv. ca | positive | positive | negative 0 | promising |

Legend:
- splitting ratio > 1:2
- splitting ratio < 1:2
- splitting ratio > 1:1
- splitting ratio < 1:1
- terminated

FIG. 14

| | order# | company | dissolved in | [stock] | base | base *GF | base **F7/10N | base **F7/10EN | base **F7/10PN |
|---|---|---|---|---|---|---|---|---|---|
| AdDF+++ | | | | | | | | | |
| Rspo1 CM | | home made | AdDF+++ | 100% | 10% | 10% | 10% | 10% | 10% |
| Noggin CM | | home made | AdDF+++ | 100% | 10% | 10% | 10% | 10% | 10% |
| Wnt3a CM | | home made | D10F | 100% | | 50% * | | | |
| control CM | | home made | D10F | 100% | | 50% | | | |
| B27 supplement | 17504-44 | Gibco/Invitrogen | | | 1x | 1x | 1x | 1x | 1x |
| N-Acetylcysteine | A9165-5g | Sigma | H2O | 500mM | 1.25mM | 1.25mM | 1.25mM | 1.25mM | 1.25mM |
| Nicotinamide | N0636 | Sigma | PBS | 1M | 10mM | 10mM | 10mM | 10mM | 10mM |
| Y-27632 (ROCK 1, 2 inhibitor) | Y-27632 | Abmole | H2O | 10mM | 5uM | 5uM | 5uM | 5uM | 5uM |
| A83-01 (ALK 4, 5, 7 inhibitor) | 2939 | Tocris | DMSO | 500uM | 500nM | 500nM | 500nM | 500nM | 500nM |
| SB 202190 (p38 MAP kinase inhibitor) | S7067 | Sigma | DMSO | 30mM | 1uM | 1uM | 1uM | 1uM | 1uM |
| human EGF | AF-100-15 | Peprotech | 0.1% BSA/PBS | 500ug/ml | * | 1-50ng/ml | | | |
| human FGF-7 | 100-19 | Peprotech | 0.1% BSA/PBS | 50ug/ml | * | 5-25ng/ml | 5ng/ml | 5ng/ml | 5ng/ml |
| FGF-10 | 100-26 | Peprotech | 0.1% BSA/PBS | 100ug/ml | | 20-100ng/ml | 20ng/ml | 20ng/ml | 20ng/ml |
| human amphiregulin | 262-AR | R&D systems | 0.1% BSA/PBS | 10uM | * | 5nM | 5nM | 5nM | |
| human heregulin β-1 (=neuregulin) | 100-03 | Peprotech | 0.1% BSA/PBS | 10uM | | 5nM | | | |
| human TGF-alpha | A167-v7 | R&D systems | 0.1% BSA/PBS | 50ug/ml | * | 50ng/ml | | | |
| human PDGF-CC | 100-00CC | Peprotech | 0.1% BSA/PBS | 20ug/ml | | 20ng/ml | | | 20ng/ml |
| Nutlin-3 | 10004372 | Cayman Chem. | Ethanol | 5mM | | 5uM | 5uM | 5uM | 5uM |

\* growth factors added alone or in combination during optimization
\*\* growth factors added to currently used culture media AdDF+++
500ml   Advanced DMEM/F12 [Invitrogen #12634-034]
+5ml    GlutaMax 100 x [Invitrogen # 35050-068]
+5ml    Hepes 1 M [Invitrogen # 15630-056]
+5ml    Penicillin/Streptomycin 10K U/ml 10K µg/ml 100x [Invitrogen #15140-122]
+500ul  Primocin [Invivogen # ant-pm-1]

D10F
DMEM 31966 Life Technologies 500 ml
+ 60 ml FBS Sigma F7524
+ 5 ml pen/strep 15140 Life Technologies

CULTURE MEDIUM FOR EXPANDING BREAST EPITHELIAL STEM CELLS

This application is a national phase entry pursuant to 35 U.S.C. § 371 of International Application No. PCT/EP2015/077988, filed Nov. 27, 2015, which claims the benefit of priority of Great Britain Application No. 1421094.2, filed Nov. 27, 2014, each of which is incorporated by reference herein in its entirety for any purpose.

All documents cited herein are incorporated by reference in their entirety.

TECHNICAL FIELD

The invention is in the field of breast epithelial stem cell culture media and methods, in particular culture media and methods for expanding populations of breast epithelial stem cells, e.g. human breast epithelial stem cells.

BACKGROUND

There is great interest in culture media and methods for expanding populations of stem cells. Populations of stem cells have many uses. For example, stem cells and their differentiated progeny can be used in cellular assays, drug screening, and toxicity assays. Stem cells also show promise for cell-based therapies, such as in regenerative medicine for the treatment of damaged tissue. Furthermore, efficient cell culture media are important for providing and maintaining populations of cells for research purposes.

Methods for the long-term culture of epithelial stem cells or tissue fragments derived from several tissues (e.g. pancreas, colon, intestinal crypts, stomach, liver and prostate) have been described (see WO 2010/090513, WO2012/014076 and WO2012/168930). However, these methods have been found to be unable to support the long-term culture of epithelial stem cells or tissue fragments derived from breast tissue.

A culture system for culturing epithelial stem cells derived from normal breast tissue is described in Pasic et al. (2011) Genes & Development 25:1641-1653. However, this system is unable to support long-term culture of breast organoids. Cultures using this system have been observed to stop expanding after 2-3 passages. Accordingly, it is not possible to obtain large numbers of stem cells using this technique. A culture system for culturing circulating tumour cells from breast cancer patients is described in Yu et al. (2014) Science 345(6193):216-220. However, the authors of this paper provided no guidance with respect to culturing breast epithelial stem cells obtained from normal breast tissue, primary tumour or metastases. Furthermore, circulating breast tumour cells cultured using the Yu et al. system form aggregates of cells.

Therefore, there is a need for culture media and methods for culturing breast epithelial stem cells obtained from normal breast tissue, primary tumours or metastases that permit long-term culture. There is also a need for culture media and methods for culturing circulating breast tumour cells that permit the formation of breast organoids that closely resemble breast tumours.

SUMMARY OF THE INVENTION

The invention provides a method for expanding breast epithelial stem cells comprising:

providing a population of breast stem cells;
providing a culture medium comprising an ErbB3/4 ligand, one or more FGFR2b ligands and a Wnt agonist;
contacting the stem cells with the culture medium; and
culturing the cells under appropriate conditions.

The invention further provides a culture medium comprising an ErbB3/4 ligand and one or more FGFR2b ligands and a Wnt agonist.

The invention further provides a culture medium comprising an ErbB3/4 ligand suitable for expanding a population of breast epithelial stem cells for at least 4 passages.

The invention further provides a breast organoid which comprises a population of breast epithelial stem cells. In some embodiments, said breast organoid is obtainable or obtained by a method of the invention.

The invention further provides a breast organoid of the invention in a culture medium of the invention.

The invention further provides the use of a breast organoid of the invention, or a cell derived from said organoid, in a drug discovery screen; toxicity assay; research of tissue embryology, cell lineages, or differentiation pathways; gene expression studies including recombinant gene expression; research of mechanisms involved in tissue injury or repair; research of inflammatory and infectious diseases; studies of pathogenetic mechanisms; or studies of mechanisms of cell transformation or aetiology of cancer.

The invention further provides an organoid of the invention, or a cell derived from said organoid, for use in medicine.

The invention further provides a culture medium comprising a p53 stabilising agent.

DESCRIPTION OF THE DRAWINGS

FIG. 2. Phase contrast images of established and promising mammary (A) tumour and (B) normal organoid lines. Scale bars equal 150 µm.

Krt8=keratin-8 (clone Ks8.7, sc101459 Santa Cruz), Krt14=keratin-14 (clone AF64, PRB-155P Covance), ER=estrogen receptor alpha (clone C1355, Fisher 50-172-167), E-cadherin (clone 36/E-cadherin, 61082 BD Biosciences), HER2=human epidermal growth factor receptor 2 (c-erbB2) (clone SP3, #RM-9103, Thermoscientific), PR=progesterone receptor (clone PgR 636, M356929 Dako).

Figure 7:
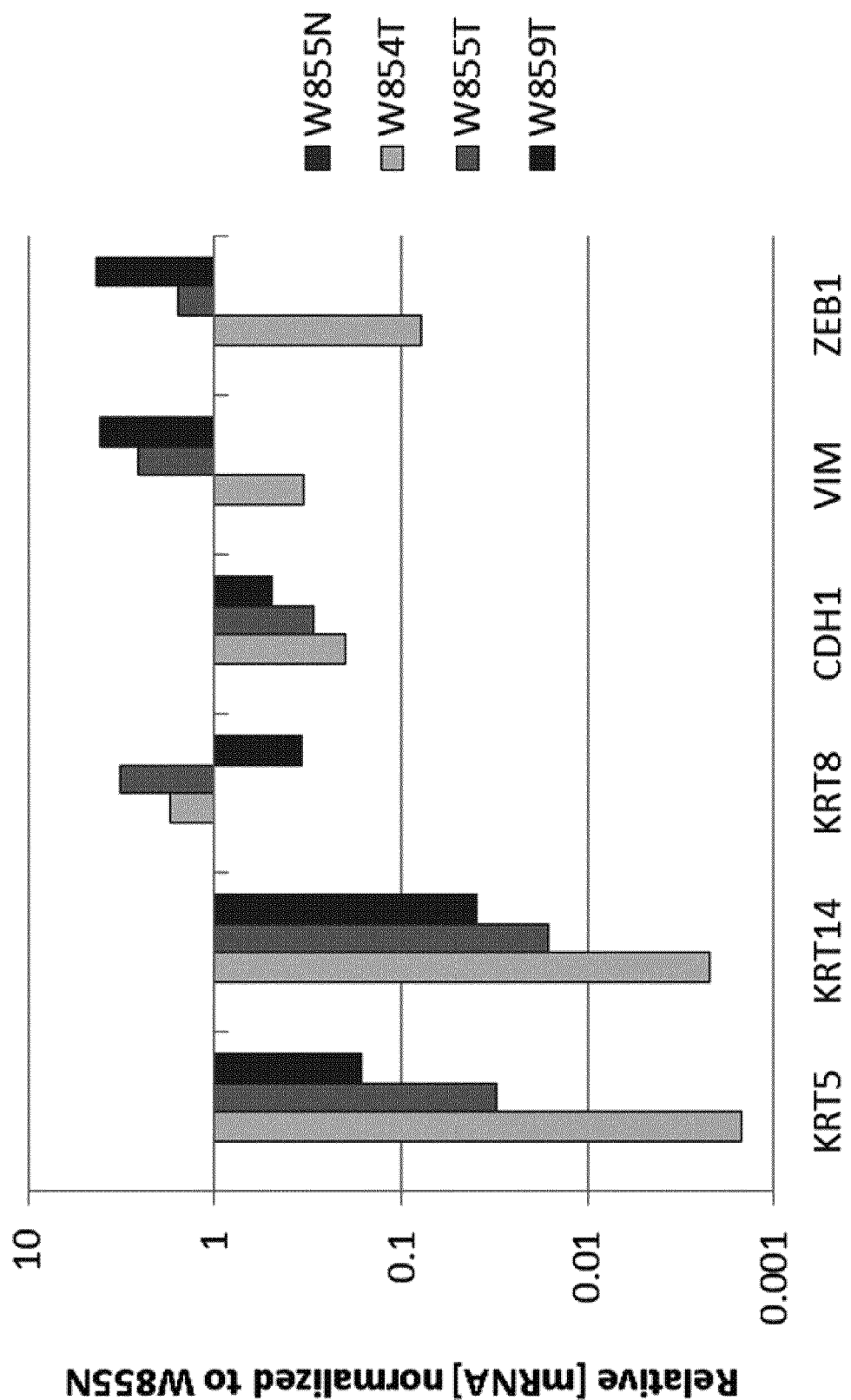

FIG. 7. Quantitative PCR on organoids for basal (KRT5/14), luminal (KRT8), epithelial (CDH1) and mesenchymal (VIM, ZEB1) markers normalized to normal mammary organoid line W855N.

Figure 8:
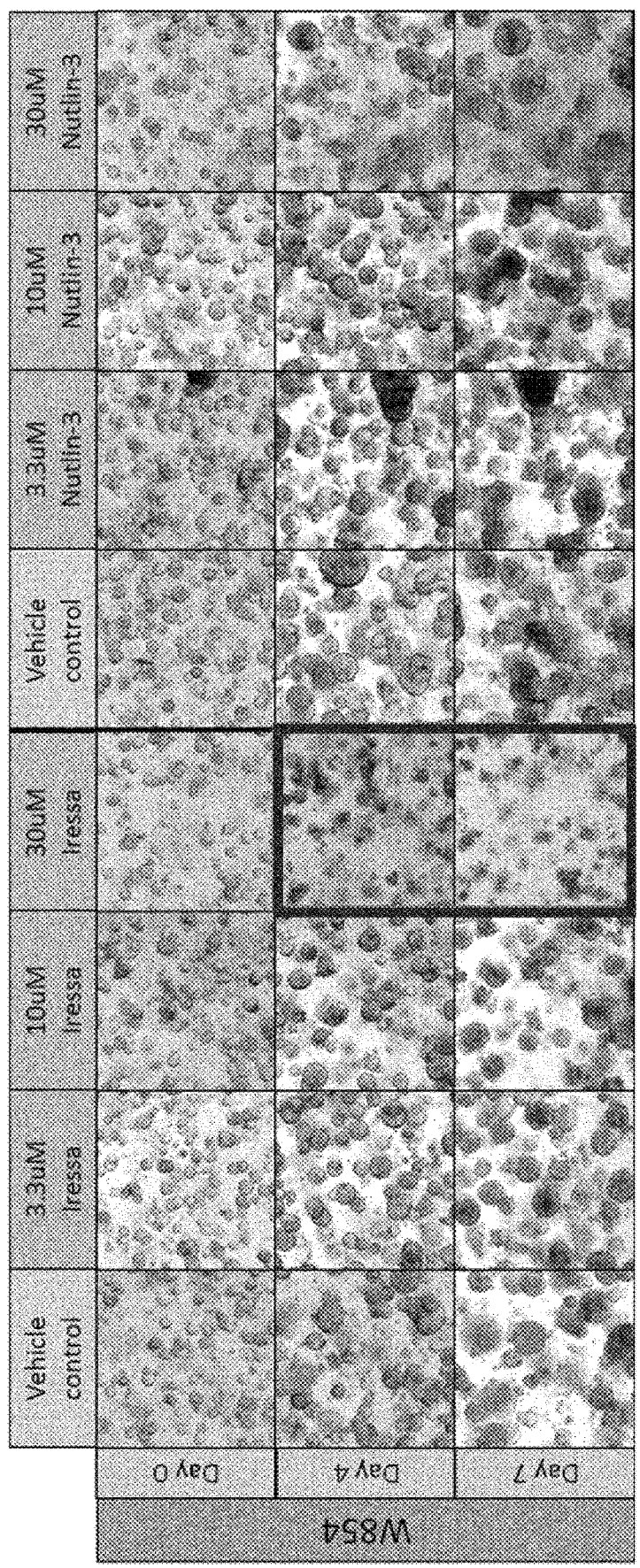

FIG. 8. Phase-contrast images of mammary tumour organoid lines W854T, W855T and W859T during a pilot drug screen with increasing doses of the EGFR inhibitor Iressa or the p53 stabilizer Nutlin-3. Visibly affected organoids are marked by bold black boxes. Image widths are 500 μm.

Figure 9:
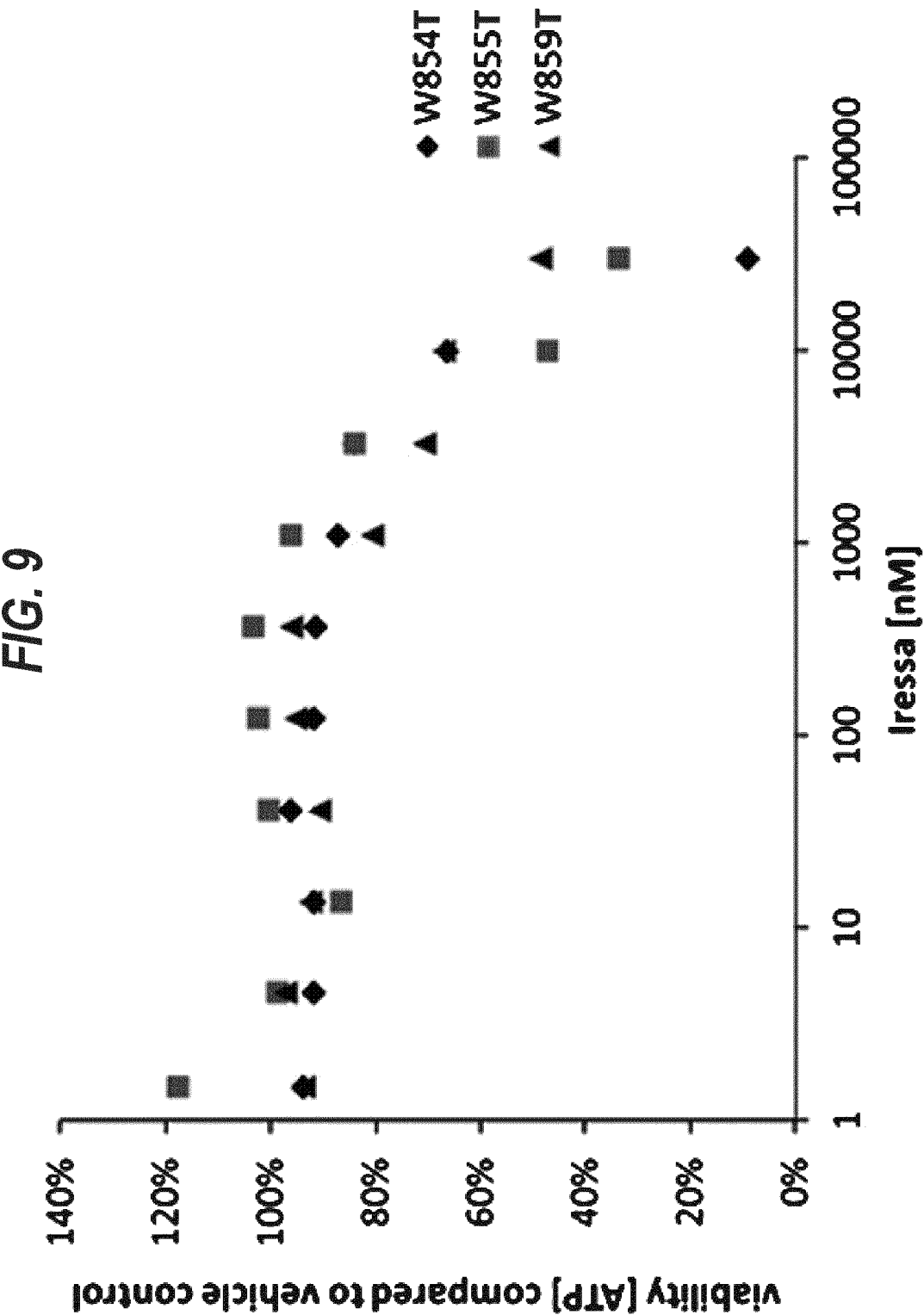

FIG. 9. Viability of mammary tumour organoid lines W854T, W855T and W859T treated with increasing does of the EGFR inhibitor Iressa or the p53 stabilizer Nutlin-3 for 7 days, as measured by a luminescent ATP assay (CellTiter-Glo 2.0, G9241 Promega).

Figure 10:
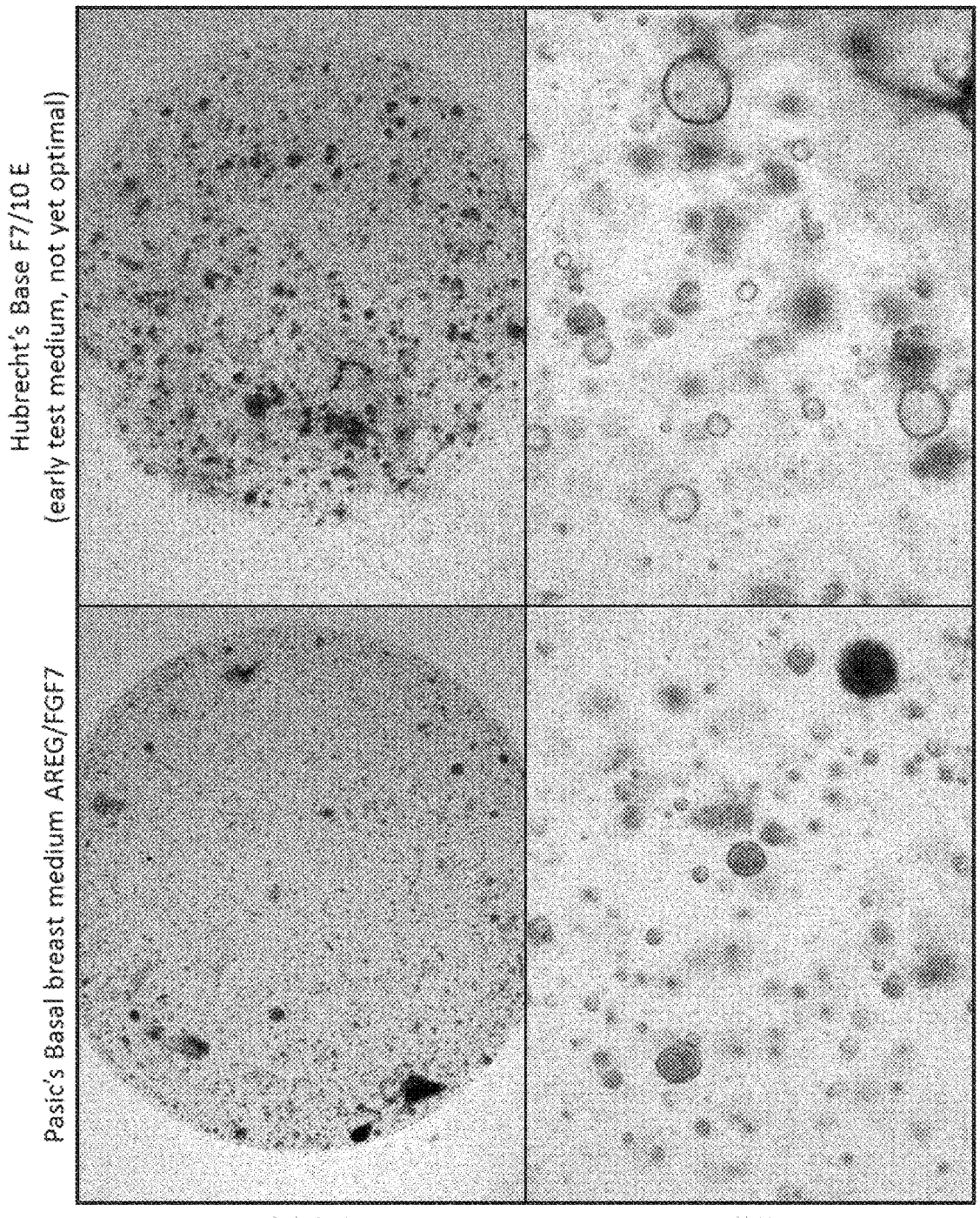

FIG. 10. Normal human mammary organoids in the culture medium described in Pasic et al. compared with organoids from the same patient grown in base-F7/10E medium.

Figure 11:
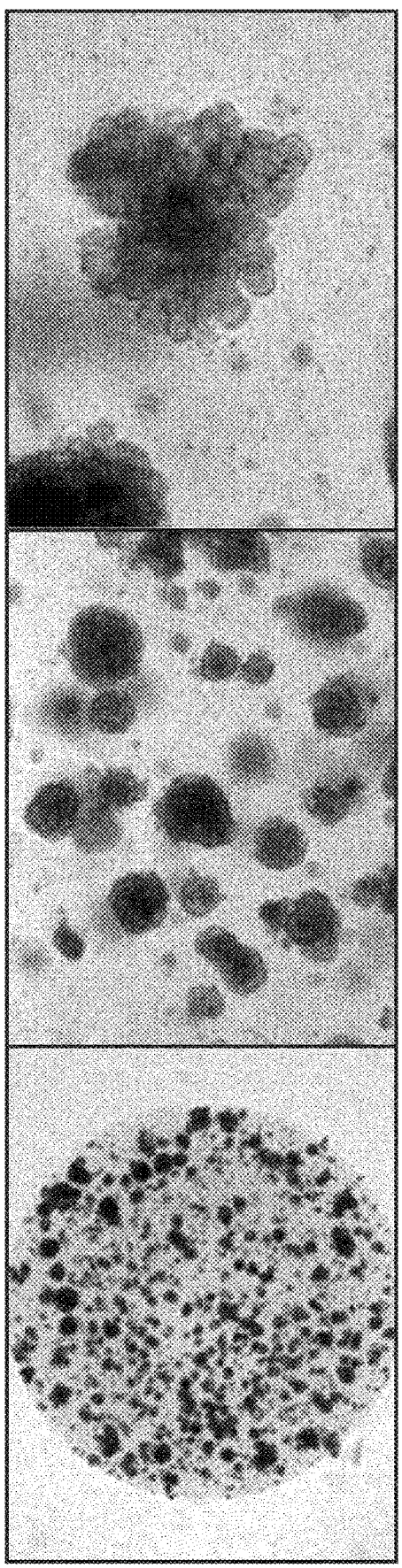

FIG. 11. Mouse mammary tumour organoids. Phase-contrast images of organoids established from KB2P mammary tumors lacking Brca2 and p53, Passage 4, Image widths are 7 mm, 1.5 mm, and 600 μm.

Figure 12:
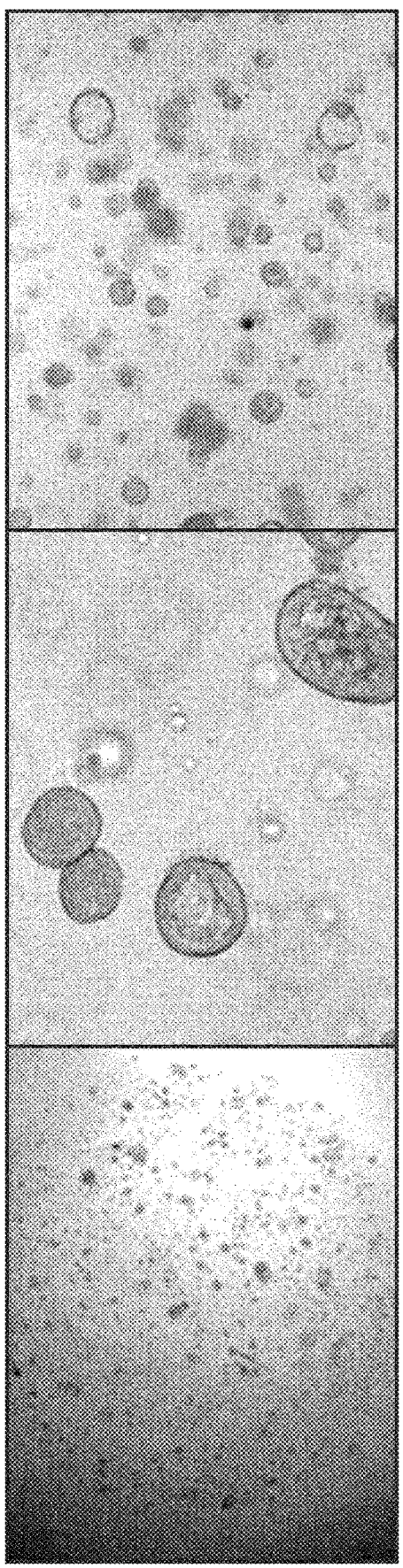

FIG. 12. Human metastatic mammary tumor organoids. Phase-contrast images of organoids established from a human breast cancer metastasis to the skin, Passage 5, Image widths are 7 mm, 1.5 mm, and 600 μm.

FIG. 13. Overview of mammary organoid cultures.

FIG. 14. Organoid culture media.

DETAILED DESCRIPTION

Methods for culturing epithelial stem cells from a variety of tissues have previously been described in WO2010/090513, WO2012/014076 and WO2012/168930. The present inventors have surprisingly found that adding an ErbB3/4 ligand to the culture medium allows breast epithelial stem cells to be cultured for an increased number of passages compared to when the ErbB3/4 ligand is absent from the medium.

The ability to keep the cells and resulting organoids alive for longer and increase the passage number advantageously allows more cells to be obtained from a collection of starting cells than was possible using previous methods. This enables a large number of cells to be available for various applications, for example, drug screening, in which a large amount of material is required to test various different drugs. The ability to generate the cells from a single starting source is advantageous for such applications where it is necessary to compare results between experiments. Furthermore, the enhanced ability to obtain more cells from a small collection of starting cells (e.g. a collection of approximately 100-300 cells) is advantageous for applications where little starting material is available, such as biopsies of primary or metastatic cancer or circulating tumour cells. Similarly, it means that many cells are available for use in transplants, e.g. in breast reconstruction or breast enhancement, and that multiple patients may be transplanted with cells obtained from a useful donor.

Culturing the cells in a medium of the invention allows the cells to multiply whilst retaining their stem or progenitor cell phenotype, which is referred to herein as expansion. Organoids are formed comprising these stem or progenitor cells. Use of the medium of the invention is therefore advantageous for providing increased numbers of these useful stem or progenitor cells and for obtaining organoids containing these cells.

Accordingly, there is provided a method for culturing breast epithelial stem cells, wherein said method comprises culturing one or more breast epithelial stem cells in contact with an extracellular matrix in the presence of a culture medium, the culture medium comprising a basal medium for animal or human cells to which is added one or more ErbB3/4 ligands.

The culture medium used in the method of the invention is preferably a culture medium of the invention as described herein.

Accordingly, there is also provided a culture medium comprising a basal medium for animal or human cells to which is added one or more ErbB3/4 ligands (e.g. 1, 2, 3, 4, or more than 4), and one or more ligands of FGFR2b (e.g. 1, 2, 3, 4 or more than 4), preferably wherein the one or more ligands of FGFR2b is FGF7 and/or FGF10, for example, for use in the above method.

Accordingly, there is also provided a culture medium comprising a basal medium for animal or human cells to which is added one or more ErbB3/4 ligands (e.g. 1, 2, 3, 4, or more than 4), and one or more Wnt agonists (e.g. 1, 2, 3, 4 or more than 4), for example, for use in the above method.

In some embodiments, the one or more Wnt agonists is a Lgr5 agonist, Lgr4 agonist, Lgr6 agonist or Wnt3a. In some embodiments, the Lgr5 agonist is an Rspondin, e.g. any one of Rspondin 1-4.

In preferred embodiments, the culture medium of the invention comprises a basal medium for animal or human cells to which is added one or more ErbB3/4 ligands (e.g. 1, 2, 3, 4, or more than 4), one or more ligands of FGFR2b (e.g. 1, 2, 3, 4 or more than 4), preferably wherein the one or more ligands of FGFR2b is FGF7 and/or FGF10, and one or more Wnt agonists (e.g. 1, 2, 3, 4 or more than 4), preferably wherein the one or more Wnt agonists is a Lgr5 agonist, preferably wherein the Lgr5 agonist is an Rspondin, e.g. any one of Rspondin 1-4.

In some embodiments, the culture medium of the invention or the culture medium used in the method of the invention comprises one or more additional components selected from: a ligand of FGFR2b (e.g. FGF7 and/or FGF10), a Lgr5 agonist (e.g. Rspondin, e.g. any one of Rspondin 1-4), a BMP inhibitor (for example, Noggin), B27, N-acetylcysteine, Nicotinamide, a ROCK inhibitor, a TGF-beta inhibitor (for example, an ALK 4, 5, 7 inhibitor, e.g. A83-01) and a p38 MAP kinase inhibitor (for example, SB 202190). In some embodiments, the culture medium further comprises at least two, at least three, at least four, at least five, at least six, at least seven, (e.g. 2, 3, 4, 5, 6, 7) of these additional components. In some embodiments, the culture medium further comprises all of these additional components.

In some embodiments, the culture medium further comprises a further receptor tyrosine kinase ligand, e.g. EGF.

In some embodiments, the culture medium further comprises a Wnt agonist, e.g. Wnt3a.

In some embodiments, the culture medium further comprises one or more of amphiregulin, TGF-alpha and PDGF-CC. For example, in some embodiments the culture medium further comprises PDGF-CC. In some embodiments, the culture medium further comprises amphiregulin, TGF-alpha and PDGF-CC. The invention therefore provides the use of an ErbB3/4 ligand for culturing breast epithelial stem cells.

The invention also provides a method for culturing breast epithelial stem cells which uses an expansion medium as described in WO2012/168930, WO2010/090513 or WO2012/014076 to which at least one (e.g. 1, 2, 3, 4, or more than 4) ErbB3/4 ligand and at least one (e.g. 1, 2, 3, 4, or more than 4) FGFR2b ligands are added.

The present inventors have also surprisingly found that the addition of a p53 stabilizing agent to a culture medium can ensure that the cell population is predominantly tumour cells. Without wishing to be bound by any theory, it is believed that p53 stabilizing agents increase the cellular concentration of p53 (e.g. by blocking the interaction between p53 and Mdm2), stimulate p53-dependent expression and induce cellular senescence. p53 mutations commonly occur in tumour cells, which may result in the mutant p53 protein being unable to be stabilised by a p53 stabilizing agent. Thus, a subset of tumour cells with the mutant p53 protein would escape the senescence induced by a p53 stabilizing agent and outgrow normal cells in a mixed population.

The invention therefore further provides the use of a p53 stabilizing agent for culturing tumour cells.

The invention also provides a method for culturing tumour stem cells which uses an expansion medium as described herein or in WO2012/168930, WO2010/090513 or WO2012/014076 to which at least one (e.g. 1, 2, 3, 4, or more than 4) p53 stabilizing agent is added. The invention also provides a culture medium comprising a p53 stabilizing agent. Preferably, the culture medium is a culture medium as described herein or in WO2012/168930, WO2010/090513 or WO2012/014076. Preferably, the culture medium is suitable for culturing epithelial stem cells.

A preferred p53 stabilizing agent is a member of the Nutlin family, e.g. Nutlin-1, Nutlin-2 or Nutlin-3. For example, in some embodiments, the p53 stabilizing agent is Nutlin-3. Other p53 stabilising agents are known in the art (e.g. CP-31398) and the skilled person will be able to use any of these accordingly.

ErbB3/4 Ligand

The ErbB receptor tyrosine kinase family consists of four cell surface receptors: i) ErbB1/EGFR/HER1, ii) ErbB2/HER2, iii) ErbB3/HER3, and iv) ErbB4/HER4. An ErbB3/4 ligand is herein defined as a ligand that is capable of binding to ErbB3 and/or ErbB4. Accordingly, EGF is not an ErbB3/4 ligand because it does not bind to ErbB3/4. In some embodiments, the Erb3/4 ligand binds to ErbB3 and does not bind to ErbB4. In some embodiments, the Erb3/4 ligand binds to Erb4 and does not bind to Erb3. In some embodiments, binding of the ErbB3/4 ligand to ErbB3 or ErbB4 induces the heterodimerization of said ErbB3 or said ErbB4 with ErbB2. In some embodiments, the induction of heterodimerization of ErbB3 or ErbB4 with ErbB2 stimulates intrinsic kinase activity, which leads to tyrosine phosphorylation. In the context of a culture medium of the invention, an ErbB3/4 ligand is known as "N".

Various ErbB3/4 ligands are known in the art. In preferred embodiments, the one or more ErbB3/4 ligands of the culture medium are members of the neuregulin/heregulin family. The neuregulin/heregulin family is referred to herein as the neuregulin family. The neuregulin family is a family of structurally related polypeptide growth factors that are gene products of alternatively spliced genes NRG1, NRG2, NRG3 and NRG4. In more preferred embodiments, the one or more ErbB3/4 ligands of the culture medium are polypeptides that are gene products of one or more of NRG1, NRG2, NRG3 and NRG4 (i.e. a neuregulin polypeptide). In some embodiments, the ErbB3/4 ligand is a polypeptide that is a gene product of NRG1. The polypeptide that is a gene product of NRG1, NRG2, NRG3 and NRG4 may be any of the isoforms that result from the alternative splicing of NRG1, NRG2, NRG3 or NRG4 mRNA. Thus, for example, the polypeptide that is a gene product of NRG1 may be any of the following isoforms: Type I NRG1 (also known as heregulin, NEU differentiation factor (NDF) or acetylcholine receptor inducing activity (ARIA)), Type II NRG1 (also known as Glial Growth Factor-2 (GGF2)), Type III NRG1 (also known as Sensory and motor neuron-derived factor (SMDF)), Type IV NRG1, Type V NRG1 or Type VI NRG1. In some embodiments, the neuregulin polypeptide is pro-neuregulin-1, membrane-bound isoform isoform HRG-beta1 (NP_039250.2), pro-neuregulin-1, membrane-bound isoform isoform HRG-beta1b (NP_001153471.1), pro-neuregulin-1, membrane-bound isoform isoform HRG-beta1c (NP_001153467.1), pro-neuregulin-1 or membrane-bound isoform isoform HRG-beta1d (NP_001153473.1).

In some embodiments the ErbB3/4 ligand is of human origin. Accordingly, in some embodiments the ErbB3/4 ligand is a human gene product of one or more of NRG1, NRG2, NRG3 and NRG4 (i.e. a human neuregulin polypeptide).

In some embodiments, the NRG1 gene has the sequence of Gene ID: 3084 or NG_012005.1. In some embodiments, the NRG2 gene has the sequence of Gene ID: 9542. In some embodiments, the NRG3 gene has the sequence of Gene ID: 10718 or NG_013373.1. In some embodiments, the NRG4 gene has the sequence shown of Gene ID: 145957.

In some embodiments a neuregulin polypeptide is a gene product of NRG1 and has the sequence shown in NP_001153467.1 (SEQ ID NO: 1), NP_001153468.1 (SEQ ID NO: 2), NP_001153471.1 (SEQ ID NO: 3), NP_001153473.1 (SEQ ID NO: 4), NP_001153474.1 (SEQ ID NO: 5), NP_001153476.1 (SEQ ID NO: 6), NP_001153477.1 (SEQ ID NO: 7), NP_001153479.1 (SEQ ID NO: 8), NP_001153480.1 (SEQ ID NO: 9), NP_004486.2 (SEQ ID NO: 10), NP_039250.2 (SEQ ID NO: 11), NP_039251.2 (SEQ ID NO: 12), NP_039252.2 (SEQ ID NO: 13), NP_039253.1 (SEQ ID NO: 14), NP_039254.1 (SEQ ID NO: 15), NP_039256.2 (SEQ ID NO: 16) or NP_039258.1 (SEQ ID NO: 17). In some embodiments a neuregulin polypeptide is a gene product of NRG2 and has the sequence shown in NP_001171864.1 (SEQ ID NO: 18), NP_004874.1 (SEQ ID NO: 19), NP_053584.1 (SEQ ID NO: 20), NP_053585.1 (SEQ ID NO: 21), or NP_053586.1 (SEQ ID NO: 22). In some embodiments a neuregulin polypeptide is a gene product of NRG3 and has the sequence shown in NP_001010848.2 (SEQ ID NO: 23), NP_001159444.1 (SEQ ID NO: 24), or NP_001159445.1 (SEQ ID NO: 25). In some embodiments a neuregulin polypeptide is a gene product of NRG4 and has the sequence shown in NP_612640.1 (SEQ ID NO: 26).

In some embodiments, the at least one ErbB3/4 ligand is a biologically active variant of one or more naturally occurring ErB3/4 ligands, for example, of one or more members of the neuregulin family. Neuregulin variants, which may be naturally occurring (e.g. allelic variants that occur at the NRG1 locus) or recombinantly produced, have amino acid sequences that are the same as, similar to or substantially similar to a neuregulin polypeptide.

In some embodiments, a neuregulin variant has a sequence that is at least 70%, at least 80%, at least 85%, at least 90%, at least 95%, at least 96%, at least 97%, at least 98%, at least 99%, or 100% identical to a neuregulin polypeptide, for example the neuregulin variant has a sequence that is at least 70%, at least 80%, at least 85%, at least 90%, at least 95%, at least 96%, at least 97%, at least 98%, at least 99%, or 100% identical to any one of SEQ ID NOs: 1-26.

In some embodiments, the at least one ErbB3/4 ligand is at least one biologically active fragment of at least one naturally occurring ErbB3/4 ligand, for example a biologically active fragment of of one or more neuregulin polypeptides.

"Biologically active" is defined herein as meaning that the ErbB3/4 ligand, for example, the variant or fragment, is capable of binding to ErbB3 and/or ErbB4, optionally wherein binding to ErbB3 and/or ErbB4 induces the heterodimerization of said ErbB3 or said ErbB4 with ErbB2, and optionally wherein said induction of heterodimerization of ErbB3 or ErbB4 with ErbB2 stimulates intrinsic kinase activity, which leads to tyrosine phosphorylation.

In some embodiments, the ErbB3/4 ligand is a fragment of the polypeptide having the amino acid sequence recited in any one of SEQ ID NOs: 1-26 wherein the fragment comprises at least 30, at least 35, at least 40, at least 45, at least 50, at least 55, at least 60, at least 65, at least 70, at least 75, at least 80, at least 85, at least 90, at least 95 or at least 100 amino acids of the sequence recited in any one of SEQ ID NOs: 1-26.

In some embodiments, the ErbB3/4 ligand is a variant of the polypeptide having the amino acid sequence recited in any one of SEQ ID NOs: 1-26, wherein the variant has an amino acid sequence that is at least 50%, at least 60%, at least 70%, at least 80%, at least 85%, at least 90%, at least 95%, at least 96%, at least 97%, at least 98%, at least 99%, or 100% identical to the polypeptide having the amino acid sequence recited in any one of SEQ ID NOs: 1-26.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of *Current Protocols in Molecular Biology* (F. M. Ausubel et al., eds., 1987) Supplement 30. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in Smith & Waterman (1981) *Adv. Appl. Math.* 2: 482-489.

In some embodiments, the ErbB3/4 ligand is a variant of a fragment of the polypeptide having the amino acid sequence recited in any one of SEQ ID NOs: 1-26, wherein the fragment comprises at least 30, at least 35, at least 40, at least 45, at least 50, at least 55, at least 60, at least 65, at least 70, at least 75, at least 80, at least 85, at least 90, at least 95 or at least 100 amino acids of the sequence recited in any one of SEQ ID NOs: 1-26, and wherein the variant has an amino acid sequence that is at least 50%, at least 60%, at least 70%, at least 80%, at least 85%, at least 90%, at least 95%, at least 96%, at least 97%, at least 98%, at least 99%, or 100% identical to the fragment.

In some embodiments, the ErbB3/4 ligand is a fragment of a biologically active variant of the polypeptide having the amino acid sequence recited in any one of SEQ ID NOs: 1-26, wherein the variant has an amino acid sequence that is at least 50%, at least 60%, at least 70%, at least 80%, at least 85%, at least 90%, at least 95%, at least 96%, at least 97%, at least 98%, at least 99%, or 100% identical to the polypeptide having the amino acid sequence recited in any one of SEQ ID NOs: 1-26, and wherein the fragment comprises at least 30, at least 35, at least 40, at least 45, at least 50, at least 55, at least 60, at least 65, at least 70, at least 75, at least 80, at least 85, at least 90, at least 95 or at least 100 amino acids of the variant.

In some embodiments, the ErbB3/4 ligand is a non-naturally occurring ligand, for example a synthetic ligand or an anti-ErbB3/4 antibody. Methods of generating antibodies against a target of interest are well known in the art. In some embodiments, the anti-ErbB3/4 antibody is an agonistic anti-ErbB3/4 antibody. Preferably, the antibody is biologically active. Any suitable antibodies may be used, for example, as described herein.

ErbB3/4 ligands can be identified using methods known in the art, for example, binding of GST-tagged candidate ligands to insect-cell-expressed ErbB receptors causing tyrosine phosphorylation (Carraway $3^{rd}$ et al., (1997) Nature 387(6632):512-6).

In some embodiments, the ErbB3/4 ligand comprises an EGF domain or EGF-like domain. EGF and EGF-like domains are evolutionary conserved protein domains that are recognised in the art (see, for example, Wouters et al. (2005) Protein Sci. 14(4): 1091-1103). Accordingly, in some embodiments in which the ErbB3/4 ligand is a biologically active fragment of at least one naturally occurring ErbB3/4 ligand, the fragment comprises an EGF domain or an EGF-like domain.

In some embodiments, the ErbB3/4 ligand is human neuregulin β-1. In some embodiments, the human neuregulin β-1 has the amino acid sequence recited in SEQ ID NO: 27. Human neuregulin β-1 is a fragment of a neuregulin polypeptide, wherein the fragment comprises an EGF-like domain. In a preferred embodiment, the ErbB3/4 ligand comprises or consists of the EGF-like domain of human neuregulin β-1.

In some embodiments the ErbB3/4 ligand has similar biological activity to recombinant human neuregulin β-1.

In some embodiments, the ErbB3/4 ligand is a fragment of the polypeptide having the amino acid sequence recited in SEQ ID NO: 27, wherein the fragment comprises at least 30, at least 35, at least 40, at least 45, at least 50, at least 55, at least 60, at least 62, or at least 64 amino acids of the sequence recited in SEQ ID NO: 27.

In some embodiments, the ErbB3/4 ligand is a variant of the polypeptide having the amino acid sequence recited in SEQ ID NO: 27, wherein the variant has an amino acid sequence that is at least 50%, at least 60%, at least 70%, at least 80%, at least 85%, at least 90%, at least 95%, at least 96%, at least 97%, at least 98%, at least 99%, or 100% identical to the polypeptide having the amino acid sequence recited in SEQ ID NO: 27.

In some embodiments, the ErbB3/4 ligand is a variant of a fragment of the polypeptide having the amino acid sequence recited in SEQ ID NO: 27, wherein the fragment comprises at least 30, at least 35, at least 40, at least 45, at least 50, at least 55, at least 60, at least 62 or at least 64 amino acids of the sequence recited in SEQ ID NO: 27, and wherein the variant has an amino acid sequence that is at least 50%, at least 60%, at least 70%, at least 80%, at least 85%, at least 90%, at least 95%, at least 96%, at least 97%, at least 98%, at least 99%, or 100% identical to the fragment.

In some embodiments, the ErbB3/4 ligand is a fragment of a biologically active variant of the polypeptide having the amino acid sequence recited in SEQ ID NO: 27, wherein the variant has an amino acid sequence that is at least 50%, at least 60%, at least 70%, at least 80%, at least 85%, at least 90%, at least 95%, at least 96%, at least 97%, at least 98%, at least 99%, or 100% identical to the polypeptide having the amino acid sequence recited in SEQ ID NO: 27, and wherein the fragment comprises at least 30, at least 35, at least 40, at least 45, at least 50, at least 55, at least 60, at least 62 or at least 64 amino acids of the variant.

The ErbB3/4 ligand may be present at any suitable concentration. For example, the ErbB3/4 ligand may be present at a concentration of between 0.05 and 500 nM, between 0.05 and 100 nM, between 0.05 and 50 nM, between 0.05 and 10 nM, between 0.05 and 5 nM, between 0.05 and 1 nM, between 0.5 and 500 nM, between 0.5 and 100 nM, between 0.5 and 50 nM, between 0.5 and 10 nM, between 0.5 nM and 1 nM, between 1 and 10 nM, between 3 and 10 nM, between 3 and 8 nM, between 4 and 6 nM. For example, the ErbB3/4 ligand may be present at a concentration of approximately 5 nM. In some embodiments, the ErbB3/4 ligand is used at a concentration of at least 0.05 nM, at least 0.5 nM, at least 1 nM, at least 3 nM, at least 4 nM, at least 5 nM, at least 10 nM, at least 50 nM, or at least 100 nM.

Additionally to the ErbB3/4 ligand, cell culture media generally contain a number of components which are necessary to support maintenance and/or expansion of the cultured cells. A cell culture medium of the invention will therefore normally contain many other components in addition to an ErbB3/4 ligand. Suitable combinations of components can readily be formulated by the skilled person, taking into account the disclosure herein. A culture medium according to the invention will generally be a nutrient solution comprising standard cell culture components, such as amino acids, vitamins, inorganic salts, a carbon energy source, and a buffer as described in more detail below. Other standard cell culture components that may be included in the culture include hormones, such as progesterone, proteins, such as albumin, catalase, insulin and transferrin. These other standard cell culture components make up the "basal" culture medium.

A culture medium according to the invention may be generated by modification of an existing cell culture medium. The skilled person will understand from common general knowledge the types of culture media that might be suitable for modification for use in epithelial stem cell culture. Suitable cell culture media are available commercially, and include, but are not limited to, Dulbecco's Modified Eagle Media (DMEM), Minimal Essential Medium (MEM), Knockout-DMEM (KO-DMEM), Glasgow Minimal Essential Medium (G-MEM), Basal Medium Eagle (BME), DMEM/Ham's F12, Advanced DMEM/Ham's F12, Iscove's Modified Dulbecco's Media and Minimal Essential Media (MEM), Ham's F-10, Ham's F-12, Medium 199, and RPMI 1640 Media. Examples of suitable "basal" culture are also provided in WO2012/168930, WO2010/090513, and WO 2012/014076.

In some embodiments, the basal medium is AdDF+++. In some embodiments, the AdDF+++ comprises Advanced DMEM/F12 (Dulbecco's Modified Eagle Medium/Ham's F-12), GlutaMax, HEPES, penicillin/streptomycin, primocin.

In some embodiments, the basal medium is D10F. In some embodiments, the D10F comprises 31966-DMEM (Dulbecco's Modified Eagle Medium), fetal bovine serum (FBS) and penicillin/streptomycin.

Thus, in some embodiments, one of these pre-existing cell culture media is used as the basal culture medium to which is added the one or more Erb3/4 ligands. As mentioned above, the culture medium of the invention additionally comprises one or more ligands of FGFR2b (for example, FGF7 and/or FGF10) and/or one or more Wnt agonists (preferably an agonistic Lgr5 ligand, preferably Rspondin). In some embodiments, the culture medium of the invention comprises the following additional components: (i) FGF7 and/or FGF10 and (ii) Rspondin. In some embodiments, the culture medium of the invention comprises the following additional components: (i) FGF7 and/or FGF10, (ii) Rspondin and (iii) one or more further receptor tyrosine kinase ligands.

In some embodiments, the culture medium of the invention further comprises one or more components selected from: a BMP inhibitor (for example, Noggin), B27, N-acetylcysteine, Nicotinamide, a ROCK inhibitor, a TGF-beta inhibitor (for example, A83-01), a p38 MAP kinase inhibitor (for example, SB 202190).

In some embodiments, the culture medium of the invention comprises an ErbB3/4 ligand, Rspondin, a BMP inhibitor (for example, Noggin), B27, N-acetylcysteine, Nicotinamide, a ROCK inhibitor, a TGF-beta inhibitor (for example, A83-01), a p38 MAP kinase inhibitor (for example, SB 202190), FGF7 and FGF10, and optionally one or more additional components selected from: one or more further receptor tyrosine kinase ligands (for example, EGF, amphiregulin, TGF-alpha, PDGF), a p53 stabilizing agent and a Wnt agonist (for example, Wnt3a).

As will be apparent to the skilled reader, the preferred culture methods of the invention are advantageous because feeder cells are not required. Feeder cell layers are often used to support the culture of stem cells, and to inhibit their differentiation. A feeder cell layer is generally a monolayer of cells that is co-cultured with, and which provides a surface suitable for growth of, the cells of interest. The feeder cell layer provides an environment in which the cells of interest can grow. Feeder cells are often mitotically inactivated (e.g. by irradiation or treatment with mitomycin C) to prevent their proliferation. The use of feeder cells is undesirable, because it complicates passaging of the cells (the cells must be separated from the feeder cells at each passage, and new feeder cells are required at each passage). The use of feeder cells can also lead to contamination of the desired cells with the feeder cells. This is clearly problematic for any medical applications, and even in a research context, complicates analysis of the results of any experiments performed on the cells. The culture media of the invention are particularly advantageous because they can be used to culture cells without feeder cell contact, i.e. the methods of the invention do not require a layer of feeder cells to support the cells whose growth is being sponsored.

Accordingly, the compositions of the invention may be feeder cell-free compositions. A composition is conventionally considered to be feeder cell-free if the cells in the composition have been cultured for at least one passage in the absence of a feeder cell layer. A feeder cell-free composition of the invention will normally contain less than about 5%, less than about 4%, less than about 3%, less than about 2%, less than about 1% feeder cells (expressed as a % of the total number of cells in the composition) or preferably no feeder cells at all.

BMP Inhibitors

The culture media of the invention may comprise one or more bone morphogenetic protein (BMP) inhibitor.

In some embodiments, the culture medium may comprise any suitable BMP inhibitor. BMPs bind as a dimeric ligand to a receptor complex consisting of two different receptor serine/threonine kinases, type I and type II receptors. The type II receptor phosphorylates the type I receptor, resulting in the activation of this receptor kinase. The type I receptor subsequently phosphorylates specific receptor substrates (SMAD), resulting in a signal transduction pathway leading to transcriptional activity. Advantageously, BMP inhibitors promote expression of Lgr5, and so the presence of a BMP inhibitor in a culture medium of the invention will likely result in more proliferative organoids than if the BMP inhibitor is absent. In some embodiments, cells cultured with a BMP inhibitor have upregulated expression of Lgr5 compared to cells cultured without a BMP inhibitor. Therefore, addition of a BMP inhibitor typically results in more proliferative organoids.

A BMP inhibitor is defined as an agent that binds to a BMP molecule to form a complex wherein the BMP activity is neutralized, for example by preventing or inhibiting the binding of the BMP molecule to a BMP receptor. Alternatively, said inhibitor is an agent that acts as an antagonist or reverse agonist. This type of inhibitor binds with a BMP receptor and prevents binding of a BMP to said receptor. An example of a latter agent is an antibody that binds a BMP receptor and prevents binding of BMP to the antibody-bound receptor.

A BMP inhibitor may be added to the media in an amount effective to inhibit a BMP-dependent activity in a cell to at most 90%, more preferred at most 80%, more preferred at most 70%, more preferred at most 50%, more preferred at most 30%, more preferred at most 10%, more preferred 0%, relative to a level of a BMP activity in the absence of said inhibitor, as assessed in the same cell type. As is known to a skilled person, a BMP activity can be determined by measuring the transcriptional activity of BMP, for example as exemplified in Zilberberg et al., 2007. BMC Cell Biol. 8:41.

Several classes of natural BMP-binding proteins are known, including Noggin (Peprotech), Chordin and chordin-like proteins (R&D systems) comprising chordin domains, Follistatin and follistatin-related proteins (R&D systems) comprising a follistatin domain, DAN and DAN-like proteins (R&D systems) comprising a DAN cysteine-knot domain, sclerostin/SOST (R&D systems), decorin (R&D systems), and alpha-2 macroglobulin (R&D systems).

Examples of BMP inhibitors for use in a method of the invention are Noggin, DAN, and DAN-like proteins including Cerberus and Gremlin (R&D systems). These diffusible proteins are able to bind a BMP ligand with varying degrees of affinity and inhibit their access to signalling receptors. The addition of any of these BMP inhibitors to the basal culture medium prevents the loss of stem cells.

A preferred BMP inhibitor is Noggin. Accordingly, in some embodiments, the culture medium as described herein comprises Noggin. In the context of a culture medium of the invention, Noggin is also referred to herein as "No". Noggin is preferably added to the basal culture medium at a concentration of at least 10 ng/ml, for example, at least 20 ng/ml, more preferred at least 25 ng/ml. A still more preferred concentration is about 25 ng/ml.

During culturing of stem cells, said BMP inhibitor may be added to the culture medium when required, for example, daily or every other day. The BMP inhibitor is preferably added to the culture medium every second day. The culture medium may be refreshed when required, for example, daily or every other day.

Wnt Agonists

The culture media of the invention may comprise one or more Wnt agonist. The Wnt signalling pathway is defined by a series of events that occur when the cell-surface Wnt receptor complex, comprising a Frizzled receptor, LRP and LGR is activated, usually be an extracellular signalling molecule, such as a member of the Wnt family. This results in the activation of Dishevelled family proteins which inhibit a complex of proteins that includes axin, GSK-3, and the protein APC to degrade intracellular β-catenin. The resulting enriched nuclear β-catenin enhances transcription by TCF/LEF family transcription factors.

A Wnt agonist is defined as an agent that activates TCF/LEF-mediated transcription in a cell. Wnt agonists are therefore selected from true Wnt agonists that bind and activate the Wnt receptor complex including any and all of the Wnt family proteins, an inhibitor of intracellular β-catenin degradation, a GSK inhibitor (such as CHIR9901) and activators of TCF/LEF.

In some embodiments, a Wnt agonist is a secreted glycoprotein including Wnt-1/Int-1, Wnt-2/Irp (InM-related Protein), Wnt-2b/13, Wnt-3/Int-4, Wnt-3a (R&D systems), Wnt-4, Wnt-5a, Wnt-5b, Wnt-6 (Kirikoshi H et al 2001 Biochem Biophys Res Com 283 798-805), Wnt-7a (R&D systems), Wnt-7b, Wnt-8a/8d, Wnt-8b, Wnt-9a/14, Wnt-9b/14b/15, Wnt-10a, Wnt-10b/12, WnM 1, and Wnt-16. An overview of human Wnt proteins is provided in "THE WNT FAMILY OF SECRETED PROTEINS", R&D Systems Catalog, 2004. In some embodiments, the Wnt agonist is an inhibitor of RNF43 or ZNRF3. It has been shown that RNF43 and ZNRF3 reside in the cell membrane and negatively regulate levels of the Wnt receptor complex in the membrane, probably by ubiquitination of Frizzled. Therefore, the inventors hypothesise that inhibition of RNF43 or ZNRF3 with antagonistic antibodies, RNAi or small molecule inhibitors would indirectly stimulate the Wnt pathway. RNF43 and ZNRF3 have a catalytic ring domain (with ubiquitination activity), which can be targeted in small molecule inhibitor design. Several anti-RNF43 antibodies and several anti-ZNRF3 antibodies are available commercially. In some embodiments, such antibodies are suitable Wnt agonists in the context of the invention.

In a preferred embodiment, the Wnt agonist in the culture medium is any agonist able to stimulate the Wnt pathway via the Lgr5 cell surface receptor, i.e. in a preferred embodiment, the Wnt agonist in the culture medium is an Lgr5 agonist. Known Lgr5 agonists include Rspondin, fragments and derivatives thereof, and anti-Lgr5 antibodies (e.g. see WO 2012/140274 and De Lau, W. et al. Nature, 2011 Jul. 4; 476(7360):293-7). A preferred Lgr5 agonist is Rspondin. Any suitable Rspondin may be used, for example, it may be selected from one or more of Rspondin 1, Rspondin 2, Rspondin 3 and Rspondin 4 or derivatives thereof. For example, any of Rspondin 1 (NU206, Nuvelo, San Carlos, Calif.), Rspondin 2 ((R&D systems), Rspondin 3, and Rspondin 4) may be used. Rspondin 1, 2, 3, and 4 are also referred to herein as "Rspondin 1-4". Fragments of Rspondin may be used as the Wnt agonist. For example, in some embodiments the Wnt agonist is a fragment of Rspondin comprising or consisting of the furin domain. Examples of suitable Rspondin fragments are represented by the sequence of amino acids recited in SEQ ID NO: 28, SEQ ID NO: 29, SEQ ID NO: 30 or SEQ ID NO: 31 or of sequences with more than 70, 80, 90 or 99% identity to any one of SEQ ID NO: 28, SEQ ID NO: 29, SEQ ID NO: 30 or SEQ ID NO: 31. In some embodiments the Lgr5 agonist is an anti-Lgr5 antibody, more preferably an agonistic anti-Lgr5 antibody. An example of an agonistic anti-Lgr5 antibody is 1D9 (available commercially from BD Biosciences, BDB562733, No.: 562733). Therefore, in one embodiment, the agonist is the antibody 1D9. The VL of antibody 1D9 is represented by SEQ ID NO: 32 and the VH is represented by SEQ ID NO: 33. Therefore, in one embodiment, the agonist is an antibody comprising or consisting of SEQ ID NO: 32 and/or SEQ ID NO: 33.

In some embodiments, the Wnt agonist in the culture medium is any agonist able to stimulate the Wnt pathway via the Lgr4 cell surface receptor, i.e. in some embodiments, the Wnt agonist in the culture medium is an Lgr4 agonist.

In some embodiments, the Wnt agonist in the culture medium is any agonist able to stimulate the Wnt pathway via the Lgr6 cell surface receptor, i.e. in some embodiments, the Wnt agonist in the culture medium is an Lgr6 agonist.

The Wnt agonist may be added to the media in an amount effective to stimulate a Wnt activity in a cell by at least 10%, more preferred at least 20%, more preferred at least 30%, more preferred at least 50%, more preferred at least 70%, more preferred at least 90%, more preferred at least 100%, relative to a level of said Wnt activity in the absence of said molecule, as assessed in the same cell type. As is known to a skilled person, Wnt activity can be determined by measuring the transcriptional activity of Wnt, for example by pTOPFLASH and pFOPFLASH Tcf luciferase reporter constructs (Korinek et al., 1997. Science 275:1784-1787).

A soluble Wnt agonist, such as Wnt-3a, may be provided in the form of Wnt conditioned media. For example, about 10% to about 30%, e.g. about 10 ng/ml to about 10 µg/ml, preferably about 1 µg/ml, Wnt conditioned media may be used.

Rspondin 1-4 may be provided in the form of Rspo conditioned media. For example, about 10% to about 30%, e.g. about 10 ng/ml to about 10 µg/ml, preferably about 1 µg/ml, Rspo conditioned media may be used.

One or more, for example, 2, 3, 4 or more Wnt agonists may be used in the culture medium. In one embodiment, the culture medium comprises an Lgr5 agonist, for example Rspondin, and additionally comprises a further Wnt agonist. In this context, the further Wnt agonist may, for example, be selected from the group consisting of Wnt-3a, a GSK-inhibitor (such as CHIR99021), Wnt-5, Wnt-6a and Norrin. In one embodiment, the culture medium comprises Rspondin and additionally comprises a soluble Wnt ligand, such as Wnt3a. Addition of a soluble Wnt ligand has been shown to be particularly advantageous for expansion of human epithelial stem cells (as described in WO2012/168930).

Any suitable concentration of Wnt agonist, e.g. Rspondin, may be used, for example, at least 200 ng/ml, more preferred at least 300 ng/ml, more preferred at least 500 ng/ml. A still more preferred concentration of Rspondin is at least 500 ng/ml or about 1 µg/ml.

During culturing of stem cells, said Wnt agonist may be added to the culture medium when required, for example, daily or every other day. The Wnt agonist is preferably added to the culture medium every second day.

Antibodies

Antibodies, such as anti-ErbB3/4 antibodies, agonistic anti-Lgr5 antibodies or antagonistic TGF-beta inhibitors (see below), used in the invention may be any antibodies, fragments, etc. A conventional antibody is comprised of two identical heavy chains and two identical light chains that are joined by disulfide bonds. Each heavy and light chain contains a constant region and a variable region. Each variable region contains three CDRs which are primarily responsible for binding an epitope of an antigen. They are referred to as CDR1, CDR2, and CDR3, numbered sequentially from the N-terminus, of which the CDR3 region comprises the most variable region and normally provides a substantial part of the contact residues to a target. The more highly conserved portions of the variable regions are called the "framework regions".

The term antibody is used herein in the broadest sense and specifically covers, but is not limited to, monoclonal antibodies (including full length monoclonal antibodies) of any isotype such as IgG, IgM, IgA, IgD and IgE, polyclonal antibodies including recombinant polyclonal antibodies, Oligoclonics, multispecific antibodies, chimeric antibodies, nanobodies, diabodies, BiTE's, Tandabs, mimetobodies, bispecific antibodies, humanized antibodies, human antibodies, deimmunised antibodies and antibody fragments. In addition, scaffolds will be covered under this term, such as Anticalins, Ankarins, etc. An antibody reactive with a the specific epitopes of the Lgr proteins discussed above can be generated by recombinant methods such as selection of libraries of recombinant antibodies in phage or similar vectors, or by immunizing an animal with the Lgr epitopes of nucleic acid encoding them.

In one embodiment, an antibody according to the invention comprises a single domain antibody, a F(ab')2, Fab, Fab', or single chain Fv (scFv) fragment. An Fc fragment, which for example activates complement and may bind to Fc receptors, can be present but is not required for an antibody and variants or derivatives thereof. A scFv fragment is an epitope-binding fragment that contains at least one fragment of an antibody heavy chain variable region (VH) linked to at least one fragment of an antibody light chain variable region (VL). The linker may be a short, flexible peptide selected to assure that the proper three-dimensional folding of the VL and VH regions occurs once they are linked so as to maintain the target molecule binding-specificity of the whole antibody from which the single-chain antibody fragment is derived. The carboxyl terminus of the VL or VH sequence may be covalently linked by a linker to the amino acid terminus of a complementary VL or VH sequence.

The antibody may be a diabody, mimetibody, nanobody, and/or a bispecific antibody. A nanobody is a single domain antibody that occurs naturally in camelids. In contrast to standard antibodies, nanobodies are relatively simple proteins comprising only a heavy chain-like variable region. Bispecific antibodies are artificially engineered monoclonal antibodies that consist of two distinct binding sites and are capable of binding two different epitopes. Examples of bispecific antibodies are discussed in more detail below in the section on dual-targeting and multi-targeting agonists.

The antibody may be a chimeric antibody comprising a binding portion, for example the variable region or part thereof of the heavy and light chains, of a non-human antibody, while the remainder portion, for example the constant region of the heavy and light chains, is of a human antibody. A chimeric antibody may be produced by recombinant processes well known in the art, and has an animal variable region and a human constant region.

The antibody may be a human antibody or a humanized antibody. The term "human antibody" means an antibody in which the variable and constant domain sequences are derived from human sequences. In a humanized antibody, only the complementarity determining regions (CDRs), which are responsible for antigen binding and specificity are animal derived and have an amino acid sequence corresponding to the animal antibody, and substantially all of the remaining portions of the molecule (except, in some cases, small portions of the framework regions within the variable region) are human derived and correspond in amino acid sequence to a human antibody. Methods for humanizing non-human antibodies are known in the art. As is known to the skilled person, antibodies such as rat antibodies can be humanized by grafting their CDRs onto the variable light (VL) and variable heavy (VH) frameworks of human Ig molecules, while retaining those rat framework residues deemed essential for specificity and affinity. Overall, CDR grafted antibodies consist of more than 80% human amino acid sequences.

In some embodiments, the antibody is a deimmunised antibody in which the T and B cell epitopes have been eliminated. They have reduced immunogenicity when applied in vivo.

TGF-Beta Inhibitor

The culture media of the invention may comprise a TGF-beta inhibitor. The presence of a TGF-beta inhibitor in the media is advantageous because it increases human organoid formation efficiency. TGF-beta signalling is involved in many cellular functions, including cell growth, cell fate and apoptosis. Signalling typically begins with binding of a TGF-beta superfamily ligand to a type II receptor which recruits and phosphorylates a type I receptor. The type I receptor then phosphorylates SMADs, which act as transcription factors in the nucleus and regulate target gene expression.

The TGF-beta superfamily ligands comprise bone morphogenic proteins (BMPs), growth and differentiation factors (GDFs), anti-müllerian hormone (AMH), activin, nodal and TGF-betas. In general, Smad2 and Smad3 are phosphorylated by the ALK4, 5 and 7 receptors in the TGF-beta/activin pathway. By contrast, Smad1, Smad5 and Smad8 are phosphorylated as part of the bone morphogenetic protein (BMP) pathway. Although there is some cross-over between pathways, in the context of this invention, a "TGF-beta inhibitor" or an "inhibitor of TGF-beta signalling" is preferably an inhibitor of the TGF-beta pathway which acts via Smad2 and Smad3. Therefore, in some embodiments the TGF-beta inhibitor is not a BMP inhibitor, e.g. the TGF-beta inhibitor is not Noggin. In some embodiments, a BMP inhibitor is added to the culture medium in addition to the TGF-beta inhibitor (see above).

Thus the TGF-beta inhibitor may be any agent that reduces the activity of the TGF-beta signalling pathway, preferably the signalling pathway that acts via Smad2 and/or Smad3, more preferably the signalling pathway that acts via ALK4, ALK5 or ALK7. There are many ways of disrupting the TGF-beta signaling pathway that are known in the art and that can be used in conjunction with this invention. For example, the TGF-beta signaling may be disrupted by: inhibition of TGF-beta expression by a small-interfering RNA strategy; inhibition of furin (a TGF-beta activating protease); inhibition of the pathway by physiological inhibitors; neutralisation of TGF-beta with a monoclonal antibody; inhibition with small-molecule inhibitors of TGF-beta receptor kinase 1 (also known as activin receptor-like kinase, ALK5), ALK4, ALK6, ALK7 or other TGF-beta-related receptor kinases; inhibition of Smad 2 and Smad 3 signaling e.g. by overexpression of their physiological inhibitor, Smad 7, or by using thioredoxin as an Smad anchor disabling Smad from activation (Fuchs, O. Inhibition of TGF-Signaling for the Treatment of Tumor Metastasis and Fibrotic Diseases. Current Signal Transduction Therapy, Volume 6, Number 1, January 2011, pp. 29-43(15)).

Various methods for determining if a substance is a TGF-beta inhibitor are known and might be used in conjunction with the invention. For example, a cellular assay may be used in which cells are stably transfected with a reporter construct comprising the human PAI-1 promoter or Smad binding sites, driving a luciferase reporter gene. Inhibition of luciferase activity relative to control groups can be used as a measure of compound activity (De Gouville et al., Br J Pharmacol. 2005 May; 145(2): 166-177).

A TGF-beta inhibitor according to the present invention may be a protein, peptide, small-molecules, small-interfering RNA, antisense oligonucleotide, aptamer or antibody. The inhibitor may be naturally occurring or synthetic. In one embodiment, the TGF-beta inhibitor is an inhibitor of ALK4, ALK5 and/or ALK7. For example, the TGF-beta inhibitor may bind to and directly inhibit ALK4, ALK5 and/or ALK7. Examples of preferred small-molecule TGF-beta inhibitors that can be used in the context of this invention include the small molecule inhibitors listed in Table 1:

TABLE 1

Small-molecule TGF-beta inhibitors targeting receptor kinases

| Inhibitor | Targets | IC50 (nM) | Mol Wt | Name | Formula |
|---|---|---|---|---|---|
| A83-01 | ALK5 (TGF-βR1) | 12 | 421.52 | 3-(6-Methyl-2-pyridinyl)-N-phenyl-4-(4-quinolinyl)-1H-pyrazole-1-carbothioamide | C25H19N5S |
|  | ALK4 | 45 |  |  |  |
|  | ALK7 | 7.5 |  |  |  |
| SB-431542 | ALK5 ALK4 ALK7 | 94 | 384.39 | 4-[4-(1,3-benzodioxol-5-yl)-5-(2-pyridinyl)-1H-imidazol-2-yl]benzamide | C22H16N4O3 |
| SB-505124 | ALK5 ALK4 | 47 129 | 335.4 | 2-(5-benzo[1,3]dioxol-5-yl-2-tert-butyl-3Himidazol-4-yl)-6-methylpyridine hydrochloride hydrate | C20H21N3O2 |
| SB-525334 | ALK5 | 14.3 | 343.42 | 6-[2-(1,1-Dimethylethyl)-5-(6-methyl-2-pyridinyl)-1H-imidazol-4-yl]quinoxaline | C21H21N5 |

TABLE 1-continued

Small-molecule TGF-beta inhibitors targeting receptor kinases

| Inhibitor | Targets | IC50 (nM) | Mol Wt | Name | Formula |
|---|---|---|---|---|---|
| SD-208 | ALK5 | 49 | 352.75 | 2-(5-Chloro-2-fluorophenyl)-4-[(4-pyridyl)amino]pteridine | C17H10ClFN6 |
| LY-36494 | TGR-βRI<br>TGF-βRII<br>MLK-7K | 59<br>400<br>1400 | 272.31 | 4-[3-(2-Pyridinyl)-1H-pyrazol-4-yl]-quinoline | C17H12N4 |
| SJN-2511 | ALK5 | 23 | 287.32 | 2-(3-(6-Methylpyridine-2-yl)-1H-pyrazol-4-yl)-1,5-naphthyridine | C17H13N5 |

In some embodiments, the TGF-beta inhibitor is a small molecule inhibitor optionally selected from the group consisting of: A83-01, SB-431542, SB-505124, SB-525334, LY 364947, SD-208 and SJN 2511.

In some embodiments, no more than one TGF beta inhibitor is present in the medium. In other embodiments, more than one TGF beta inhibitor is present in the medium, e.g. 2, 3, 4 or more. In some embodiments, a medium of the invention comprises one or more of any of the inhibitors listed in table 1. A medium may comprise any combination of one inhibitor with another inhibitor listed. For example, a medium may comprise SB-525334 or SD-208 or A83-01; or SD-208 and A83-01. The skilled person will appreciate that a number of other small-molecule inhibitors exist that are primarily designed to target other kinases, but at high concentrations may also inhibit TGF-beta receptor kinases. For example, SB-203580 is a p38 MAP kinase inhibitor that, at high concentrations (for example, approximate 10 µM or more) is thought to inhibit ALK5. Any such inhibitor that inhibits the TGF-beta signalling pathway can also be used in the context of this invention.

In some embodiments, the TGF beta inhibitor is present at at least 5 nM, for example, at least 50 nM, at least 100 nM, at least 300 nM, at least 450 nM, at least 475 nM, for example 5 nM-500 mM, 10 nM-100 mM, 50 nM-700 uM, 50 nM-10 uM, 100 nM-1000 nM, 350-650 nM or more preferably about 500 nM.

A83-01 may be added to the medium at a concentration of between 10 nM and 10 uM, or between 1 uM and 8 uM, or between 4 uM and 6 uM. For example, A83-01 may be added to the medium at about 5 uM. The skilled person would know how to determine the concentration of other TGF beta inhibitors for use in the invention.

Receptor Tyrosine Kinase Ligands

ErbB3/4 ligands are receptor tyrosine kinase ligands. The culture media of the invention may further comprise one or more additional receptor tyrosine kinase ligands that are not themselves ErbB3/4 ligands. An example of a receptor tyrosine kinase ligand for use in the invention is EGF, which is the ligand for the receptor tyrosine kinase EGFR. Many receptor tyrosine kinase ligands are also mitogenic growth factors.

The culture media of the invention may comprise one or more mitogenic growth factor. The one or more mitogenic growth factor may be selected from a family of growth factors comprising epidermal growth factor (EGF, Peprotech), Transforming Growth Factor-alpha (TGF-alpha, Peprotech), basic Fibroblast Growth Factor (bFGF, Peprotech), brain-derived neurotrophic factor (BDNF, R&D Systems), Platelet Derived Growth Factor (PDGF, Peprotech), amphiregulin (R&D Systems). A preferred PDGF is PDGF-CC. In the context of a culture medium of the invention, EGF is also referred to herein as "E" and FGF is also referred to herein as "F".

In some embodiments, the receptor tyrosine kinase ligand for use in the invention is one or more mitogenic growth factors selected from human EGF, human PDGF (e.g. human PDGF-CC), human amphiregulin and human TGF-alpha.

EGF

EGF is a potent mitogenic factor for a variety of cultured ectodermal and mesodermal cells and has a profound effect on the differentiation of specific cells in vivo and in vitro and of some fibroblasts in cell culture. The EGF precursor exists as a membrane-bound molecule which is proteolytically cleaved to generate the 53-amino acid peptide hormone that stimulates cells.

The inventors have found that EGF is not essential in the culture medium of the invention for the growth of breast organoids. Therefore, in some embodiments, the culture medium of the invention does not contain EGF. However, the inventors found that the addition of EGF may be beneficial for growth of breast organoids. Therefore, in some embodiments, the culture media of the invention further comprises EGF.

In embodiments where the culture medium of the invention comprises EGF, EGF is preferably added to the basal culture medium at a concentration of between 1 and 500 ng/ml or of at least 1 and not higher than 500 ng/ml. A preferred concentration is at least 1, 5, 10, 20, 25, 30, 40, 45, or 50 ng/ml and not higher than 500, 450, 400, 350, 300, 250, 200, 150, or 100 ng/ml. A more preferred concentration is at least 1 and not higher than 100 ng/ml. The same concentrations could be used for a different mitogenic growth factor, such as a PDGF or a FGF. If more than one FGF is used, for example FGF7 and FGF10, the concentration of a FGF is as defined above and refers to the total concentration of FGF used.

FGFR2b Ligands

FGF7 and FGF10 are proteins that belong to the fibroblast growth factor (FGF) family of proteins. FGF family members possess broad mitogenic and cell survival activities, and are involved in a variety of biological processes, including embryonic development, cell growth, morphogenesis, tissue repair, tumor growth and invasion. FGFs stimulate cells by interacting with cell surface tyrosine kinase receptors (FGFR). Four closely related receptors (FGFR1-FGFR4) have been identified. FGFR1-FGFR3 genes have been shown to encode multiple isoforms, and these isoforms can be critical in determining ligand specificity. Most FGFs bind more than one receptor (Ornitz J Biol Chem. 1998 Feb. 27; 273 (9):5349-57). However, FGF10 and FGF7 are unique among FGFs in that they interact only with a specific isoform of FGFR2, designated FGFR2b which is expressed exclusively by epithelial cells (Igarashi, J Biol Chem. 1998 273(21):13230-5).

In preferred embodiments, the culture medium of the invention comprises a ligand of FGFR2b (e.g. FGF1, FGF3, FGF7, FGF10 or FGF22). In some embodiments, the ligand of FGFR2b is a high-affinity ligand of FGFR2b. In some embodiments, the ligand of FGFR2b binds to FGFR2b but does not bind to any other FGFR isoforms. In some embodiments, the FGFR2b ligand is a member of the FGF7 subfamily (e.g. FGF7, FGF10 or FGF22). In a preferred embodiment, the FGFR2b ligand is FGF10 and/or FGF7. In some embodiments, no more than one FGFR2b ligand is used. In other embodiments, two or more FGFR2b ligands are used, e.g. 2, 3 or more. In some embodiments, the culture medium comprises FGF7 and FGF10. In some embodiments, biologically active fragments or variants of naturally occurring FGFR2b ligands, for example, biologically active fragments or variants of FGF7 and/or FGF10 are used as FGFR2b ligands. In some embodiments, biologically active synthetic ligands are used as FGFR2b ligands in the culture medium of the invention. "Biologically active" as used in this context means that the FGFR2b ligand, for example, the fragment or variant of a naturally occurring FGFR2b ligand, or a synthetic FGFR2b ligand, is capable of binding to FGFR2b and eliciting similar downstream signalling compared to FGF7 and/or FGF10, for example eliciting tyrosine phosphorylation of FRS2α (FGF receptor substrate 2α) or FRS2β (FGF receptor substrate 2β). Tyrosine phosphorylation of FRS2α and/or FRS2β is the earliest cytosolic event in the signalling pathways activated by FGF7 and/or FGF10. In some embodiments, the FGFR2b ligand is substituted with a compound that activates the FGFR2 or FGFR4 pathway (a "FGF-pathway activator").

In some embodiments, the one or more FGFR2b ligands used in the culture medium of the invention is selected from the following: human FGF7, human FGF10, human FGF22, human FGF1 or human FGF22.

In a further embodiment, a combination of mitogenic growth factors such as, for example, EGF and FGF7, or EGF and FGF10, is added to the basal culture medium. In a further preferred embodiment, a combination of mitogenic growth factors such as, for example, (i) FGF7 and FGF10, (ii) EGF, FGF7 and FGF10, or (iii) PDGF, FGF7 and FGF10, or (iv) EGF, PDGF, amphiregulin, FGF7 and FGF10 is added to the culture medium.

In some embodiments, TGF-alpha or amphiregulin are added to the basal culture medium. These mitogenic growth factors may replace EGF. In some embodiments, hepatocyte growth factor (HGF) is added to the culture medium.

During culturing of stem cells, a combination of receptor tyrosine kinase ligands (e.g. EGF, FGF10 and FGF7) is preferably added to the culture medium when required, for example, daily or every other day. They may be added singularly or in combination. It is preferable that they are added every second day.

ROCK Inhibitors

ROCK inhibitors, such as Y-27632 (10 μM; Sigma), can be included in any of the media described, in particular in the first few days of culture before performing cell sorting experiments, because it is known to avoid anoikis (a form of programmed cell death which is induced by anchorage-dependent cells detaching from the surrounding extracellular matrix). Therefore, any of the media defined herein, may additionally comprise a ROCK inhibitor for the first few days. In some embodiments, the culture medium of the invention additionally comprises a ROCK inhibitor, such as Y-27632, for example for the first few days of culture before performing cell sorting experiments.

A further embodiment a culture medium of the invention comprises a Rock (Rho-kinase) inhibitor. The addition of a Rock inhibitor was found to prevent anoikis, especially when culturing single stem cells. Said Rock inhibitor is preferably selected from R-(+)-trans-4-(1-aminoethyl)-N-(4-Pyridyl)cyclohexanecarboxamide dihydrochloride monohydrate (Y-27632, Sigma-Aldrich), 5-(1,4-diazepan-1-ylsulfonyl)isoquinoline (fasudil or HA1077, Cayman Chemical), and (S)-(+)-2-methyl-1-[(4-methyl-5-isoquinolinyl)sulfonyl]-hexahydro-1H-1,4-diazepine dihydrochloride (H-1 152, Tocris Bioschience). Said Rho-kinase inhibitor, for example Y-27632, is preferably added to the culture medium every second day during the first seven days of culturing said stem cells. A Rock inhibitor is preferably included in the medium in the first few days e.g. for the first 1, 2, 3, 4, 5, 6 or 7 days of culture after single cell seeding or after a split. Any suitable concentration of the Rock inhibitor may be used, for example, 1-200 uM, 1-100 uM, 5-50 uM or approximately 10 uM. A preferred concentration for Y27632 is 10 uM. Therefore, in some embodiments, the invention provides a method for culturing stem cells and/or a method for obtaining an organoid wherein a Rock inhibitor is added to the culture medium for the first 1, 2, 3, 4, 5, 6 or 7 days, optionally every second day. In some embodiments, the Rock inhibitor is not added to the culture medium after the first 2, 3, 4, 5, 6, 7, 8, 9 or 10 days.

Addition of a Rock inhibitor is particularly important when culturing single stem cells (as mentioned above), i.e. when the starting material for an organoid is a single stem cell. Therefore, in some embodiments the invention provides a method for obtaining an organoid, wherein the method comprises culturing stem cells, optionally single stem cells, wherein a Rock inhibitor is added to the culture medium for the first 1, 2, 3, 4, 5, 6 or 7 days, optionally every second day, and optionally not adding the Rock inhibitor to the culture medium after the first 2, 3, 4, 5, 6, 7, 8, 9 or 10 days.

The Rock inhibitor is less important, and sometimes not necessary, when culturing multiple cells, for example when the starting material for an organoid is a tissue fragment. Therefore, in some embodiments, the invention provides a method for obtaining an organoid, wherein the method comprises culturing stem cells, optionally a tissue fragment, wherein the Rock inhibitor is not added to the culture medium either at all or after the first 2, 3, 4, 5, 6, 7, 8, 9 or 10 days.

After the cells are split into multiple cultures, a Rock inhibitor may be added to the culture medium in the same way, meaning for the first 1, 2, 3, 4, 5, 6 or 7 days, optionally every second day, after the split, particularly when the split involves taking single stem cells from a first culture and placing these into a second culture. If the split involves taking multiple stem cells from the first culture and placing these into a second culture then addition of a Rock inhibitor is less important, and sometimes not necessary. Therefore, in some embodiments, wherein the method for obtaining organoids or for culturing stem cells involves a split, optionally where a single cell is involved in the split, a Rock inhibitor is added to the new culture medium for the first 1, 2, 3, 4, 5, 6 or 7 days, optionally every second day, after the split. In some embodiments, wherein the method for obtaining organoids or for culturing stem cells involves a split, optionally where multiple cells are involved in the split, is not added to the culture medium either at all or after the first 2, 3, 4, 5, 6, 7, 8, 9 or 10 days.

Notch Agonists

In yet a further embodiment, the culture medium of the invention further comprises a Notch agonist. Notch signaling has been shown to play an important role in cell-fate determination, as well as in cell survival and proliferation. Notch receptor proteins can interact with a number of surface-bound or secreted ligands, including but not limited to Delta 1, Jagged 1 and 2, and Delta-like 1, Delta-like 3, Delta-like 4. Upon ligand binding, Notch receptors are activated by serial cleavage events involving members of the ADAM protease family, as well as an intramembranous cleavage regulated by the gamma secretase presenilin. The result is a translocation of the intracellular domain of Notch to the nucleus where it transcriptionally activates downstream genes. A preferred Notch agonist is selected from Jagged 1 and Delta 1, or an active fragment or derivative thereof. A most preferred Notch agonist is DSL peptide (Dontu et al., 2004. Breast Cancer Res 6. R605-R615) with the sequence CDDYYYGFGCNKFCRPR. Said DSL peptide is preferably used at a concentration between 1004 and 100 nM or at least 1004 and not higher than 100 nM. The addition of a Notch agonist, especially during the first week of culturing, increases the culture efficiency by a factor of 2-3. Said Notch agonist is preferably added to the culture medium every second day during the first seven days of culturing said stem cells. Therefore, in some embodiments, the invention provides a method for culturing stem cells and/or a method for obtaining an organoid wherein a Notch agonist is added to the culture medium for the first 1, 2, 3, 4, 5, 6 or 7 days, optionally every second day. In some embodiments, the Notch agonist is not added to the culture medium after the first 2, 3, 4, 5, 6, 7, 8, 9 or 10 days.

A Notch agonist is defined as a molecule that stimulates a Notch activity in a cell by at least 10%, more preferred at least 20%, more preferred at least 30%, more preferred at least 50%, more preferred at least 70%, more preferred at least 90%, more preferred at least 100%, relative to a level of a Notch activity in the absence of said molecule. As is known to a skilled person, a Notch activity can be determined by measuring the transcriptional activity of Notch, for example by a 4xwtCBF1-luciferase reporter construct as described (Hsieh et al, 1996 Mol Cell. Biol. 16, 952-959).

Additional Components

The culture medium optionally comprises Nicotinamide and is preferably supplemented with one or more (e.g. 1, 2, 3 or all) of the compounds selected from the group consisting of B27, N-acetylcysteine and N2. Thus in some embodiments the culture medium further comprises one or more components selected from the group consisting of: nicotinamide, B27, N2 and N-Acetylcysteine. For example, in some embodiments, the culture medium further comprises B27, N-Acetylcysteine and Nicotinamide.

B27 (Invitrogen), N-Acetylcysteine (Sigma) and N2 (Invitrogen), and Nicotinamide (Sigma) are believed to control proliferation of the cells and assist with DNA stability. In the context of the invention, Nicotinamide is also referred to herein as "Nic".

In some embodiments, Nicotinamide is present at 7-15 mM, for example about 10 mM.

In some embodiments, the B27 supplement is 'B27 Supplement minus Vitamin A' (available from Invitrogen, Carlsbad, Calif.; www.invitrogen.com; currently catalog no. 12587010; and from PAA Laboratories GmbH, Pasching, Austria; www.paa.com; catalog no. F01-002; Brewer et al., J Neurosci Res., 35(5):567-76, 1993) may be used to formulate a culture medium that comprises biotin, cholesterol, linoleic acid, linolenic acid, progesterone, putrescine, retinyl acetate, sodium selenite, tri-iodothyronine (T3), DL-alpha tocopherol (vitamin E), albumin, insulin and transferrin.

The B27 Supplement supplied by PAA Laboratories GmbH comes as a liquid 50× concentrate, containing amongst other ingredients biotin, cholesterol, linoleic acid, linolenic acid, progesterone, putrescine, retinol, retinyl acetate, sodium selenite, tri-iodothyronine (T3), DL-alpha tocopherol (vitamin E), albumin, insulin and transferrin. Of these ingredients at least linolenic acid, retinol, retinyl acetate and tri-iodothyronine (T3) are nuclear hormone receptor agonists. B27 Supplement may be added to a culture medium as a concentrate or diluted before addition to a culture medium. It may be used at a 1× final concentration or at other final concentrations. Use of B27 Supplement is a convenient way to incorporate biotin, cholesterol, linoleic acid, linolenic acid, progesterone, putrescine, retinol, retinyl acetate, sodium selenite, tri-iodothyronine (T3), DL-alpha tocopherol (vitamin E), albumin, insulin and transferrin into a culture medium of the invention. It is also envisaged that some or all of these components may be added separately to the culture medium instead of using the B27 Supplement. Thus, the culture medium may comprise some or all of these components.

In some embodiments, retinoic acid is absent from the B27 Supplement used in the culture medium, and/or is absent from the culture medium.

N2 Supplement' is available from Invitrogen, Carlsbad, Calif.; www.invitrogen.com; catalog no. 17502-048; and from PAA Laboratories GmbH, Pasching, Austria; www.paa.com; catalog no. F005-004; Bottenstein & Sato, PNAS, 76(1):514-517, 1979. The N2 Supplement supplied by PAA Laboratories GmbH comes as a 100× liquid concentrate, containing 500 μg/ml human transferrin, 500 μg/ml bovine insulin, 0.63 μg/ml progesterone, 1611 μg/ml putrescine, and 0.52 μg/ml sodium selenite. N2 Supplement may be added to a culture medium as a concentrate or diluted before addition to a culture medium. It may be used at a 1× final concentration or at other final concentrations. Use of N2 Supplement is a convenient way to incorporate transferrin, insulin, progesterone, putrescine and sodium selenite into a culture medium of the invention. It is of course also envisaged that some or all of these components may be added separately to the culture medium instead of using the N2 Supplement. Thus, the culture medium may comprise some or all of these components.

In some embodiments in which the medium comprises B27, it does not also comprise N2. The embodiments of the present invention can therefore be adapted to exclude N2 when B27 is present, if desired.

In some embodiments N2 is not present in the culture medium.

In some embodiments in which the medium comprises N2, it does not also comprise B27. The embodiments of the present invention can therefore be adapted to exclude B27 when N2 is present, if desired.

In some embodiments B27 is not present in the culture medium.

In some embodiments the culture medium is supplemented with B27 and/or N2.

In some embodiments the basal medium is supplemented with 150 ng/ml to 250 ng/ml N-Acetylcysteine; preferably, the basal medium is supplemented with about 200 ng/ml N-Acetylcysteine.

In some embodiments the culture medium comprises progestin. In other embodiments the culture medium does not comprise progestin.

In some embodiments the culture medium comprises estradiol. In other embodiments the culture medium does not comprise estradiol.

In some embodiments the culture medium comprises hepatocyte growth factor. In other embodiments the culture medium does not comprise hepatocyte growth factor.

In some embodiments the culture medium comprises receptor activator of nuclear factor kappa-B ligand (RANKL). In other embodiments the culture medium does not comprise RANKL. In some embodiments, the culture medium of the invention is supplemented with nicotinamide. Addition of nicotinamide has been found to improve culture efficiency and lifespan of human organoids. Nicotinamide may be added to the culture medium to a final concentration of between 1 and 100 mM, between 5 and 50 mM, or preferably between 5 and 20 mM. For example, nicotinamide may be added to the culture medium to a final concentration of approximately 10 mM.

In some embodiments, the culture medium of the invention comprises a p53 stabilizing agent. A p53 stabilizing agent may be added to the culture medium in order to ensure that the cell population is predominantly tumour cells. Without wishing to be bound by any theory, it is believed that p53 stabilizing agents increase the cellular concentration of p53 (e.g. by blocking the interaction between p53 and Mdm2), stimulate p53-dependent expression and induce cellular senescence. p53 mutations commonly occur in tumour cells, which may result in the mutant p53 protein being unable to be stabilised by a p53 stabilizing agent. Thus, a subset of tumour cells with the mutant p53 protein would escape the senescence induced by a p53 stabilizing agent and outgrow normal cells in a mixed population. A preferred p53 stabilizing agent is a member of the Nutlin family, e.g. Nutlin-1, Nutlin-2 or Nutlin-3. For example, in some embodiments, the p53 stabilizing agent is Nutlin-3. Any suitable concentration of the p53 stabilizing agent may be used, for example between 1 nM and 10 mM, between 10 nM and 1 mM, between 100 nM and 100 µM, between 1 µM and 10 µM. For example, Nutlin-3 may be added to the culture medium of the invention to a final concentration of approximately 5 µM. Accordingly, in some embodiments of methods of the invention in which the breast epithelial stem cells are cancer cells, the culture medium used in the method advantageously comprises a p53 stabilizing agent. However, other embodiments of such methods for culturing breast epithelial cancer stem cells do not use a culture medium comprising a p53 stabilizing agent. It is also envisaged that the p53 stabilizing agent may be present in the culture medium when the method is used for culturing normal breast epithelial stem cells, although it is not required.

In some embodiments, the culture medium of the invention comprises a p38 MAP kinase inhibitor. A p38 MAP kinase inhibitor is an inhibitor that directly or indirectly negatively regulates p38 signalling. In some embodiments, the p38 MAP kinase inhibitor is SB202190.

However, other suitable p38 MAP kinase inhibitors may alternatively be used and these are readily available to the skilled person.

Any suitable pH may be used. For example, the pH of the medium may be in the range from about 7.0 to 7.8, in the range from about 7.2 to 7.6, or about 7.4. The pH may be maintained using a buffer. A suitable buffer can readily be selected by the skilled person. Buffers that may be used include carbonate buffers (e.g. $NaHCO_3$), and phosphates (e.g. $NaH_2PO_4$). These buffers are generally used at about 50 to about 500 mg/l. Other buffers such as N-[2-hydroxyethyl]-piperazine-N'-[2-ethanesul-phonic acid] (HEPES) and 3-[N-morpholino]-propanesulfonic acid (MOPS) may also be used, normally at around 1000 to around 10,000 mg/l. A culture medium may comprise a pH indicator, such as phenol red, to enable the pH status of the medium to be easily monitored (e.g. at about 5 to about 50 mg/litre).

A culture medium for use in the invention may comprise one or more amino acids. The skilled person understands the appropriate types and amounts of amino acids for use in stem cell culture media. Amino acids which may be present include L-alanine, L-arginine, L-asparagine, L-aspartic acid, L-cysteine, L-cystine, L-glutamic acid, L-glutamine, L-glycine, L-histidine, L-iso leucine, L-leucine, L-lysine, L-methionine, L-phenylalanine, L-proline, L-serine, L-threonine, L-tryptophan, L-tyrosine, L-valine and combinations thereof. Some culture media will contain all of these amino acids. Generally, each amino acid when present is present at about 0.001 to about 1 g/L of medium (usually at about 0.01 to about 0.15 g/L), except for L-glutamine which is present at about 0.05 to about 1 g/L (usually about 0.1 to about 0.75 g/L). The amino acids may be of synthetic origin.

A culture medium for use in the invention may comprise one or more vitamins. The skilled person understands the appropriate types and amounts of vitamins for use in stem cell culture media. Vitamins which may be present include thiamine (vitamin B1), riboflavin (vitamin B2), niacin (vitamin B3), D-calcium pantothenate (vitamin B5), pyridoxal/pyridoxamine/pyridoxine (vitamin B6), folic acid (vitamin B9), cyanocobalamin (vitamin B12), ascorbic acid (vitamin C), calciferol (vitamin D2), DL-alpha tocopherol (vitamin E), biotin (vitamin H) and menadione (vitamin K).

A culture medium for use in the invention may comprise one or more inorganic salts. The skilled person understands the appropriate types and amounts of inorganic salts for use in stem cell culture media. Inorganic salts are typically included in culture media to aid maintenance of the osmotic balance of the cells and to help regulate membrane potential. Inorganic salts which may be present include salts of calcium, copper, iron, magnesium, potassium, sodium, zinc. The salts are normally used in the form of chlorides, phosphates, sulphates, nitrates and bicarbonates. Specific salts that may be used include $CaCl_2$, $CuSO_4-5H_2O$, $Fe(NO_3)-9H_2O$, $FeSO_4-7H_2O$, $MgCl$, $MgSO_4$, $KCl$, $NaHCO_3$, $NaCl$, $Na_2HPO_4$, $Na_2HPO_4—H_2O$ and $ZnSO_4-7H_2O$.

The osmolarity of the medium may be in the range from about 200 to about 400 mOsm/kg, in the range from about 290 to about 350 mOsm/kg, or in the range from about 280 to about 310 mOsm/kg. The osmolarity of the medium may be less than about 300 mOsm/kg (e.g. about 280 mOsm/kg).

A culture medium for use in the invention may comprise a carbon energy source, in the form of one or more sugars. The skilled person understands the appropriate types and amounts of sugars to use in stem cell culture media. Sugars which may be present include glucose, galactose, maltose and fructose. The sugar is preferably glucose, particularly D-glucose (dextrose). A carbon energy source will normally be present at between about 1 and about 10 g/L.

A culture medium of the invention may contain serum. Serum obtained from any appropriate source may be used, including fetal bovine serum (FBS), goat serum or human serum. Preferably, human serum is used. Serum may be used at between about 1% and about 30% by volume of the medium, according to conventional techniques.

In other embodiments, a culture medium of the invention may contain a serum replacement. Various different serum replacement formulations are commercially available and are known to the skilled person. Where a serum replacement is used, it may be used at between about 1% and about 30% by volume of the medium, according to conventional techniques.

In other embodiments, a culture medium of the invention may be serum-free and/or serum replacement-free. A serum-free medium is one that contains no animal serum of any type. Serum-free media may be preferred to avoid possible xeno-contamination of the stem cells. A serum replacement-free medium is one that has not been supplemented with any commercial serum replacement formulation.

In a preferred embodiment, the cell culture medium is supplemented with a purified, natural, semi-synthetic and/or synthetic growth factor and does not comprise an undefined component, such as fetal bovine serum or fetal calf serum. For example, supplements such as B27 (Invitrogen), N-Acetylcysteine (Sigma) and N2 (Invitrogen) stimulate proliferation of some cells. In some embodiments, the cell culture medium is supplemented with one or more of these supplements, for example one, any two or all three of these supplements.

A culture medium for use in the invention may comprise one or more trace elements, such as ions of barium, bromium, cobalt, iodine, manganese, chromium, copper, nickel, selenium, vanadium, titanium, germanium, molybdenum, silicon, iron, fluorine, silver, rubidium, tin, zirconium, cadmium, zinc and/or aluminium.

The medium may comprise a reducing agent, such as beta-mercaptoethanol at a concentration of about 0.1 mM.

A culture medium of the invention may comprise one or more additional agents, such as nutrients or growth factors previously reported to improve stem cell culture, such as cholesterol/transferrin/albumin/insulin/progesterone, putrescine, selenite/other factors.

In some embodiments, the culture medium of the invention comprises recombinant human neuregulin β-1, an Rspondin (e.g. Rspondin 1), Noggin, B27, N-Acetylcysteine, Nicotinamide, a ROCK 1,2 inhibitor (for example, Y-27632), an ALK 4, 5, 7 inhibitor (for example, A83-01), a p38 MAP Kinase inhibitor (for example, SB 202190), FGF7 and FGF10.

In some embodiments, the culture medium of the invention comprises recombinant human neuregulin β-1, an Rspondin (e.g. Rspondin 1), Noggin, B27, N-Acetylcysteine, Nicotinamide, a ROCK 1,2 inhibitor (for example, Y-27632), an ALK 4, 5, 7 inhibitor (for example, A83-01), a p38 MAP Kinase inhibitor (for example, SB 202190), FGF7, FGF10 and PDGF-CC.

In some embodiments, the culture medium of the invention comprises recombinant human neuregulin β-1, an Rspondin (e.g. Rspondin 1), Noggin, B27, N-Acetylcysteine, Nicotinamide, a ROCK 1,2 inhibitor (for example, Y-27632), an ALK 4, 5, 7 inhibitor (for example, A83-01), a p38 MAP Kinase inhibitor (for example, SB 202190), FGF7, FGF10 and EGF.

In some embodiments, the culture medium of the invention comprises recombinant human neuregulin β-1, an Rspondin (e.g. Rspondin 1), Noggin, B27, N-Acetylcysteine, Nicotinamide, a ROCK 1,2 inhibitor (for example, Y-27632), an ALK 4, 5, 7 inhibitor (for example, A83-01), a p38 MAP Kinase inhibitor (for example, SB 202190), FGF7, FGF10, amphiregulin, TGF-alpha and EGF.

Extracellular Matrix

As described above, the method for culturing epithelial stem cells comprises culturing one or more epithelial stem cells in contact with an extracellular matrix. Any suitable extracellular matrix may be used. Isolated epithelial stem cells are preferably cultured in a microenvironment that mimics at least in part a cellular niche in which said stem cells naturally reside. This cellular niche may be mimicked by culturing said stem cells in the presence of biomaterials, such as an extracellular matrix that provides key regulatory signals controlling stem cell fate.

A cellular niche is in part determined by the stem cells and surrounding cells, and the extracellular matrix (ECM) that is produced by the cells in said niche. In a preferred method of the invention, epithelial stem cells are cultured in contact with an ECM. "In contact" means a physical or mechanical or chemical contact, which means that for separating said resulting organoid or population of epithelial stem cells from said extracellular matrix a force needs to be used. Preferably, the epithelial stem cells are embedded in the ECM.

A culture medium of the invention may be diffused into an extracellular matrix (ECM). In a preferred method of the invention, isolated tissue fragments or isolated epithelial stem cells are attached to an ECM. ECM is composed of a variety of polysaccharides, water, elastin, and glycoproteins, wherein the glycoproteins comprise collagen, entactin (nidogen), fibronectin, and laminin. ECM is secreted by epithelial cells, endothelial cells, parietal endoderm-like cells (e.g. Englebreth-Holm-Swarm Parietal Endoderm-Like cells described in Hayashi et al. (2004) Matrix Biology 23:47-62) and connective tissue cells. Different types of ECM are known, comprising different compositions including different types of glycoproteins and/or different combination of glycoproteins. Said ECM can be provided by culturing ECM-producing cells, such as for example epithelial cells, endothelial cells, parietal endoderm-like cells or fibroblast cells, in a receptacle, prior to the removal of these cells and the addition of isolated tissue fragments or isolated epithelial stem cells. Examples of extracellular matrix-producing cells are chondrocytes, producing mainly collagen and proteoglycans, fibroblast cells, producing mainly type IV collagen, laminin, interstitial procollagens, and fibronectin, and colonic myofibroblasts producing mainly collagens (type I, III, and V), chondroitin sulfate proteoglycan, hyaluronic acid, fibronectin, and tenascin-C. Alternatively, said ECM is commercially provided. Examples of commercially available extracellular matrices are extracellular matrix proteins (Invitrogen) and basement membrane preparations from Engelbreth-Holm-Swarm (EHS) mouse sarcoma cells (e.g. Cultrex® Basement Membrane Extract (Trevigen, Inc.) or Matrigel™ (BD Biosciences)). A synthetic extracellular matrix material, such as ProNectin (Sigma Z378666) may be used. Mixtures of extracellular matrix materials may be used, if desired. The use of an ECM for culturing stem cells enhanced long-term survival of the stem cells and the continued presence of undifferentiated stem cells. In the absence of an ECM, stem cell cultures could not be cultured for longer periods and no continued presence of undifferentiated stem cells was observed. In addition, the presence of an ECM allowed culturing of three-dimensional tissue organoids, which could not be cultured in the absence of an ECM. The extracellular matrix material will normally be a drop on the bottom of the dish in which cells are suspended. Typically, when the matrix solidifies at 37° C., the medium is added and diffuses into the ECM. The cells in the medium stick to the ECM by interaction with its surface structure, for example interaction with integrins.

An example of an ECM for use in a method of the invention comprises at least one glycoprotein, such as laminin.

A preferred ECM for use in a method of the invention comprises at least two distinct glycoproteins, such as two different types of collagen or a collagen and laminin. The ECM can be a synthetic hydrogel extracellular matrix or a naturally occurring ECM. A further preferred ECM comprises laminin, entactin, and collagen IV. A further preferred ECM is provided by Matrigel™ (BD Biosciences), which comprises laminin, entactin, and collagen IV. In some embodiments the extracellular matrix is a laminin-containing extracellular matrix such as Matrigel™ (BD Biosciences). In some embodiments, the ECM comprises laminin, entactin, collagen IV and heparin sulphate proteoglycan (e.g. Cultrex® Basement Membrane Extract Type 2 (Trevigen, Inc.)).

In some embodiments, the single stem cell, population of cells, or tissue fragment is embedded in matrigel, which is optionally growth factor reduced and/or phenol red-free.

In some embodiments, the culture medium is placed on top of the ECM. The culture medium can then be removed and replenished as and when required. In some embodiments, the culture medium is replenished every 1, 2, 3, 4, 5, 6 or 7 days. If components are "added" or "removed" from the media, then this can in some embodiments mean that the media itself is removed from the ECM and then a new media containing the "added" component or with the "removed" component excluded is placed on the ECM.

In some embodiments the culture medium of the invention is in contact with an extracellular matrix or a 3D matrix that mimics the extracellular matrix by its interaction with the cellular membrane proteins, such as integrins.

There is further provided a culture medium of the invention and an extracellular matrix, e.g. supplied as a kit.

In some embodiments, the culture medium of the invention is suitable for culturing adult breast stem cells. In some embodiments, the culture medium of the invention is suitable for obtaining breast organoids. In some embodiments, the culture medium of the invention is suitable for expanding a population of breast stem cells for at least 4, 5, 6, 7, 8, 9, 10, 11, 12, 13, 14 or more than 14 passages.

Thus, the invention provides a culture medium as described herein that comprises one or more ErbB3/4 ligands that is suitable for expanding a population of breast stem cells for at least 4, 5, 6, 7, 8, 9, 10, 11, 12, 13, 14 or more than 14 passages.

In some embodiments, the culture medium of the invention is suitable for establishing populations of successful breast organoids in at least 50%, at least 60%, at least 70%, at least 80% or at least 90% of inoculations. A successful breast organoid is defined herein as an organoid that is capable of being passaged at least four times.

Thus, the invention provides a culture medium that comprises one or more ErbB3/4 ligands that is suitable for establishing populations of successful organoids with an efficiency of at least 50%, at least 60%, at least 70%, at least 80% or at least 90%.

Uses of Culture Media of the Invention

The invention provides the use of the culture medium of the invention for expanding an epithelial stem cell, population of epithelial stem cells, tissue fragment or organoid.

The invention also provides the use of a culture medium of the invention for expanding a breast epithelial stem cell, population of breast epithelial stem cells, breast tissue fragment or breast organoid.

In some embodiments, the stem cell, population of stem cells, tissue fragment or organoid is obtainable from a normal tissue. For example, in some embodiments, the stem cell, population of stem cells, tissue fragment or organoid is obtainable from a non-cancerous tissue.

In some embodiments, the stem cell, population of stem cells, tissue fragment or organoid is obtainable from a diseased tissue, for example a cancerous tissue, such as from an adenoma, a fibroadenoma, an adenocarcinoma, a carcinoma, a sarcoma, circulating tumour cells or metastasized cancer. Accordingly, in some embodiments, the stem cell, population of stem cells, tissue fragment or organoid is obtainable from a benign or malignant breast tumour. In some embodiments, the stem cell, population of stem cells, tissue fragment or organoid is or comprises a breast cancer cell(s). In some embodiments, the stem cell, population of stem cells, or the tissue fragment is a biopsy from a breast tumour. The tumour is preferably a breast tumour by origin rather than being a metastatic tumour originating from a different tissue.

Isolation of Breast Epithelial Stem Cells for Culture

In a preferred embodiment, the epithelial stem cells to be cultured in the method of the invention and/or from which the organoids are derived are obtained from adult tissue, i.e. the epithelial stem cells are adult epithelial stem cells. In this context "adult" means mature tissue, i.e. includes newly-born baby or child but excludes embryonic or foetal. In a preferred embodiment the epithelial stem cells are not derived from embryonic stem cells or embryonic stem cell lines, e.g. which have been differentiated in vitro, for example human embryonic stem cells or human embryonic stem cell lines.

The cells and tissues are preferably mammalian cells and tissues. More preferably, the cells and tissues are human cells and tissues. In some embodiments they are from other mammals, for example from a laboratory animal (e.g. mouse, rabbit, rat, guinea pig), a companion animal (e.g. dog, cat, horse) or a farm animal (e.g. cow, pig, sheep, goat).

Cells taken directly from live tissue, i.e. freshly isolated cells, are also referred to as primary cells. In some embodiments the epithelial stem cells are primary epithelial stem cells. Primary cells represent the best experimental models for in vivo situations. In a preferred embodiment of the invention, the epithelial stem cells are (or are derived from) primary epithelial stem cells. Primary cell cultures can be passaged to form secondary cell cultures. With the exception of cancer cells, traditional secondary cell cultures have a limited lifespan. After a certain number of population doublings (e.g. 50-100 generations) cells undergo the process of senescence and stop dividing. Cells from secondary cultures can become immortalized to become continuous cell lines. Immortalization can occur spontaneously, or may be virally- or chemically-induced. Immortalized cell lines are also known as transformed cells. By contrast, the methods of the present invention allow continuous passaging of epithelial stem cells without immortalisation or transformation. Thus in some embodiments, the epithelial stem cells are not immortalised or transformed cells or are not derived from an immortalised cell line or a transformed cell line. An advantage of the present invention is that the epithelial stem cells, undergoing multiple rounds of expansion and passaging, retain the characteristics of primary cells and have minimal or no genotypic or phenotypic changes.

The epithelial stem cells may be obtained by any suitable method. In some embodiments, cells are isolated by collagenase digestion, for example, as described in the examples and in Dorell et al., 2008 (Hepatology. 2008 October;

48(4):1282-91. Surface markers for the murine oval cell response. Dorrell C, Erker L, Lanxon-Cookson K M, Abraham S L, Victoroff T, Ro S, Canaday P S, Streeter P R, Grompe M). In some embodiments, collagenase digestion is performed on a tissue biopsy. In some embodiments, collagenase and accutase digestion are used to obtain the epithelial stem cells for use in the invention.

In some embodiments, breast tissue may be minced, washed (for example in basal culture medium) and incubated in a culture medium of the invention supplemented with a protease (for example, collagenase, dispase or trypsin) (see, for example, Example 1). The protease may be at any suitable concentration, for example, between 0.1 and 10 mg/ml, between 0.1 and 1 mg/ml or between 1 and 10 mg/ml. For example, the protease may be present at between 1 and 2 mg/ml. Incubation in the culture medium supplemented with a protease may be for any suitable length of time. For example, the tissue may be incubated in the medium for between 10 minutes and 10 hours, between 20 minutes and 5 hours, between 30 minutes and 5 hours, between 30 minutes and 3 hours, between 30 minutes and 2 hours, between 1 hour and 5 hours, between 1 hour and 3 hours or between 1 hour and 2 hours. In some embodiments, the tissue is incubated in the medium for at least 10 minutes, at least 20 minutes, at least 30 minutes, at least 1 hour, at least 2 hours, at least 3 hours or at least 5 hours.

The tissue fragments contained in the resultant digested tissue suspension may then be further reduced in size. For example, the suspension may be sheared. Filtration and/or centrifugation steps may be used to isolate tissue fragments or isolated cells. The isolated tissue fragments or isolated cells may then be cultured in a culture medium of the invention.

In some embodiments, the method comprises culturing a fragment of tissue which comprises epithelium. In some embodiments, the epithelial stem cells are isolated from a tissue fragment.

In some embodiments, the epithelial stem cells are obtained for culturing based on the expression of epithelial cell surface markers, such as EPCAM, MUC-1, KRT-5, KRT8 and KRT18. A method of the invention therefore comprises preparing a cell suspension from said epithelial tissue as described above, contacting said cell suspension with an epithelial cell surface marker binding compound (e.g. EPCAM, MUC-1, KRT-5, KRT8 and/or KRT18 binding compounds), isolating the epithelial marker binding compound, and isolating the cells from said binding compound.

In some embodiments, epithelial stem cells are obtained for culturing based on the expression of Lgr5 and/or Lgr6 on the epithelial stem cell surface; these proteins belong to the large G protein-coupled receptor (GPCR) superfamily (see, for example, WO 2009/022907, the contents of which are incorporated herein in their entirety). The Lgr subfamily is unique in carrying a large leucine-rich ectodomain important for ligand binding. In some embodiments, a method of the invention therefore comprises preparing a cell suspension from said epithelial tissue as described above, contacting said cell suspension with an Lgr5 and/or 6 binding compound (such as an antibody, e.g. an anti-Lgr5 monoclonal antibody, e.g. as described in WO 2009/022907), isolating the Lgr5 and/or 6 binding compound, and isolating the stem cells from said binding compound.

An organoid is preferably obtained using a cell from an adult tissue, preferably an epithelial stem cell from an adult tissue.

In some embodiments the epithelial stem cells are normal cells. In alternative embodiments, the epithelial stem cells are cancer stem cells. Thus, it is envisaged, for example, that the stem cells may be Lgr5 positive cancer stem cells. Accordingly, the cells may be obtained from a tumour, if required. In alternative embodiments, the epithelial stem cells are diseased stem cells, for example stem cells infected with intracellular pathogens (e.g. bacteria, viruses or parasites).

Binding compounds that bind to breast cancer cell markers may be used for the isolation of breast cancer stem cells for culturing in a method of the invention. Examples of breast cancer cell markers include Epithelial Membrane Antigen, Cancer antigen 15-3 (CA 15-3), cancer antigen 27.29 (CA 27.29), carcinoembryonic antigen (CEA), Urokinase plasminogen activator (uPA), plasminogen activator inhibitor (PAI-1), Podocalyxin, EZH2 and kallikrein-10. For example, Epithelial Membrane Antigen (EMA) binding compounds (e.g. anti-EMA antibodies) may be used for the isolation of breast cancer cells. In some embodiments, a method of the invention therefore comprises preparing a cell suspension from primary or secondary cancerous tissue, contacting said cell suspension with a breast cancer cell marker binding compound (e.g. EMA binding compounds), isolating the breast cancer cell marker binding compound and isolating the cells from said binding compound. In another embodiment, an organoid originates from a single cell, optionally expressing Lgr5. In some embodiments the single cell comprises a nucleic acid construct comprising a nucleic acid molecule of interest.

Preferred Lgr5 and/or 6 binding compounds comprise antibodies, such as monoclonal antibodies that specifically recognize and bind to the extracellular domain of either Lgr5 or Lgr6, such as monoclonal antibodies including mouse and rat monoclonal antibodies (see, for example, WO 2010/016766, the contents of which are incorporated herein in their entirety). Using such an antibody, Lgr5 and/or Lgr6-expressing stem cells can be isolated, for example with the aid of magnetic beads or through fluorescence-activated cell sorting, as is clear to a skilled person. Using a method of the invention, it is possible to isolate one single Lgr5 and/or Lgr6 expressing cell and to apply a method of the invention to it. An organoid or a population of breast epithelial stem cells may therefore be derived from one single cell. Accordingly, in some embodiments, the starting cell to be cultured is a single cell.

Alternatively, a population of cells may be used as the starting point, for example, a population of cells contained in a breast tissue fragment as described above. Thus, the methods of the invention are not restricted to using single cells as the starting point.

In a further aspect, there is provided a method for obtaining an organoid comprising culturing breast epithelial stem cells in a culture medium of the invention. Preferably, the method comprises culturing the breast epithelial stem cells in a culture medium of the invention using a culture method as described herein.

In some embodiments, the method comprises culturing the epithelial stem cells or obtaining the organoid/population of adult epithelial stem cells from a single cell. Advantageously, this allows a homogenous population of cells to form. In some embodiments, the method comprises culturing the stem cells in a culture medium of the invention for a period of time, for example, 3 days to 10 weeks, 1 to 10 weeks, 1 to 4 weeks or 10 days to 3 weeks, and then passaging the cells (e.g. dissociating the cells to a single cell density, seeding one or more cells at a ratio of 1 cell per container (e.g. per well)), expanding the cells using a culture medium of the invention for a period of time, for example, 3 days to 10 weeks, 1 to 10 weeks, 1 to 4 weeks or 10 days to 3 weeks and repeating the passaging and expanding steps at least once, at least twice, at least three times, at least four times, at least five times, at least six times, at least seven times, at least eight times, at least nine times, at least ten times, at least eleven times, at least twelve times, at least thirteen times or at least fourteen times.

Following culturing, the method may further comprise obtaining and/or isolating one or more epithelial stem cells or an organoid. For example, following culture of the stem cells, it may be useful to remove one or more stem cells and/or one or more organoids cultured in the culture medium from the culture medium for use in subsequent applications. Any one of a number of physical methods of separation known in the art may be used to select the cells of the invention and distinguish these from other cell types. Such physical methods may involve FACS and various immuno-affinity methods based upon makers specifically expressed by the cells of the invention. As described herein, LGR5 is a cell marker that may be expressed in the cells of the invention. Therefore, by way of illustration only, the cells of the invention may be isolated by a number of physical methods of separation, which rely on the presence of this marker. Similarly, any of the other markers expressed by the cells may be used.

In one embodiment, the cells of the invention may be isolated by FACS utilizing an antibody, for example, against one of these markers. As will be apparent to one skilled in the art, this may be achieved through a fluorescent labeled antibody, or through a fluorescent labeled secondary antibody with binding specificity for the primary antibody. Examples of suitable fluorescent labels includes, but is not limited to, FITC, Alexa Fluor® 488, GFP, CFSE, CFDA-SE, DyLight 488, PE, PerCP, PE-Alexa Fluor® 700, PE-Cy5 (TRI-COLOR®), PE-Cy5.5, PI, PE-Alexa Fluor® 750, and PE-Cy7. This list is provided by way of example only, and is not intended to be limiting.

It will be apparent to a person skilled in the art that FACS analysis using an anti-Lgr5 antibody may provide a purified cell population. However, in some embodiments, it may be preferable to purify the cell population further by performing a further round of FACS analysis using one or more of the other identifiable markers, for example, Sox9, Slug, CD44 and/or ALDH1, but others may also be used.

In another embodiment, the cells of the invention may be isolated by immuno-affinity purification, which is a separation method well known in the art. By way of illustration only, the cells of the invention may be isolated by immuno-affinity purification directed towards c-kit. As will be apparent to one skilled in the art, this method relies upon the immobilisation of antibodies on a purification column. The cell sample is then loaded onto the column, allowing the appropriate cells to be bound by the antibodies, and therefore bound to the column. Following a washing step, the cells are eluted from the column using a competitor which binds preferentially to the immobilised anti-c-kit antibody, and permits the cells to be released from the column.

It will be apparent to a person skilled in the art that immuno-affinity purification using an immobilised antibody will provide a purified cell population. However, in some embodiments, it may be preferable to purify the cell population further by performing a further round of immuno-affinity purification using one or more of the other identifiable markers, for example Sox9, Slug, CD44 and/or ALDH1, and use an aliquot of the isolated clones to ascertain the expression of other relevant intracellular markers.

It will be apparent to a person skilled in the art that the sequential purification steps are not necessarily required to involve the same physical method of separation. Therefore, it will be clear that, for example, the cells may be purified through a FACS step using an anti-Lgr5 antibody, followed by an immuno-affinity purification step using a SSEA-1 affinity column. In certain embodiments, the cells may be cultured after isolation for at least about 15, at least about 20 days, at least about 25 days, or at least about 30 days. In certain aspects, the cells are expanded in culture longer to improve the homogeneity of the cell phenotype in the cell population.

Other features of this method are defined in the part of the description dedicated to definitions. Single-cell suspensions or small clusters of cells (2-50 cells/cluster) will normally be seeded, rather than large clusters of cells, as in known in the art. As they divide, such cells will be seeded onto a support at a density that promotes cell proliferation. Typically, when single cells are isolated the plating density of at least 1-500 cells/well is used, the surface of the well is 0.32 cm². When clusters are seeded the plating density is preferably 250-2500 cells/cm². For replating, a density of between about 2500 cells/cm² and about 5,000 cells/cm² may be used in some embodiments. During replating, single-cell suspensions or small cluster of cells will normally be seeded, rather than large clusters of cells, as in known in the art.

In one embodiment, the invention provides a population of cells or one or more organoids comprising said stem cells that have been generated or obtained by culturing stem cells or tissue fragments according to the invention, which have been cultured for at least 2 months, at least 3 months, preferably at least 4 months, at least 5 months, at least 6 months, at least 7 months, at least 9 months, or at least 12 months or more, wherein the stem cells have been passaged approximately every 1 to 4 weeks.

A 'population' of cells is any number of cells greater than 1, but is preferably at least $1\times10^3$ cells, at least $1\times10^4$ cells, at least $1\times10^5$ cells, at least $1\times10^6$ cells, at least $1\times10^7$ cells, at least $1\times10^8$ cells, or at least $1\times10^9$ cells.

The stem cells or progenitor cells of the invention cultured according to the invention may be human stem cells or human progenitor cells. The stem cells of the invention cultured according to the invention may be epithelial stem cells or epithelial progenitor cells.

In some embodiments, the stem cells of the invention and/or cultured according to the invention are not embryonic stem cells. In some embodiments the stem cells of the invention and/or cultured according to the invention are not human embryonic stem cells. Preferably, the stem cells of the invention are adult stem cells.

In a preferred embodiment, the stem cells are human breast epithelial stem cells. Human epithelial stem cells include stem cells of human epithelial tissue origin. Epithelial stem cells are able to form the distinct cell types of which the epithelium is composed.

In a preferred embodiment, the organoids are human breast organoids.

Methods and Culture Media for Cancer Cells and Cancer Organoids

In some embodiments, the epithelial stem cell is a cancer cell or a non-cancerous tumour cell e.g. is derived from a tumour. In some embodiments, the cancer cell is a circulating tumour cell. In some embodiments, the cancer cell is not a circulating tumour cell. Where the term "cancer" is used herein, it is to be understood that it applies equally to non-cancerous (benign) tumours. Accordingly, in some embodiments the cell is derived from a malignant tumour or from a metastasis. In some embodiments, the cell is derived from a benign tumour. Cancer cells tend to have mutations that constitutively activate or deactivate certain growth pathways and which mean that certain factors in the culture medium that may normally be required for growth, are no longer necessary. For example, some cancers result in constitutive activation of the Wnt pathway. In such cases, a culture medium may not require an Lgr5 agonist and/or may not require a Wnt agonist, but one or both of these may still be present in the culture medium. Other mutations would allow other factors to be left out of the culture media described herein. Other epithelial cancers (carcinomas) or non-cancerous tumours (e.g. adenomas) can also be grown in culture media of the invention.

In a preferred embodiment, a cancer organoid obtained from cancer stem cells is grown in a culture medium of the invention that is suitable for growth of the corresponding normal tissue organoid obtained from normal stem cells, optionally with certain factors excluded from the medium. For example, a breast cancer organoid obtained by culturing breast cancer stem cells may be grown in the same culture conditions as a normal breast organoid obtained by culturing breast epithelial stem cells, optionally with certain factors excluded from the medium. In many situations it may be preferable (or at least more convenient) to grow cancer organoids in the normal tissue medium (without any factors excluded). Preferably, the normal tissue medium should allow cancers with all genetic backgrounds to grow, without excluding any particular cancer mutations. The methods of the invention for culturing stem cells can be practised accordingly.

In a further preferred embodiment, the cancer organoid is grown in a culture medium of the invention that further comprises a p53 stabilizing agent. A p53 stabilizing agent may be added to the culture medium in order to ensure that the cell population is predominantly tumour cells. The methods of the invention for culturing stem cells can be practised accordingly.

Methods

The invention provides a method for culturing a single breast epithelial stem cell, a population of breast epithelial stem cells, or an isolated breast tissue fragment, preferably to generate an organoid, wherein the method comprises:
  providing a breast epithelial stem cell, a population of breast epithelial stem cells or an isolated breast tissue fragment;
  providing a culture medium comprising one or more ErbB3/4 ligands and preferably further comprising one or more FGFR2b ligands and/or one or more Wnt agonists;
  contacting the stem cell, population of stem cells, or isolated tissue fragment with the culture medium;
  culturing the stem cell, population of stem cells, or isolated tissue fragment under appropriate conditions.

The invention also provides a method for expanding breast epithelial stem cells, wherein the method comprises:
  providing a breast epithelial stem cell, population of breast epithelial stem cells or an isolated breast tissue fragment;
  providing a culture medium comprising one or more ErbB3/4 ligands and (i) one or more FGFR2b ligands and/or (ii) one or more Wnt agonists (e.g. one or more Lgr5 agonists);
  contacting the stem cell, population of stem cells, or isolated tissue fragment with the culture medium; and
  culturing the cells, population of stem cells, or isolated tissue fragment under appropriate conditions.

Preferably, the cells are expanded to generate one or more (e.g. at least 2, 3, 4, 5, 6, 10, 15, 20 or more than 20) organoids.

In some embodiments, the culture medium used in the methods of the invention is a culture medium according to the invention.

A method for 'expanding' a population of cells or isolated tissue fragments is one that involves maintaining or increasing the number of stem cells in an initial population to generate an expanded population of stem cells which retain their undifferentiated phenotype and self-renewing properties.

However, it may also include the production of differentiating progeny, which may, for example, form tissue-like structures contributing to organoid formation. Hence, there are herein provided methods for obtaining a breast organoid comprising culturing stem cells or tissue fragments comprising said stem cells in a culture medium of the invention. The invention provides a method for expanding a single breast stem cell or a population of breast stem cells, preferably to generate an organoid, wherein the method comprises culturing the single stem cell or population of stem cells in a culture medium according to the invention. As mentioned above, the organoid may be a normal organoid or it may be a cancer organoid, for example, a carcinoma organoid or an adenocarcinoma organoid, or a benign tumour organoid, for example. In some embodiments, the method for expanding a single stem cell or a population of stem cells, preferably to generate an organoid, comprises expanding the single stem cell, population of stem cells or tissue fragment in a culture medium according to the invention.

Thus the invention provides a method for expanding a single breast epithelial stem cell or a population of breast epithelial stem cells, preferably to generate an organoid, wherein the method comprises:
  providing a breast epithelial stem cell, a population of breast epithelial stem cells or an isolated breast tissue fragment;
  providing a culture medium according to the invention;
  contacting the stem cells with the culture medium;
  culturing the cells under appropriate conditions.

In some embodiments, the method comprises bringing the stem cell, the population of stem cells or the isolated tissue fragment and the culture medium into contact with an extracellular matrix or a 3D matrix as described herein, for example, a 3D matrix that mimics the extracellular matrix by its interaction with the cellular membrane proteins such as integrins, for example a laminin-containing extracellular matrix such as Matrigel™ (BD Biosciences) or Cultrex® Basement Membrane Extract (Trevigen, Inc.). In some embodiments, the culture medium is diffused into the extracellular matrix.

The invention provides methods for culturing breast epithelial stem cells. The invention further provides methods for expanding breast epithelial stem cells and methods for obtaining breast organoids.

The term "expanding stem cells" is synonymous with "obtaining breast organoids".

Isolation and Culture of Tissue Fragments and Stem Cells

The skilled person would be able to determine the appropriate culture conditions for the methods of the invention.

In some embodiments, the method comprises bringing the stem cell, the population of stem cells or the isolated tissue fragment and the culture medium into contact with an extracellular matrix or a 3D matrix as described herein, for example, a 3D matrix that mimics the extracellular matrix by its interaction with the cellular membrane proteins such as integrins, for example a laminin-containing extracellular matrix such as Cultrex® Basement Membrane Extract (Trevigen, Inc.) or Matrigel™ (BD Biosciences). In some embodiments, the culture medium is diffused into the extracellular matrix.

In some embodiments, the tissue fragments or isolated cells are cultured in suspension plates. In some embodiments, the tissue fragments or isolated cells are cultured at between 35° C. and 39° C. or between 36° C. and 38° C. For example, the tissue fragments or isolated cells may be cultured at approximately 37° C.

In some embodiments, the tissue fragments or isolated cells are cultured at ambient levels of $O_2$. Alternatively, in some embodiments the level of $O_2$ may be, for example, between 0.5% and 4%, between 1% and 4%, between 1% and 3% or between 2% and 4%. For example, the tissue fragments or isolated cells may be cultured under conditions of approximately 2% $O_2$. The tissue fragments or isolated cells may be cultured under conditions of between 3% and 7% $CO_2$ or between 4% and 6% $CO_2$. For example, the tissue fragments or isolated cells may be cultured under conditions of approximately 5% $CO_2$.

The culture medium may be changed at any suitable interval, for example, every 1-7 days, every 2-6 days or every 3-5 days. For example, the culture medium may be changed every 4 days.

Organoids may be passaged at any suitable interval, for example, every 3 days to every 10 weeks, every 1 to 10 weeks, every 1 to 4 weeks or every 10 days to 3 weeks. In some embodiments, the organoids are passaged approximately every 10 days to 3 weeks.

In some embodiments, the timing for passaging of organoids is determined by the organoids reaching a particular size (e.g. an average size of approximately 100-200 μm) and/or a reduction in viability which can manifest in the loss of integrity of the epithelium, the organoids having a dense appearance and/or the presence of dead cells.

Organoids

The invention provides an organoid or a population of epithelial stem cells obtainable or obtained by a method of the invention. Thus, in some embodiments, the method further comprises obtaining and/or isolating an organoid. The organoid or population of epithelial stem cells of the invention comprises breast cells. Accordingly, there is provided a breast organoid which comprises a population breast epithelial stem cells. Preferably, the organoid or population of epithelial stem cells of the invention consists of breast cells.

Methods of expanding breast cells are currently described in Pasic et al. (2011) Genes & Development 25:1641-1653, but the culture methods and resulting cellular structures are different from the culture methods and resulting cellular structures provided by the present invention. The methods described in Pasic et al. use a culture system which comprises (i) amphiregulin or EGF (which are HER1 ligands) and (ii) FGF2 or FGF7. They do not use culture media comprising an ErbB3/4 ligand in combination with an Lgr5 agonist or a FGFR2b ligand, as is used in the present invention. Pasic et al. tested a culture medium comprising an ErbB3/4 ligand, NRG1-β1, but did not find that the breast organoids are able to grow in this culture medium. Pasic et al. did not test a culture medium comprising an ErbB3/4 ligand combined with an Lgr5 agonist or a FGFR2b ligand. Use of the Pasic et al. culture system results in the formation of cellular structures that have a morphology that is distinct from that of the organoids of the present invention. In particular, the Pasic et al. cellular structures have a budding morphology in which the structures have a rough edge, whereas the organoids obtained using the methods of the present invention do not have this morphology but instead have a smooth cyst-like structure or a morphology that is similar to a cluster of grapes. Cultures using the Pasic et al. system have been observed to stop expanding after 2-3 passages (see Example 4 herein), whereas the inventors have found that in some embodiments using a method of the invention it is possible to expand the breast epithelial stem cells for more than 14 passages.

Methods of culturing circulating tumour cells are described in Yu et al. (2014) Science 345(6193):216-220. However, the authors of this paper provided no guidance with respect to culturing breast epithelial stem cells obtained from normal breast tissue, primary tumour or metastases. Again, the culture system is different from the present invention and results in different structures compared to the organoids of the present invention. In particular, Yu uses a culture method which comprises EGF and FGF2. They do not use culture media comprising an ErbB3/4 ligand in combination with an Lgr5 agonist or a FGFR2b ligand, as is used in the present invention. Indeed, they do not use any culture media comprising an ErbB3/4 ligand. Yu's method results in formation of aggregates of single tumour cells without strong intercellular adhesion. No continuous epithelium is formed using this method. In contrast, the organoids obtained using the methods of the present invention display intercellular adhesion and a continuous epithelium. In some embodiments, the intercellular adhesion is strong.

Accordingly, the invention provides a breast organoid which has a cyst-like structure. In some embodiments, the cyst-like structure comprises a central lumen. In some embodiments, the central lumen of the cyst-like structure does not comprise any cells. In other embodiments, the central lumen of the cyst-like structure comprises breast epithelial stem cells, optionally wherein the central lumen is filled with breast epithelial stem cells. The invention further provides a breast organoid that has a morphology that is similar to a cluster of grapes. The invention further provides a breast epithelial stem cell, a population of breast epithelial stem cells or a breast organoid that has been cultured or can be cultured for more than 3 passages. The invention further provides a culture medium comprising an ErbB3/4 ligand combined with an Lgr5 agonist and/or a FGFR2b ligand.

Organoids of the invention, obtainable by expansion of stem cells, provide a population of cells which resemble their in vivo counterparts.

In some embodiments, an organoid comprises at least one epithelial stem cell. The term "stem cell" preferably refers to a cell which can divide and produce further epithelial stem cells or can generate differentiated progeny, e.g. progenitor cells, which are able to divide and further differentiate into one or more cell types. However, in some embodiments, the term "stem cell" and "progenitor cell" may be used interchangeably. In some instances, a progenitor cell is able to dedifferentiate into a stem cell and so culturing a progenitor cell in the culture medium of the invention may result in the progenitor cell dedifferentiating into a stem cell. For example, it is to be understood that in a preferred organoid, the majority of cells are expanding cells (i.e. dividing cells) that retain an undifferentiated phenotype. Although some spontaneous differentiation may occur, the cell population is generally an expanding population. The epithelial stem cells used in the invention are preferably multipotent, oligopotent or unipotent organ-specific adult stem cells. The stem cells are not totipotent stem cells. In some embodiments, the stem cells are not pluripotent stem cells. The organoids also have a distinctive structure that arises from these cellular properties, as described in detail below.

Image analysis may be used to assess characteristics of cells in culture such as cell morphology; cell structures; evidence for apoptosis or cell lysis; and organoid composition and structure. Many types of imaging analysis are well known in the art, such as electron microscopy, confocal microscopy, stereomicroscopy, fluorescence microscopy. Histological analysis can reveal basic architecture and cell types.

An organoid of the invention preferably has a three dimensional structure, i.e. the organoid is preferably a three-dimensional organoid. In a preferred embodiment the organoid comprises only epithelial cells, i.e. non-epithelial cells are absent from the organoid. This is because the culture medium of the invention is specifically designed to expand epithelial stem cells, for example Lgr5+ epithelial stem cells. Therefore, even if other cell types are transiently present in the culture medium, e.g. in the tissue fragment that is the starting material of the invention, these cells are unlikely to survive and instead will be replaced by the longer term expansion of the stem cells which generate a pure population of epithelial cells.

In some embodiments, the epithelial cells surround a lumen. In some embodiments, the epithelial cells surrounding the lumen are polarized, (meaning that proteins are differentially expressed on the apical or basolateral side of the epithelial cell). In some embodiments the organoids comprise stem cells which are able to actively divide and which are preferably able to differentiate to all major differentiated cell lineages present in the corresponding in vivo tissue.

In some embodiments the organoids of the invention have a section which is formed of multiple layers. In some embodiments the organoids of the invention have a monolayer section which appears to be formed of multiple layers referred to herein as regions of "pseudo-stratified" cells. In some embodiments the monolayer of pseudo-stratified cells folds so that it encloses lumina between the folds.

In some embodiments the organoids of the invention comprise single monolayers that are folded (or invaginated) to form two or more layers. It can sometimes be difficult to distinguish between folded (or invaginated) monolayers and regions of stratified cells. In some embodiments an organoid comprises both regions of stratified cells and regions of folded monolayers. In some embodiments the organoids of the invention have a section which is formed of multiple layers and a section comprising a single monolayer of cells. In some embodiments the organoids of the invention comprise or consist of a single monolayer of cells.

In some embodiments the organoids of the invention comprise or consist of epithelial cells. In some embodiments, the organoids comprise or consist of a single layer of epithelial cells. In some embodiments non-epithelial cells are absent from the organoids.

Illustrative examples of organoids generated according to the invention are given in the accompanying figures. In one embodiment, an organoid of the invention has a structure essentially as presented in FIG. 2 (for example, in some embodiments, a normal organoid has a structure essentially as presented for the W894N or R1100N organoid lines in FIG. 2B or a cancer organoid has a structure essentially as presented for the W1007T, W1012T or W859T organoid lines in FIG. 2A) or in FIG. 6. In one embodiment, an organoid of the invention exhibits cell staining essentially as presented in FIG. 5 or FIG. 6.

In some embodiments, the organoids are mainly cystic structures with few budding structures. In some embodiments, the organoids generated according to the invention do not have budding structures. The cystic structures comprise mainly monolayers but some regions of stratified cells may be present.

By "cystic" it is meant that the organoid is approximately spherical. By "budding" it is meant that the organoid has multiple regions growing out of the basic structure.

Under the improved culture conditions of the invention, breast organoids displayed cystic organoid structures, rather than the budding structures seen under previous culture conditions.

The invention also provides an organoid, preferably obtainable by the methods of the invention, which is a three-dimensional organoid comprising epithelial cells surrounding a central lumen.

In some embodiments, said organoid comprises a single layer of cells. In other embodiments, said organoid comprises a multi-layered epithelium.

In some embodiments, the organoid is obtained from normal breast tissue and has a cystic structure. In some embodiments, said normal organoid comprises a monolayer of basal and luminal cells surrounding a central lumen.

In some embodiments, the organoid is obtained from cancerous breast tissue and has a cystic structure. In some embodiments, said organoid comprises: (i) a central lumen, multiple small lumina or no lumen and/or (ii) a monolayer of epithelial cells or a multi-layered epithelium. Thus, in some embodiments, the breast cancer organoid of the invention comprises a monolayer of epithelial cells surrounding a lumen. In other embodiments, the breast cancer organoid comprises a multi-layered epithelium and multiple small lumens. In further embodiments, the breast cancer organoid comprises a multi-layered epithelium and no lumen. Cancer breast organoids optionally comprise solid balls of tumour cells.

Tumour status of cancer cells or cancer organoids may be confirmed using any suitable method. For example, karyotyping of cells or organoids can be performed to assess whether aneuploidy is present, which would suggest that the cells or organoids are tumour cells or tumour organoids.

Tumour cells or cancer organoids may also be identified by adding a p53 stabilizing agent to the culture medium. Tumour cells and cancer organoids commonly contain p53 mutations that result in p53 stabilizing agents having no effect on the degradation of p53. Thus, tumour cells, unlike normal cells, are often able to escape senescence triggered by the addition of a p53 stabilizing agent (e.g. Nutlin-3) to a culture medium.

In some embodiments, the breast cancer organoids stain positively for luminal cell markers, e.g. keratin-8 (Krt-8), and stain negatively for basal cell markers, e.g. keratin-14 (Krt-14) or keratin-5 (Krt-5). Thus, in some embodiments, the breast cancer organoid comprises luminal cells but does not comprise basal cells. In some embodiments, breast cancer organoids express KRT-8 at levels that are comparable to those seen in normal breast tissue or non-cancerous breast organoids. In some embodiments, breast cancer organoids express KRT-5 and/or KRT-14 at levels that are reduced compared to those seen in normal breast tissue or non-cancerous breast organoids.

Breast cancer organoids of the invention may express levels of CDH1 that are reduced compared to those seen in normal breast tissue or non-cancerous breast organoids.

Markers of epithelial to mesenchymal transition (e.g. VIM, ZEB1) may be more highly expressed in breast cancer organoids compared to normal breast tissue or non-cancerous breast organoids. Breast cancer organoids may display a reduced level of E-cadherin expression compared to normal breast tissue or non-cancerous breast organoids.

Breast cancer organoids of the invention may express other breast cancer cell markers such as Epithelial Membrane Antigen, Cancer antigen 15-3 (CA 15-3), cancer antigen 27.29 (CA 27.29), carcinoembryonic antigen (CEA), Urokinase plasminogen activator (uPA), plasminogen activator inhibitor (PAI-1), Podocalyxin, EZH2 and/or kallikrein-10.

There is provided an organoid or a population of epithelial stem cells which has been cultured in culture media of the invention for at least 2 months, for example at least 10 weeks, at least 12 weeks, at least 14 weeks, at least 16 weeks, at least 4 months, at least 5 months, at least 6 months, at least 9 months, at least one year. Preferably, the cells are human cells. Preferably, the cells have been passaged approximately every 1 to 4 weeks.

There is also provided an organoid or a population of epithelial stem cells which has been that has been passaged or which is capable of being passaged for more than 3 passages, more than 4 passages, more than 5 passages, more than 6 passages, more than 7 passages, more than 8 passages, more than 9 passages, more than 10 passages, more than 11 passages, more than 12 passages, more than 13 passages or more than 14 passages.

Advantageously, use of a ErbB3/4 ligand allows the breast cells and organoids to be cultured long-term. It is not possible to culture and expand human breast epithelial stem cells or breast organoids for two months or more in the culture medium described in Pasic et al., WO2012/014076 or WO2012/168930, wherein the cells or organoids are passaged at least three times. Therefore, such breast organoids or populations of breast epithelial stem cells that had been cultured long-term did not exist before the present invention. Accordingly, there is provided an organoid or a population of stem cells that has been cultured/passaged or that is capable of being cultured/passaged as described herein.

Within the context of the invention, a tissue fragment is a part of an adult tissue, preferably a human adult tissue, such as part of a human breast. The tissue may be normal (healthy) tissue or it may be diseased or infected tissue. Preferably an organoid as identified herein is therefore not a tissue fragment. An organoid is preferably obtained using a cell from an adult tissue, preferably an epithelial stem cell from an adult tissue, optionally from an adult tissue fragment. In some embodiments, an organoid is obtained using an epithelial stem cell from an adult tissue or adult tissue fragment expressing Lgr5. Therefore, within the context of this invention, in some embodiments a tissue fragment comprises Lgr5+ stem cells.

In an embodiment, an organoid is an organoid which is still being cultured using a method of the invention (preferably using a culture medium of the invention) and is therefore in contact with an extracellular matrix. Preferably, an organoid is embedded in a non-mesenchymal extracellular matrix. Within the context of the invention, "in contact" means a physical or mechanical or chemical contact, which means that for separating said organoid from said extracellular matrix a force needs to be used. In some embodiments, the extracellular matrix is a gelatinous protein mixture secreted by Engelbreth-Holm-Swarm (EHS) mouse sarcoma cells, such as Matrigel (BD Biosciences) or Cultrex® Basement Membrane Extract (Trevigen, Inc.). Accordingly, the culture medium of the invention may optionally further comprise a population of cells of invention and/or one or more organoids of the invention.

The invention provides a composition comprising an organoid or cell of the invention, an extracellular matrix and a culture medium, preferably a culture medium of the invention.

Uses of Organoids

There is an interest in culture media and methods for culturing stem cells for the formation, maintenance and expansion of organoids, such as breast organoids. An organoid comprises stem cells, such as epithelial stem cells, which retain their undifferentiated phenotype and self-renewal properties but also have differentiating progeny that grow into tissue-like structures. Similarly to populations of related or identical cells, breast organoids, which more closely mimic the basic physiology of breast tissue, may be used in toxicity assays, or assays for drugs. They may also be useful for culturing pathogens which currently lack suitable tissue culture or animal models. Furthermore, such organoids may be useful in regenerative medicine, for example in post-radiation and/or post-surgery repair of the breast.

It is clear that there are many clinical and research applications for stem cells and their differentiated progeny. For all these applications, reproducible culture methods are of the utmost importance for providing adequate numbers of cells of suitable quality. For example, for effective drug screening, conditions must be carefully controlled requiring precise culture methods for controlling differentiation and proliferation of cells, so that pure populations of phenotypically and karyotypically identical cells can be generated. Similarly, for cell-based therapies, wherein cultured cells may be directly provided to patients, the cells must be genetically and phenotypically sound so as to avoid undesirable immune responses or cell fates when provided to the patient.

The invention provides the use of an organoid or expanded population of cells of the invention for use in medicine. Accordingly, the invention provides the use of an organoid or expanded population of cells of the invention for use in treating a disorder, condition or disease. The invention provides the use of an organoid or expanded population of cells of the invention for use in drug screening, (drug) target validation, (drug) target discovery, toxicology and toxicology screens, personalized medicine, regenerative medicine and/or as ex vivo cell/organ models, such as disease models.

Cells and organoids cultured according to the media and methods of the invention are thought to faithfully represent the in vivo situation. This is true both for expanded populations of cells and organoids grown from normal tissue and for expanded populations of cells and organoids grown from diseased tissue. Therefore, as well as providing normal ex vivo cell/organ models, the organoids or expanded population of cells of the invention can be used as ex vivo disease models.

Organoids of the invention can also be used for culturing of a pathogen and thus can be used as ex vivo infection models. Examples of pathogens that may be cultured using an organoid of the invention include viruses, bacteria, prions or fungi that cause disease in its animal host. Thus an organoid of the invention can be used as a disease model that represents an infected state. In some embodiments of the invention, the organoids can be used in vaccine development and/or production.

Diseases that can be studied by the organoids of the invention thus include genetic diseases, metabolic diseases, pathogenic diseases, inflammatory diseases etc, for example including, but not limited to: breast cancer, adenoma, mammary duct ectasia, fibrocystic changes (e.g. adenosis, metaplasia, dysplasia, hyperplasia, ductal lesions, lobular lesions, papillomas), mastitis, syphilis of the breast, tuberculosis of the breast and actinomycosis of the breast.

Traditionally, cell lines and more recently iPS cells have been used as ex vivo cell/organ and/or disease models (for example, see Robinton et al. Nature 481, 295, 2012). However, these methods suffer a number of challenges and disadvantages. For example, cell lines cannot be obtained from all patients (only certain biopsies result in successful cell lines) and therefore, cell lines cannot be used in personalised diagnostics and medicine. iPS cells usually require some level of genetic manipulation to reprogramme the cells into specific cell fates. Alternatively, they are subject to culture conditions that affect karotypic integrity and so the time in culture must be kept to a minimum (this is also the case for human embryonic stem cells). This means that iPS cells cannot accurately represent the in vivo situation but instead are an attempt to mimic the behaviour of in vivo cells. Cell lines and iPS cells also suffer from genetic instability.

By contrast, the organoids of the invention provide a genetically stable platform which faithfully represents the in vivo situation. The organoids of the invention can also be expanded continuously, providing a good source of genetically stable cells. In particular, an expanding population can be "split", meaning that the organoid is split apart and all cells of the organoid are divided into new culture dishes or flasks. The divided cells are removed from the organoid and can then themselves be cultured and expanded to produce new organoids containing further expanded populations that can then be split again. Splits are also referred to herein as "passages". An organoid of the invention may be cultured for 1 or more passages, for example, 1, 2, 3, 4, 5, 6, 7, 8, 9, 10, 15, 20, 25, 30 or more passages, for example, 20-30 passages, 30-35 passages, 32-40 passages or more. In some embodiments, an expanding cell population or organoid is split at every 3 days to every 10 weeks, every 1 to 10 weeks, every 1 to 4 weeks or every 10 days to 3 weeks. In some embodiments, the organoids are passaged approximately every 10 days to 3 weeks. Thus the organoids of the invention can provide an ongoing source of genetically stable cellular material. Thus the organoids of the invention can be used to gain mechanistic insight into a variety of diseases and therapeutics, to carry out in vitro drug screening, to evaluate potential therapeutics, to identify possible targets (e.g. proteins) for future novel (drug) therapy development and/or to explore gene repair coupled with cell-replacement therapy.

For these reason the organoids or expanded populations of cells of the invention can be a tool for drug screening, target validation, target discovery, toxicology and toxicology screens and personalized medicine.

Drug Screening

For preferably high-throughput purposes, said expanded stem cell population or organoid of the invention is cultured in multiwell plates such as, for example, 96 well plates or 384 well plates. Libraries of molecules are used to identify a molecule that affects said organoids. Preferred libraries comprise antibody fragment libraries, peptide phage display libraries, peptide libraries (e.g. LOPAP™, Sigma Aldrich), lipid libraries (BioMol), synthetic compound libraries (e.g. LOP AC™, Sigma Aldrich) or natural compound libraries (Specs, TimTec). Furthermore, genetic libraries can be used that induce or repress the expression of one of more genes in the progeny of the stem cells. These genetic libraries comprise cDNA libraries, antisense libraries, and siRNA or other non-coding RNA libraries. The cells are preferably exposed to multiple concentrations of a test agent for a certain period of time. At the end of the exposure period, the cultures are evaluated. The term "affecting" is used to cover any change in a cell, including, but not limited to, a reduction in, or loss of, proliferation, a morphological change, and cell death. Said expanded stem cell population or organoid of the invention can also be used to identify drugs that specifically target breast cancer cells, e.g. the breast cancer cells or breast cancer organoids of the invention, but not normal breast cells, e.g. not said normal expanded stem cell population or normal organoid of the invention. Of course, it is not necessary for the drug screening always to be high throughput and the organoids and cells of the invention are also useful for testing individual drug candidates.

The organoids are also useful for wider drug discovery purposes. It will be understood by the skilled person that the organoids of the invention would be widely applicable as drug screening tools for infectious, inflammatory and neoplastic pathologies of the human breast and other diseases of the breast. In some embodiments the organoids of the invention could be used for screening for cancer drugs.

In some embodiments, the expanded cell populations, for example the organoids of the invention or organoids obtained using media and methods of the invention can be used to test libraries of chemicals, antibodies, natural product (plant extracts), etc or specific known drugs for suitability for use as drugs, cosmetics and/or preventative medicines. For instance, in some embodiments, a cell biopsy from a patient of interest, such as tumour cells from a cancer patient, can be cultured using culture media and methods of the invention and then treated with a chemical compound or a chemical library or one or more drugs of interest. It is then possible to determine which compounds effectively modify, kill and/or treat the patient's cells. This allows specific patient responsiveness to a particular drug to be tested thus allowing treatment to be tailored to a specific patient. Thus, this allows a personalized medicine approach. The added advantage of using the organoids for identifying drugs in this way is that it is also possible to screen normal organoids (organoids derived from healthy tissue) to check which drugs and compounds have minimal effect on healthy tissue. This allows screening for drugs with minimal off-target activity or unwanted side-effects.

Drugs for any number of diseases can be screened in this way. For example the organoids of the invention can be used for screening for drugs for breast cancer, adenoma, mammary duct ectasia, fibrocystic changes (e.g. adenosis, metaplasia, dysplasia, hyperplasia, ductal lesions, lobular lesions, papillomas), mastitis, syphilis of the breast, tuberculosis of the breast and actinomycosis of the breast.

The testing parameters depend on the disease of interest. For example, when screening for cancer drugs, cancer cell death is usually the ultimate aim. In other embodiments, metabolics or gene expression may be evaluated to study the effects of compounds and drugs of the screen on the cells or organoids of interest.

Therefore, the invention provides a method for screening for a therapeutic or prophylactic drug, wherein the method comprises:

culturing an expanded cell population (for example, an organoid) of the invention, for example with a culture medium of the invention;

exposing said expanded cell population (for example, an organoid) of the invention to one or a library of candidate molecules;

evaluating said expanded cell populations (for example, organoids) for any effects, for example any change in the cell, such as a reduction in or loss of proliferation, a morphological change and/or cell death;

identifying the candidate molecule that causes said effects as a potential drug.

In some embodiments, computer- or robot-assisted culturing and data collection methods are employed to increase the throughput of the screen.

In some embodiments, expanded cell population (for example, an organoid) is obtained from a patient biopsy. In some embodiments, the candidate molecule that causes a desired effect on the cultured expanded cell population (for example, an organoid) is administered to said patient.

Accordingly, in one aspect, there is provided a method of treating a patient comprising:
(a) obtaining a biopsy from the diseased tissue of interest in the patient;
(b) screening for a suitable drug using a screening method of the invention, for example: culturing an expanded cell population (for example, an organoid) of the invention with a culture medium of the invention;
    exposing said expanded cell population (for example, an organoid) of the invention to one or a library of known drugs;
    evaluating said expanded cell populations (for example, organoids) for any effects, for example any change in the cell, such as a reduction in or loss of proliferation, a morphological change and/or cell death;
    identifying the candidate molecule that causes said effects as a suitable drug; and
(c) treating said patient with the drug obtained in step (b).

For example, the invention provides a method of treating breast cancer in a patient, comprising testing the patient's responsiveness to one or more drugs of interest using a drug screening method of the invention and then treating a patient with the drug if the patient is found to be responsive to the drug.

Similarly, there is provided a breast cancer drug for use in treating a patient with breast cancer, wherein said treatment comprises testing the patient's responsiveness to the drug using a drug screening method of the invention and treating the patient with the drug if the patient is found to be responsive to the drug.

Examples of drugs for use in the invention which can be tested using a personalized medicine approach as outlined above include Abitrexate (Methotrexate), Abraxane (Paclitaxel Albumin-stabilized Nanoparticle Formulation), Ado-Trastuzumab Emtansine, Adriamycin PFS (Doxorubicin Hydrochloride), Adriamycin RDF (Doxorubicin Hydrochloride), Adrucil (Fluorouracil), Afinitor (Everolimus), Anastrozole, Aredia (Pamidronate Disodium), Arimidex (Anastrozole), Aromasin (Exemestane), Capecitabine, Clafen (Cyclophosphamide), Cyclophosphamide, Cytoxan (Cyclophosphamide), Docetaxel, Doxorubicin Hydrochloride, Efudex (Fluorouracil), Ellence (Epirubicin Hydrochloride), Epirubicin Hydrochloride, Everolimus, Exemestane, Fareston (Toremifene), Faslodex (Fulvestrant), Femara (Letrozole), Fluoroplex (Fluorouracil), Fluorouracil, Folex (Methotrexate), Folex PFS (Methotrexate), Fulvestrant, Gemcitabine Hydrochloride, Gemzar (Gemcitabine Hydrochloride), Goserelin Acetate, Herceptin (Trastuzumab), Ixabepilone, Ixempra (Ixabepilone), Kadcyla (Ado-Trastuzumab Emtansine), Lapatinib Ditosylate, Letrozole, Megace (Megestrol Acetate), Megestrol Acetate, Methotrexate, Methotrexate LPF (Methotrexate), Mexate (Methotrexate), Mexate-AQ (Methotrexate), Neosar (Cyclophosphamide), Nolvadex (Tamoxifen Citrate), Novaldex (Tamoxifen Citrate), Paclitaxel, Paclitaxel Albumin-stabilized Nanoparticle Formulation, Pamidronate Disodium, Perjeta (Pertuzumab), Pertuzumab, Tamoxifen Citrate, Taxol (Paclitaxel), Taxotere (Docetaxel), Trastuzumab, Toremifene, Tykerb (Lapatinib Ditosylate), Xeloda (Capecitabine) and Zoladex (Goserelin Acetate).

Drugs for use in the invention which can be tested using a personalized medicine approach may be tested alone or in combination with one or more other drugs.

For example, (a) Doxorubicin Hydrochloride, Adriamycin PFS (Doxorubicin Hydrochloride) or Adriamycin RDF (Doxorubicin Hydrochloride) may be tested in combination with (b) Cyclophosphamide, Clafen (Cyclophosphamide), Cytoxan (Cyclophosphamide) or Neosar (Cyclophosphamide), and, optionally, in further combination with (c)(i) Paclitaxel, Paclitaxel Albumin-stabilized Nanoparticle Formulation, Abraxane (Paclitaxel Albumin-stabilized Nanoparticle Formulation) or Taxol (Paclitaxel), (c)(ii) Fluorouracil, Adrucil (Fluorouracil), Efudex (Fluorouracil) or Fluoroplex (Fluorouracil) or (c)(iii) Docetaxel or Taxotere (Docetaxel). Thus, the AC, AC-T, CAF and TAC drug combinations may be tested using a personalized medicine approach according to the invention.

For example, (a) Cyclophosphamide, Clafen (Cyclophosphamide), Cytoxan (Cyclophosphamide) or Neosar (Cyclophosphamide) may be tested in combination with (b) Fluorouracil, Adrucil (Fluorouracil), Efudex (Fluorouracil) or Fluoroplex (Fluorouracil) and (c)(i) Methotrexate, Abitrexate (Methotrexate), Folex (Methotrexate), Folex PFS (Methotrexate), Methotrexate LPF (Methotrexate), Mexate (Methotrexate) or Mexate-AQ (Methotrexate) or (c)(ii) Epirubicin Hydrochloride or Ellence (Epirubicin Hydrochloride). Thus, the CMF and FEC drug combinations may be tested using a personalized medicine approach according to the invention.

In some embodiments, the drug is used for treating, preventing or ameliorating symptoms of genetic diseases, metabolic diseases, pathogenic diseases, inflammatory diseases etc, for example including, but not limited to: breast cancer, adenoma, mammary duct ectasia, fibrocystic changes (e.g. adenosis, metaplasia, dysplasia, hyperplasia, ductal lesions, lobular lesions, papillomas), mastitis, syphilis of the breast, tuberculosis of the breast and actinomycosis of the breast.

Target Discovery

In some embodiments, the organoids of the invention or cells grown using the culture media and methods of the invention can be used for target discovery. Cells of the organoids originating from healthy or diseased tissue may be used for target identification. The organoids of the invention may be used for discovery of drug targets for: breast cancer, adenoma, mammary duct ectasia, fibrocystic changes (e.g. adenosis, metaplasia, dysplasia, hyperplasia, ductal lesions, lobular lesions, papillomas), mastitis, syphilis of the breast, tuberculosis of the breast and actinomycosis of the breast.

Cells and organoids cultured according to the media and methods of the invention are thought to faithfully represent the in vivo situation. For this reason they can be a tool to find novel (molecular) targets in specific diseases.

To search for a new drug target, a library of compounds (such as siRNA) may be used to transduce the cells and inactivate specific genes. In some embodiments, cells are transduced with siRNA to inhibit the function of a (large) group of genes. Any functional read out of the group of genes or specific cellular function can be used to determine if a target is relevant for the study. A disease-specific read out can be determined using assays well known in the art. For example, cellular proliferation is assayed to test for genes involved in cancer. For example, a Topflash assay as described herein, may be used to detect changes in Wnt activity caused by siRNA inhibition. Where growth reduction or cell death occurs, the corresponding siRNA related genes can be identified by methods known in the art. These genes are possible targets for inhibiting growth of these cells. Upon identification, the specificity of the identified target for the cellular process that was studied will need to be determined by methods well known in the art. Using these methods, new molecules can be identified as possible drug targets for therapy.

Target and Drug Validation Screens

Patient-specific organoids obtained from diseased and/or normal tissue can be used for target validation of molecules identified in high throughput screens. The same goes for the validation of compounds that were identified as possible therapeutic drugs in high throughput screens. The use of primary patient material expanded in the organoid culture system can be useful to test for false positives, etc. from high throughput drug discovery cell line studies.

In some embodiments, the expanded stem cell population (for example, organoid of the invention) can be used for validation of compounds that have been identified as possible drugs or cosmetics in a high-throughput screen.

Toxicity Assay

Said expanded stem cell population (for example, organoid of the invention) can further replace the use of cell lines in toxicity assays of potential novel drugs or of known drugs. Preferably, normal cells or organoids are used for these embodiments. However, it is also envisaged that cancer cells or organoids may be used.

Toxicology screens work in a similar way to drug screens (as described above) but they test for the toxic effects of drugs and not therapeutic effects. Therefore, in some embodiments, the effects of the candidate compounds are toxic.

Culturing Pathogens

Furthermore, said expanded stem cell population (for example, organoid of the invention) can be used for culturing of a pathogen such as mouse mammary tumour virus (MMTV), human mammary tumor virus (HMTV), Epstein Barr virus (EBV), high risk human papillomavirus (HPV), *Mycobacterium tuberculosis, Streptococcus uberis, Streptococcus dysgalactiae, Escherichia coli, Staphylococcus aureus*, or *Streptococcus agalactiae*.

Therapy Monitoring and Identifying Causes of Drug Resistance

Furthermore, said expanded stem cell population (for example, organoid of the invention) can be used for monitoring the progression of a disease in the expanded stem cell population alongside monitoring the progression of a disease in a patient. Thus, for example, an expanded population of breast cancer stem cells could be obtained from a patient with breast cancer, the patient could then be treated with a certain drug or combination of drugs, and if the patient develops resistance to the drug or combination of drugs then a second expanded population of breast cancer stem cells could be obtained from the patient and compared to the first population of breast cancer stem cells, in order to identify causes of drug resistance and an appropriate therapy.

Accordingly, said expanded stem cell population (for example, organoid of the invention) can be used for identifying causes of drug resistance. Thus, for example, an expanded population of breast cancer stem cells could be obtained from a patient with breast cancer, the patient could then be treated with a certain drug or combination of drugs, and if the patient develops resistance to the drug or combination of drugs then a second expanded population of breast cancer stem cells could be obtained from the patient and compared to the first population of breast cancer stem cells, in order to identify causes of drug resistance.

The causes of drug resistance may be identified by identifying genetic changes in the resistant population of stem cells compared to the population of stem cells that responds to treatment with the drug.

Regenerative Medicine and Transplantation

Cultures comprising the expanded stem cell population (for example, organoid of the invention) are useful in regenerative medicine, for example in post-radiation and/or post-surgery repair of breast tissue, for example post-mastectomy, or in tissue repair of injured breast tissue. For example, breast epithelial stem cells with BRCA mutations may be obtained from a cancer patient, the BRCA mutations may then be repaired, resulting in the generation of autologous breast epithelial stem cells, which may then be transplanted back into the cancer patient.

In an alternative embodiment, the expanded epithelial stem cells are reprogrammed into related tissue fates. It will be clear to a skilled person that gene therapy can additionally be used in a method directed at repairing damaged or diseased tissue. Use can, for example, be made of an adenoviral or retroviral gene delivery vehicle to deliver genetic information, like DNA and/or RNA to stem cells. A skilled person can replace or repair particular genes targeted in gene therapy. For example, a normal gene may be inserted into a nonspecific location within the genome to replace a non-functional gene. In another example, an abnormal gene sequence can be replaced for a normal gene sequence through homologous recombination. Alternatively, selective reverse mutation can return a gene to its normal function. A further example is altering the regulation (the degree to which a gene is turned on or off) of a particular gene. Preferably, the stem cells are ex vivo treated by a gene therapy approach and are subsequently transferred to the mammal, preferably a human being in need of treatment.

Since small biopsies taken from adult donors can be expanded without any apparent limit or genetic harm, the technology may serve to generate transplantable epithelium for regenerative purposes. Furthermore, in some embodiments, organoids embedded in, or in contact with, an ECM can be transplanted into a mammal, preferably into a human. In another embodiment, organoids and ECM can be transplanted simultaneously into a mammal, preferably into a human.

The skilled person would understand that an ECM can be used as a 3D scaffold for obtaining tissue-like structures comprising expanded populations of cells or organoids according to the invention. Such structures can then be transplanted into a patient by methods well known in the art. An ECM scaffold can be made synthetically using ECM proteins, such as collagen and/or laminin, or alternatively an ECM scaffold can be obtained by "decellularising" an isolated organ or tissue fragment to leave behind a scaffold consisting of the ECM (for example see Macchiarini et al. The Lancet, Volume 372, Issue 9655, Pages 2023-2030, 2008). In some embodiments, an ECM scaffold can be obtained by decellularising an organ or tissue fragment, wherein optionally said organ or tissue fragment is from the breast.

As mentioned above, the invention provides an organoid or population of cells of the invention for use in transplantation into a mammal, preferably into a human.

Advantageously, the invention enables a small biopsy to be taken from an adult donor and expanded without any apparent limit or genetic harm and so the technology provided herein may serve to generate transplantable epithelium for regenerative purposes.

The patient is preferably a human, but may alternatively be a non-human mammal, such as a cat, dog, horse, cow, pig, sheep, rabbit or mouse.

Thus, included within the scope of the invention are methods of treatment of a human or non-human animal patient through cellular therapy. Such cellular therapy encompasses the application of the stem cells or organoids of the invention to the patient through any appropriate means. Specifically, such methods of treatment involve the regeneration of damaged tissue. In accordance with the invention, a patient can be treated with allogeneic or autologous stem cells or organoids. "Autologous" cells are cells which originated from the same organism into which they are being re-introduced for cellular therapy, for example in order to permit tissue regeneration. However, the cells have not necessarily been isolated from the same tissue as the tissue they are being introduced into. An autologous cell does not require matching to the patient in order to overcome the problems of rejection. "Allogeneic" cells are cells which originated from an individual which is different from the individual into which the cells are being introduced for cellular therapy, for example in order to permit tissue regeneration, although of the same species. Some degree of patient matching may still be required to prevent the problems of rejection.

Generally the cells or organoids of the invention are introduced into the body of the patient by injection or implantation. Generally the cells will be directly injected into the tissue in which they are intended to act. A syringe containing cells of the invention and a pharmaceutically acceptable carrier is included within the scope of the invention. A catheter attached to a syringe containing cells of the invention and a pharmaceutically acceptable carrier is included within the scope of the invention.

The skilled person will be able to select an appropriate method and route of administration depending on the material that is being transplanted (i.e. population of cells, single cells in cell suspension, organoids or fragments of organoids).

As discussed above, cells of the invention can be used in the regeneration of tissue. In order to achieve this function, cells may be injected or implanted directly into the damaged tissue, where they may multiply and eventually differentiate into the required cell type. Alternatively, the organoid can be injected or implanted directly into the damaged tissue. Breast tissues that are susceptible to treatment include all damaged tissues, particularly including those which may have been damaged by disease (e.g. cancer), injury, trauma, an autoimmune reaction, or by a viral or bacterial infection. In some embodiments of the invention, the cells or organoids of the invention are used to regenerate the breast.

For example, in one embodiment, the cells or organoids of the invention are injected into a patient using a Hamilton syringe. Accordingly, the invention provides a syringe comprising the cells or organoids of the invention.

The skilled person will be aware what the appropriate dosage of cells or organoids of the invention will be for a particular condition to be treated.

In one embodiment the cells or organoids of the invention, either in solution, in microspheres or in microparticles of a variety of compositions, will be administered into the artery irrigating the tissue or the part of the damaged organ in need of regeneration. Generally such administration will be performed using a catheter. The catheter may be one of the large variety of balloon catheters used for angioplasty and/or cell delivery or a catheter designed for the specific purpose of delivering the cells to a particular local of the body. For certain uses, the cells or organoids may be encapsulated into microspheres made of a number of different biodegradable compounds, and with a diameter of about 15 μm. This method may allow intravascularly administered cells or organoids to remain at the site of damage, and not to go through the capillary network and into the systemic circulation in the first passage. The retention at the arterial side of the capillary network may also facilitate their translocation into the extravascular space.

In another embodiment, the cells or organoids of the invention may be implanted into the damaged tissue adhered to a biocompatible implant. Within this embodiment, the cells may be adhered to the biocompatible implant in vitro, prior to implantation into the patient. As will be clear to a person skilled in the art, any one of a number of adherents may be used to adhere the cells to the implant, prior to implantation. By way of example only, such adherents may include fibrin, one or more members of the integrin family, one or more members of the cadherin family, one or more members of the selectin family, one or more cell adhesion molecules (CAMs), one or more of the immunoglobulin family and one or more artificial adherents. This list is provided by way of illustration only, and is not intended to be limiting. It will be clear to a person skilled in the art, that any combination of one or more adherents may be used.

In another embodiment, the cells or organoids of the invention may be embedded in a matrix, prior to implantation of the matrix into the patient. Generally, the matrix will be implanted into the damaged tissue of the patient. Examples of matrices include collagen based matrices, fibrin based matrices, laminin based matrices, fibronectin based matrices and artificial matrices. This list is provided by way of illustration only, and is not intended to be limiting.

In a further embodiment, the cells or organoids of the invention may be implanted or injected into the patient together with a matrix forming component. This may allow the cells to form a matrix following injection or implantation, ensuring that the cells or organoids remain at the appropriate location within the patient. Examples of matrix forming components include fibrin glue liquid alkyl, cyanoacrylate monomers, plasticizers, polysaccharides such as dextran, ethylene oxide-containing oligomers, block co-polymers such as poloxamer and Pluronics, non-ionic surfactants such as Tween and Triton'8', and artificial matrix forming components. This list is provided by way of illustration only, and is not intended to be limiting. It will be clear to a person skilled in the art, that any combination of one or more matrix forming components may be used.

In a further embodiment, the cells or organoids of the invention may be contained within a microsphere. Within this embodiment, the cells may be encapsulated within the centre of the microsphere. Also within this embodiment, the cells may be embedded into the matrix material of the microsphere. The matrix material may include any suitable biodegradable polymer, including but not limited to alginates, Poly ethylene glycol (PLGA), and polyurethanes. This list is provided by way of example only, and is not intended to be limiting.

In a further embodiment, the cells or organoids of the invention may be adhered to a medical device intended for implantation. Examples of such medical devices include stitches and artificial skin. This list is provided by way of illustration only, and is not intended to be limiting. It will be clear to a person skilled in the art, that the cells may be adhered to the medical device by a variety of methods. For example, the cells or organoids may be adhered to the medical device using fibrin, one or more members of the integrin family, one or more members of the cadherin family, one or more members of the selectin family, one or more cell adhesion molecules (CAMs), one or more of the immunoglobulin family and one or more artificial adherents. This list is provided by way of illustration only, and is not intended to be limiting. It will be clear to a person skilled in the art, that any combination of one or more adherents may be used.

Other Uses of Organoids of the Invention

The cells or organoids of the invention may be used to define patient groups for drug development. The cells or organoids of the invention may also be used for pre-screening patients in phase I or phase II trials. For example, the cells or organoids of the invention may be used to identify patients on which to perform a clinical trial. The cells or organoids of the invention may also be used in diagnostics after a drug is approved. For example, the cells or organoids of the invention may be used to identify patients who are most likely to benefit from a particular drug, to identify patients likely to be at increased risk for serious side effects as a result of treatment with a particular drug or to monitor the response to treatment with a particular drug for the purpose of adjusting treatment to achieve improved safety or effectiveness.

The cells or organoids of the invention may in some embodiments be used for veterinary therapies. For example, the cells or organoids may be used in the treatment of mastitis in cows.

Compositions and Other Forms of the Invention

The invention provides a pharmaceutical composition comprising the cells or organoids of the invention and further comprising a pharmaceutically acceptable carrier or excipient.

The invention provides a composition comprising a culture medium according to the invention and stem cells. The invention also provides a composition comprising a culture medium according to the invention and organoids. Furthermore, the invention provides a composition comprising a culture medium according to the invention and an extracellular matrix.

The invention also provides a composition comprising a culture medium of the invention, an extracellular matrix and stem cells of the invention. The invention also provides a composition comprising a culture medium of the invention, an extracellular matrix and one or more organoids of the invention. The invention also provides a culture medium supplement that can be used to produce a culture medium as disclosed herein. A 'culture medium supplement' is a mixture of ingredients that cannot itself support stem cells, but which enables or improves stem cell culture when combined with other cell culture ingredients. The supplement can therefore be used to produce a functional cell culture medium of the invention by combining it with other cell culture ingredients to produce an appropriate medium formulation. The use of culture medium supplements is well known in the art.

The invention provides a culture medium supplement that comprises an ErbB3/4 ligand according to the invention. The supplement may contain any ErbB3/4 ligand (or combination of ErbB3/4 ligand) disclosed herein. The supplement may also contain one or more additional cell culture ingredients as disclosed herein, e.g. one or more cell culture ingredients selected from the group consisting of amino acids, vitamins, inorganic salts, carbon energy sources and buffers.

A culture medium or culture medium supplement may be a concentrated liquid culture medium or supplement (e.g. a 2× to 250× concentrated liquid culture medium or supplement) or may be a dry culture medium or supplement. Both liquid and dry culture media or supplements are well known in the art. A culture medium or supplement may be lyophilised.

A culture medium or supplement of the invention will typically be sterilized prior to use to prevent contamination, e.g. by ultraviolet light, heating, irradiation or filtration. A culture medium or culture medium supplement may be frozen (e.g. at −20° C. or −80° C.) for storage or transport. In some embodiments, the culture medium may be stored as a liquid (e.g. at approximately 4° C.). In some embodiments, the culture medium may be split and stored as two components: a frozen component (e.g. at between approximately −20° C. and approximately −80° C.) and a liquid component (e.g. at approximately 4° C.). In particular, temperature-sensitive or time-sensitive degradable material is preferably included in the frozen component, whereas less sensitive material (for example DMEM or FCS) can be stored in the liquid form and thus included in the liquid component for storage and shipping.

The invention also provides a hermetically-sealed vessel containing a culture medium or culture medium supplement of the invention. Hermetically-sealed vessels may be preferred for transport or storage of the culture media or culture media supplements disclosed herein, to prevent contamination. The vessel may be any suitable vessel, such as a flask, a plate, a bottle, a jar, a vial or a bag.

The invention also provides a kit comprising a culture medium, culture medium supplement and/or a composition of the invention. In some embodiments, the kit further comprises at least one other additional component, for example selected from the list comprising: an ECM (for example, Matrigel™ or Cultrex® Basement Membrane Extract), a population of cells and an organoid.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Various aspects and embodiments of the invention are described below in more detail by way of example. It will be appreciated that modification of detail may be made without departing from the scope of the invention.

EXAMPLES

Example 1—Tissue Processing and Mammary Organoid Culture

Figure 1B:
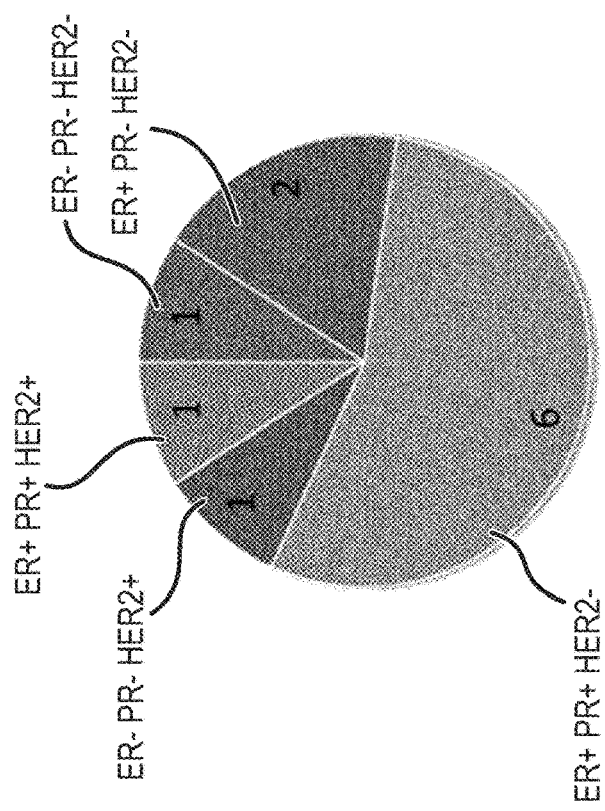
FIG. 1. (A) Breast tumour tissues obtained from patients displayed according to subtype (estrogen receptor (ER), progesterone receptor (PR) and human epidermal growth factor receptor-2 (HER2) status); (B) established or promising organoid lines displayed according to subtype (ER, PR and HER2 status).
Figure 1A:
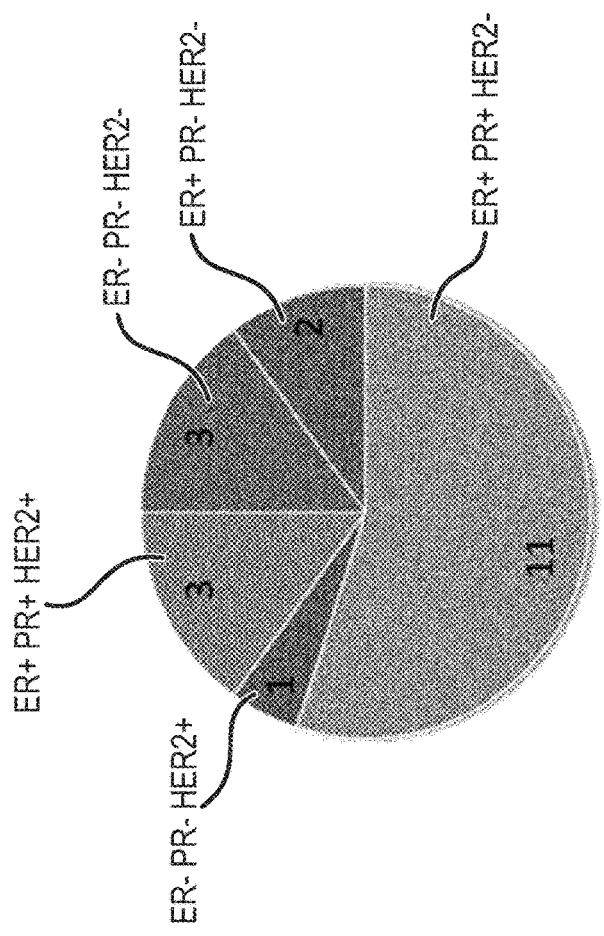

Overview 20 breast tumors were sampled, three of which were triple negative (15%, FIG. 1A and FIG. 13). We successfully established three tumor organoid lines (splitting ratio >1:2, passage >7). 8 additional cultures are currently expanding and will, based on our experience, most likely generate successful organoid lines (FIG. 2 and FIG. 13). A selection for a specific subtype is not evident (FIG. 1B).

From the 19 normal samples obtained we thus far established three promising cultures (FIG. 2, FIG. 13).

Culture Conditions

The first 12 samples were used to optimize cell isolation and organoid culture conditions. Samples 13-20 were grown in six different conditions.

Altered Parameters for Cell Isolation

For the isolation of viable cells we tested several digestive enzymes (collagenase, dispase, trypsin) at different concentrations (1-5 mg/ml) in different media (AdDF+++, base medium, base-$F_{7/10}$N medium) for different periods of time (1-2 h, 12 h) with or without agitation. The compositions of these base media are displayed in FIG. 14. The optimal protocol is summarized below.

Altered Parameters for Organoid Culture

Figure 3A:
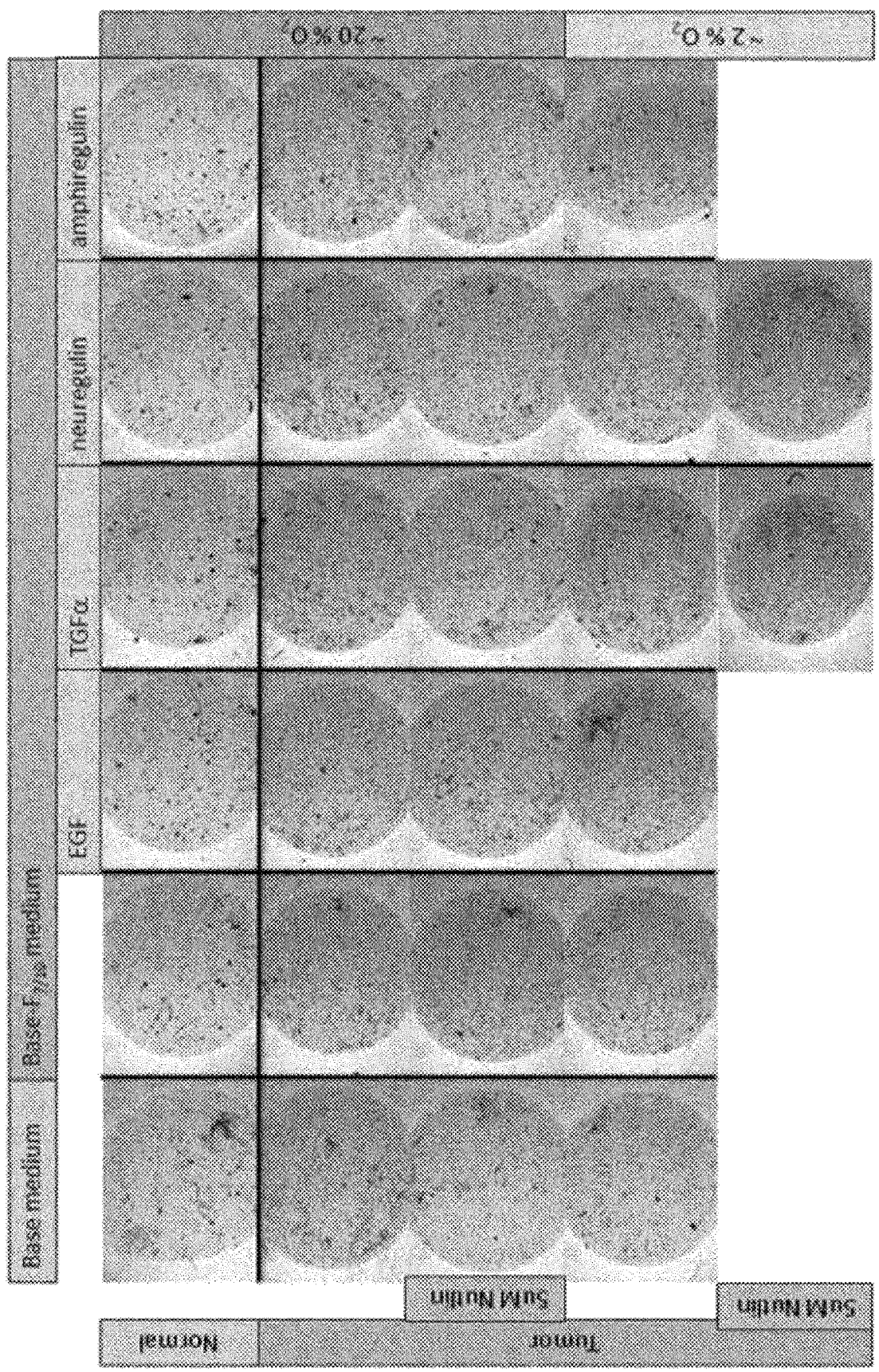
FIG. 3. Example of media optimization. Normal and tumour mammary cells of patient W855 were suspended in Cultrex® Basement Membrane Extract (Trevigen, Inc.) and supplemented with the indicated media. Phase contrast images are displayed for: (A) Passage 0 day 4 and (B) Passage 0 day 14. The most beneficial culture conditions are marked by bold grey boxes. Image widths: 1.5 mm top panels, 300 µm bottom panels.
Figure 3B:
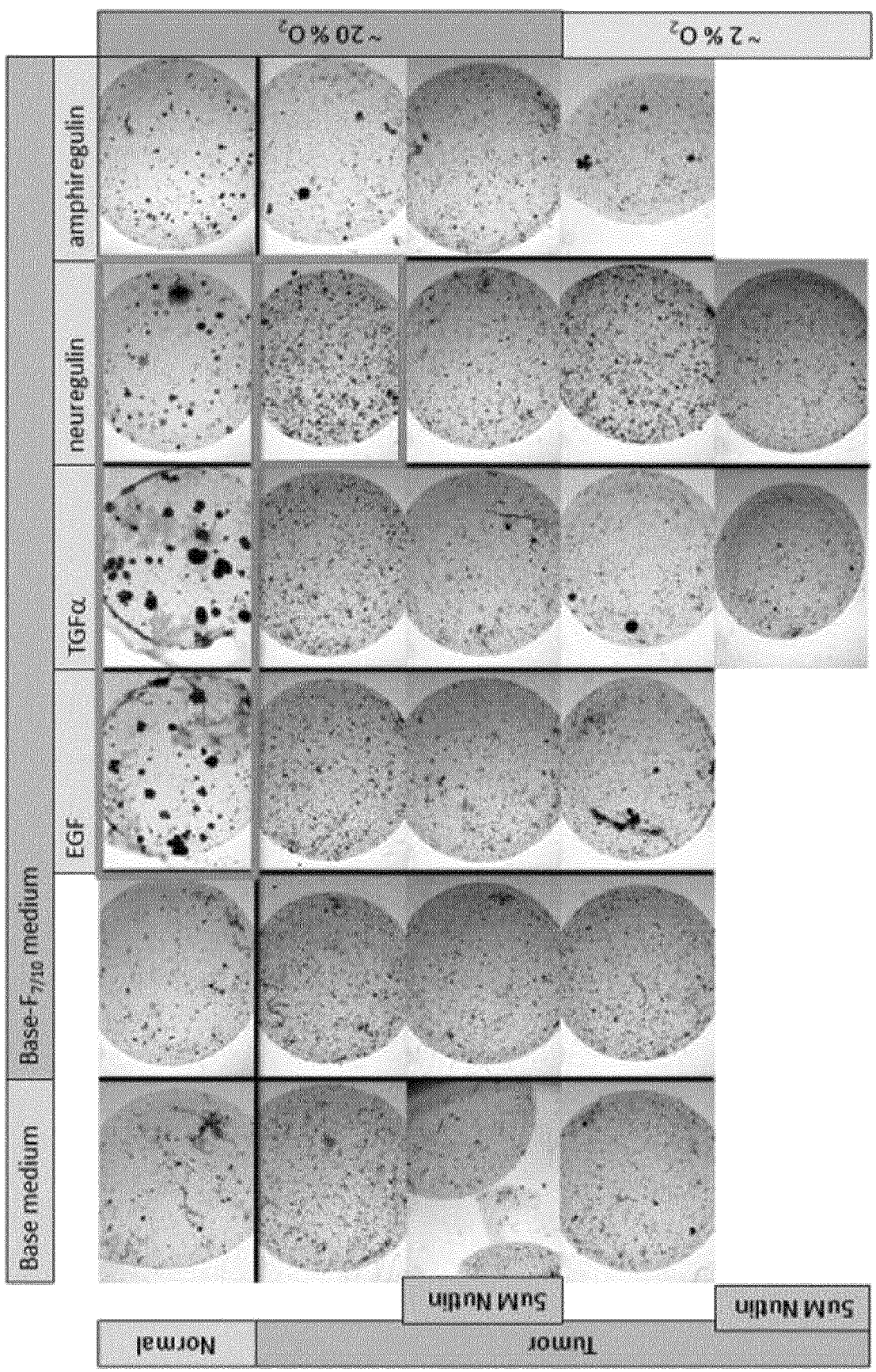

To allow organoid growth we tested several culture conditions in parallel (6-12 conditions/sample). Based on previous experience with other human tissue we tested several growth factors on top of our base medium (FIG. 14). Other parameters tested included BME (basement membrane extract) density (50-100%) instead of Matrigel, the use of tissue culture treated vs suspension plates, and culturing at 2% vs ambient $O_2$. An example of the effect of different culture conditions is given for normal and tumor organoid lines obtained from patient W855 (FIG. 3).

Protocol for Tissue Processing and Mammary Organoid Culture

Upon arrival, tissues were photographed and cut into 1-3 mm³ pieces. Two random pieces were snap frozen and stored at −80° C. for DNA isolation, two random pieces were fixed in formalin for histopathological analysis and immunohistochemistry, and the remainder was processed for the isolation of viable cells. The remaining tissue was minced, washed with 10 ml AdDF+++ and digested in 10 ml base-$F_{7/10}$N medium containing 1-2 mg/ml collagenase (Sigma-C9407) at 120 rpm and 37° C. for 1-2 h. The digested tissue suspension was sequentially sheared using 10 ml and 5 ml plastic and flamed glass Pasteur pipettes. After every shearing step the suspension was strained over a 100 μm filter with retained tissue pieces entering a subsequent shearing step with ~10 ml AdDF+++. 2% FCS were added to the strained suspension before centrifugation at 400 g. The pellet was resuspended in 10 ml AdDF+++ and centrifuged again at 400. In case of a visible red pellet, erythrocytes were lysed in 2 ml red blood cell lysis buffer (Roche-11814389001) for 5 min at room temperature before the addition of 10 ml AdDF+++ and centrifugation at 400 g. The pellet was resuspended in 10 mg/ml cold Cultrex growth factor reduced BME type 2 (Trevigen-3533-010-02) and 40 μl drops of BME-cell suspension were allowed to solidify on prewarmed 24-well suspension culture plates (Greiner-M9312) at 37° C. for 10-20 min. Upon completed gelation, 400 μl of organoid media (base-$F_{7/10}$N, base-$F_{7/10}$EN, or base-$F_{7/10}$PN) were added to each well and plates transferred to humidified 37° C./5% $CO_2$ incubators at either 2% or ambient $O_2$.

Medium was changed every 4 days and organoids were passaged every 1-4 weeks: cystic organoids were resuspended in 2 ml cold AdDF+++ and mechanically sheared through flamed glass Pasteur pipettes. Dense organoids were dissociated by resuspension in 2 ml TrypLE Express (Invitrogen-12605036), incubation for 1-5 min at room temperature, and mechanical shearing through flamed glass Pasteur pipettes. Following the addition of 10 ml AdDF+++ and centrifugation at 300 g or 400 g respectively, organoid fragments were resuspended in cold BME and reseeded as above at ratios (1:1-1:6) allowing the formation of new organoids. Single cell suspensions were initially seeded at high density and reseeded at a lower density after ~1 week.

Example 2—Characterization of Established Mammary Tumor Organoid Lines

Mammary tumor organoid lines W854T, W855T, and W859T readily expand in base-$F_{7/10}$N medium and were therefore characterized in more detail.

Figure 4:
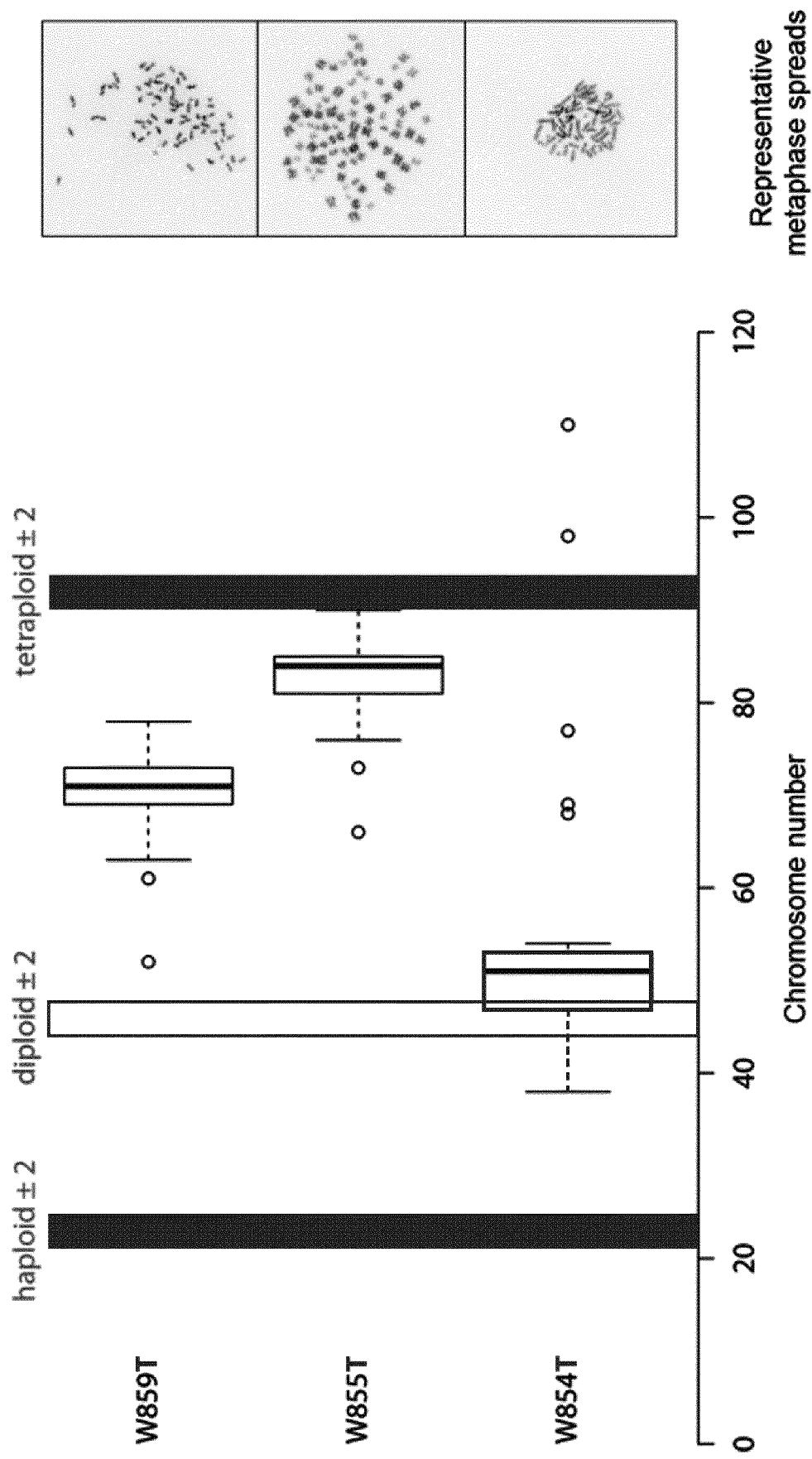
FIG. 4. Aneuploid karyotypes of established mammary tumour organoid lines.

Their tumor status was confirmed through karyotyping revealing aneuploidy at varying degrees (FIG. 4).

Line W854T furthermore readily grew in medium containing 5 μM Nutlin-3 indicating the presence of mutant p53. RNA and DNA were isolated and sent to BI for gene expression profiling and exome sequencing.

Figure 5:
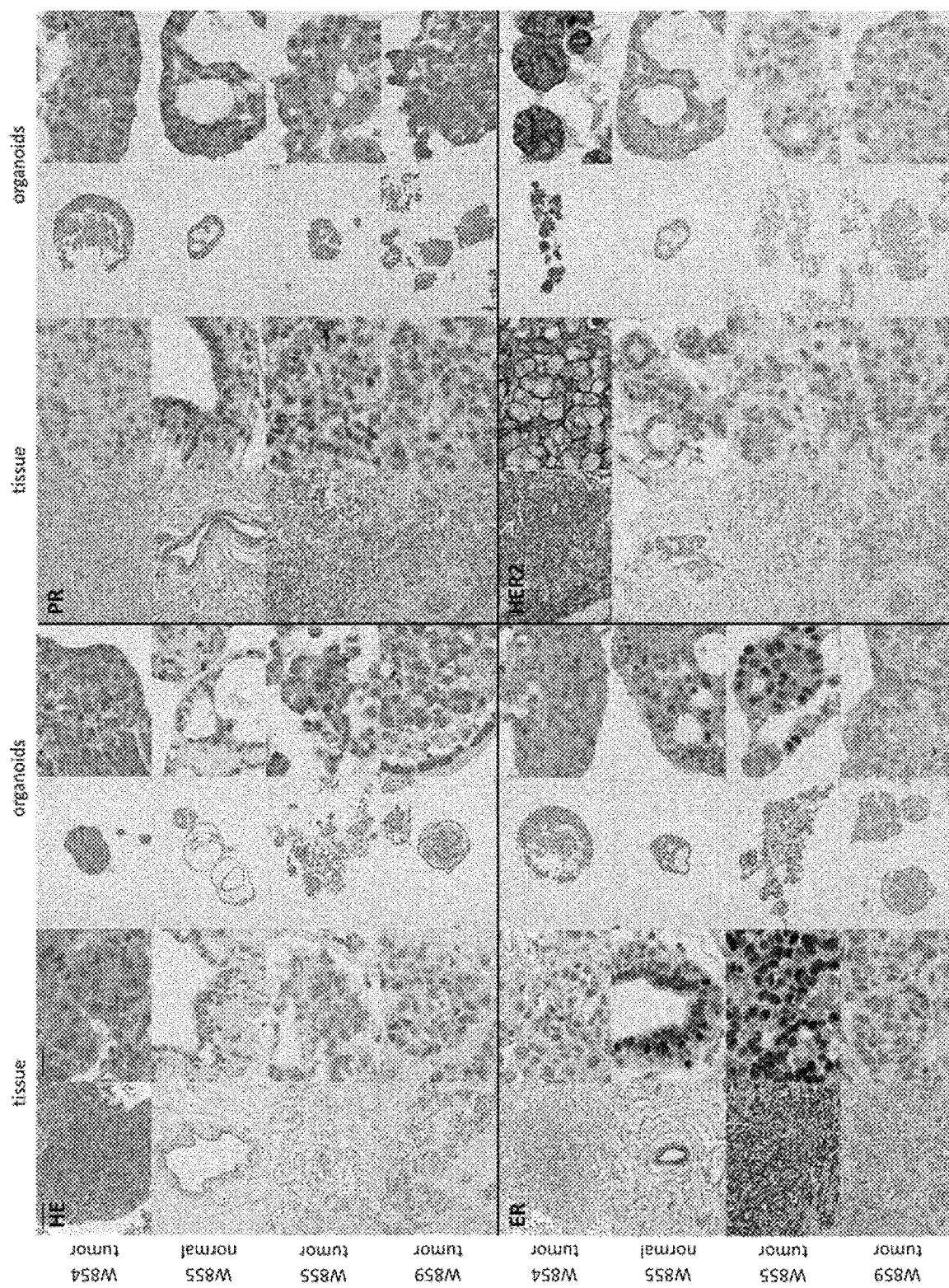
FIG. 5. Histological and immunohistochemical comparison of original mammary gland tissue (W854 tumour (W854T), W855 normal and tumour (W855N and W855T), W859 tumour (W859T)) with the respectively derived organoid lines. Scale bars equal 100 µm (overview) and 20 µm (detailed view). Key: HE=haematoxylin and eosin stain; PR=progesterone receptor (clone PgR 636, M356929 Dako), ER=estrogen receptor alpha (clone SP1, ab16660 Abcam), HER2=human epidermal growth factor receptor 2 (c-erbB2) (clone SP3, #RM-9103, Thermoscientific).
Figure 6:
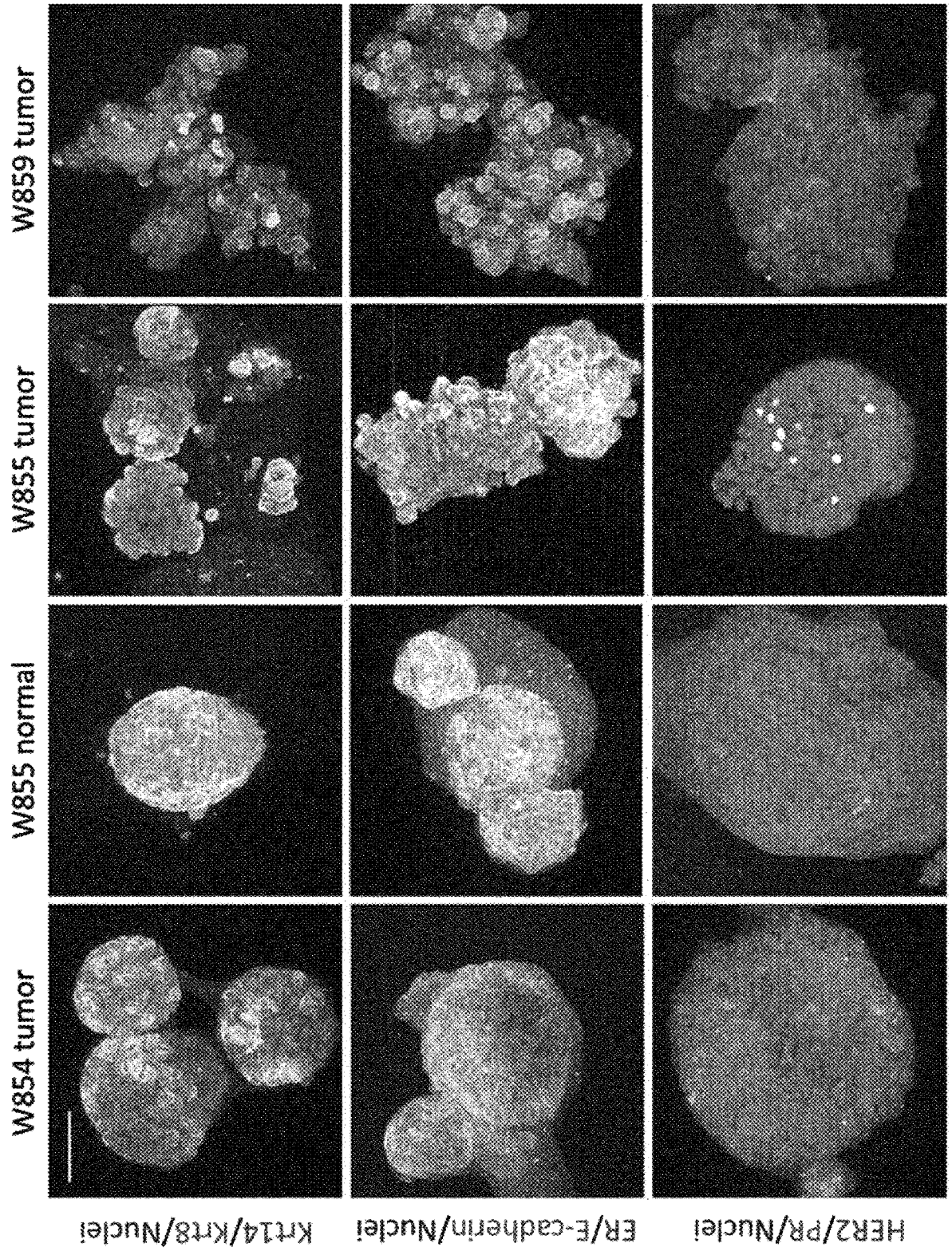
FIG. 6. Immunofluorescent analysis of whole mounted normal (W855) and tumour (W854, W855 and W859) mammary organoid lines. Nuclear counterstain is DRAQS (DR50050 Biostatus limited). Scale bar equals 100 µm. Key.

Histological and immunofluorescent analysis confirmed that ER, PR, and HER2 status are conserved between originating tumor and established tumor organoid line after >7 passages (FIGS. 5 and 6).

Whereas normal organoid line W855N consists of mutually exclusive basal and luminal cells, tumor organoids solely express luminal cell marker Keratin-8 (FIGS. 6 and 7). E-cadherin expression is present but decreased in tumor compared to normal organoid lines indicating their epithelial origin (FIGS. 6 and 7). However, markers of epithelial to mesenchymal transition (EMT) are mildly upregulated in tumor organoid lines W855T and W859T corresponding to their incoherent phenotype (FIGS. 6 and 7).

Example 3—Low Throughput Drug Screen

To test the feasibility of mammary tumor organoids for drug screening, lines W854T, W855T, and W859T were plated in duplicate into a 96-well format and exposed to medium containing the EGFR inhibitor Iressa (1 nM-30 μM at 1:3 dilution steps, S1025 Selleck Chemicals) or the p53 stabilizer Nutlin-3 (1 nM-30 μM at 1:3 dilution steps, 10004372 Cayman Chemicals) for 7 days. Organoids were photographed every 3-4 days (FIG. 8) and cell viability measured at day 7 using the CellTiter-Glo 2.0 assay (G9241, Promega) (FIG. 9).

All three organoid lines respond to Iressa at concentrations ~10 μM indicating a dependence on EGFR signaling. With perhaps the exception of W855T, Nutlin-3 does not inhibit growth at concentrations up 30 μM indicating the presence of mutant p53 (FIG. 9). Mammary tumor organoids are suitable for cell viability based low throughput drug screens in a 96-well format. We are currently testing the assay in a 384-well plate format which has been successfully established for colon cancer organoids.

Example 4—Culture Medium of Pasic et al. does not Support Long-Term Growth

Normal mammary organoids in Pasic's culture medium slowed expanding at passage 2 and stopped at passage 3; organoids from the same patient grown in base-$F_{7/10}$E continued expanding up to passage 4 (see FIG. 10). Normal mammary organoids from different patients expand at least up to passage 6 in medium base $F_{7/10}$ EN.

---

The invention claimed is:

1. A method for obtaining a breast organoid by expanding breast epithelial stem cells comprising:
   providing a population of breast stem cells;
   providing a culture medium comprising an ErbB3/4 ligand, one or more FGFR2b ligands and a Wnt agonist, wherein the Wnt agonist is an Lgr5 agonist or Wnt3a; and wherein the culture medium is suitable for expanding a population of breast epithelial stem cells for at least 6 passages;
   contacting the stem cells with the culture medium; and
   culturing the cells under appropriate conditions and thereby obtaining a breast organoid.

2. The method of claim 1, wherein the ErbB3/4 ligand is a neuregulin polypeptide.

3. The method of claim 2, wherein the neuregulin polypeptide is encoded by NRG1.

4. The method of claim 2, wherein the neuregulin polypeptide comprises the amino acid sequence recited in SEQ ID NO: 27.

5. The method of claim 1, wherein the one or more FGFR2b ligands is FGF7 and/or FGF10.

6. The method of claim 1, wherein the Wnt agonist is an Lgr5 agonist.

7. The method of claim 6, wherein the Lgr5 agonist is an Rspondin, a biologically active fragment or derivative of Rspondin, an anti-Lgr5 antibody, or an Rspondin mimic.

8. The method of claim 1, wherein the culture medium further comprises a BMP inhibitor, B27, N-acetylcysteine, Nicotinamide, a ROCK inhibitor, a TGF-beta inhibitor, a p38 inhibitor, one or more receptor tyrosine kinase ligands, and/or a p53 stabilizing agent.

9. The method of claim 8, wherein the culture medium further comprises: B27, N-acetylcysteine, Nicotinamide, a ROCK inhibitor, a TGF-beta inhibitor and a p38 inhibitor.

10. The method of claim 8, wherein:
    (a) the BMP inhibitor is Noggin, and/or
    (b) the ROCK inhibitor is Y-27632, and/or
    (c) the TGF-beta inhibitor is A83-01, and/or
    (d) the p38 inhibitor is SB 202190.

11. The method of claim 8, wherein:
    (a) the one or more further receptor tyrosine kinase ligands are EGF, PDGF and/or amphiregulin, and/or
    (b) the p53 stabilizing agent is a member of the Nutlin family.

12. The method of claim 11, wherein:
    (a) the PDGF is PDGF-CC, and/or
    (b) the member of the Nutlin family is Nutlin-3.

13. The method of claim 7, wherein the Rspondin is one or more of Rspondin 1, Rspondin 2, Rspondin3, and Rspondin 4.

14. The method of claim 7, wherein the biologically active fragment of Rspondin comprises the furin domain.

15. The method of claim 7, wherein the anti-Lgr5 antibody is an agonistic anti-Lgr5 antibody.

* * * * *

SEQUENCE LISTING

```
<160> NUMBER OF SEQ ID NOS: 33

<210> SEQ ID NO 1
<211> LENGTH: 607
<212> TYPE: PRT
<213> ORGANISM: Homo sapiens

<400> SEQUENCE: 1

Met Gly Lys Gly Arg Ala Gly Arg Val Gly Thr Thr Ala Leu Pro Pro
1               5                   10                  15

Arg Leu Lys Glu Met Lys Ser Gln Glu Ser Ala Ala Gly Ser Lys Leu
            20                  25                  30

Val Leu Arg Cys Glu Thr Ser Ser Glu Tyr Ser Ser Leu Arg Phe Lys
        35                  40                  45

Trp Phe Lys Asn Gly Asn Glu Leu Asn Arg Lys Asn Lys Pro Gln Asn
    50                  55                  60

Ile Lys Ile Gln Lys Lys Pro Gly Lys Ser Glu Leu Arg Ile Asn Lys
65                  70                  75                  80

Ala Ser Leu Ala Asp Ser Gly Glu Tyr Met Cys Lys Val Ile Ser Lys
                85                  90                  95

Leu Gly Asn Asp Ser Ala Ser Ala Asn Ile Thr Ile Val Glu Ser Asn
            100                 105                 110

Glu Ile Ile Thr Gly Met Pro Ala Ser Thr Glu Gly Ala Tyr Val Ser
        115                 120                 125

Ser Ala Thr Ser Thr Ser Thr Thr Gly Thr Ser His Leu Val Lys Cys
    130                 135                 140

Ala Glu Lys Glu Lys Thr Phe Cys Val Asn Gly Gly Glu Cys Phe Met
145                 150                 155                 160

Val Lys Asp Leu Ser Asn Pro Ser Arg Tyr Leu Cys Lys Cys Pro Asn
                165                 170                 175

Glu Phe Thr Gly Asp Arg Cys Gln Asn Tyr Val Met Ala Ser Phe Tyr
            180                 185                 190

Lys His Leu Gly Ile Glu Phe Met Glu Ala Glu Glu Leu Tyr Gln Lys
        195                 200                 205

Arg Val Leu Thr Ile Thr Gly Ile Cys Ile Ala Leu Leu Val Val Gly
    210                 215                 220

Ile Met Cys Val Val Ala Tyr Cys Lys Thr Lys Lys Gln Arg Lys Lys
225                 230                 235                 240

Leu His Asp Arg Leu Arg Gln Ser Leu Arg Ser Glu Arg Asn Asn Met
                245                 250                 255

Met Asn Ile Ala Asn Gly Pro His His Pro Asn Pro Pro Pro Glu Asn
            260                 265                 270

Val Gln Leu Val Asn Gln Tyr Val Ser Lys Asn Val Ile Ser Ser Glu
        275                 280                 285

His Ile Val Glu Arg Glu Ala Glu Thr Ser Phe Ser Thr Ser His Tyr
    290                 295                 300

Thr Ser Thr Ala His His Ser Thr Thr Val Thr Gln Thr Pro Ser His
305                 310                 315                 320

Ser Trp Ser Asn Gly His Thr Glu Ser Ile Leu Ser Glu Ser His Ser
                325                 330                 335
```

```
Val Ile Val Met Ser Val Glu Asn Ser Arg His Ser Ser Pro Thr
            340                 345                 350

Gly Gly Pro Arg Gly Arg Leu Asn Gly Thr Gly Pro Arg Glu Cys
            355                 360                 365

Asn Ser Phe Leu Arg His Ala Arg Glu Thr Pro Asp Ser Tyr Arg Asp
            370                 375                 380

Ser Pro His Ser Glu Arg Tyr Val Ser Ala Met Thr Thr Pro Ala Arg
385                 390                 395                 400

Met Ser Pro Val Asp Phe His Thr Pro Ser Ser Pro Lys Ser Pro Pro
                405                 410                 415

Ser Glu Met Ser Pro Pro Val Ser Ser Met Thr Val Ser Met Pro Ser
            420                 425                 430

Met Ala Val Ser Pro Phe Met Glu Glu Glu Arg Pro Leu Leu Leu Val
            435                 440                 445

Thr Pro Pro Arg Leu Arg Glu Lys Lys Phe Asp His His Pro Gln Gln
            450                 455                 460

Phe Ser Ser Phe His His Asn Pro Ala His Asp Ser Asn Ser Leu Pro
465                 470                 475                 480

Ala Ser Pro Leu Arg Ile Val Glu Asp Glu Glu Tyr Glu Thr Thr Gln
                485                 490                 495

Glu Tyr Glu Pro Ala Gln Glu Pro Val Lys Lys Leu Ala Asn Ser Arg
            500                 505                 510

Arg Ala Lys Arg Thr Lys Pro Asn Gly His Ile Ala Asn Arg Leu Glu
            515                 520                 525

Val Asp Ser Asn Thr Ser Ser Gln Ser Ser Asn Ser Glu Ser Glu Thr
530                 535                 540

Glu Asp Glu Arg Val Gly Glu Asp Thr Pro Phe Leu Gly Ile Gln Asn
545                 550                 555                 560

Pro Leu Ala Ala Ser Leu Glu Ala Thr Pro Ala Phe Arg Leu Ala Asp
                565                 570                 575

Ser Arg Thr Asn Pro Ala Gly Arg Phe Ser Thr Gln Glu Glu Ile Gln
            580                 585                 590

Ala Arg Leu Ser Ser Val Ile Ala Asn Gln Asp Pro Ile Ala Val
            595                 600                 605

<210> SEQ ID NO 2
<211> LENGTH: 308
<212> TYPE: PRT
<213> ORGANISM: Homo sapiens

<400> SEQUENCE: 2

Met Gln Ile Pro Lys His Ile Ser Ile Glu Asp Ile Thr Ala Thr Ser
1               5                   10                  15

Thr Ser Thr Thr Gly Thr Ser His Leu Val Lys Cys Ala Glu Lys Glu
            20                  25                  30

Lys Thr Phe Cys Val Asn Gly Gly Glu Cys Phe Met Val Lys Asp Leu
        35                  40                  45

Ser Asn Pro Ser Arg Tyr Leu Cys Lys Cys Gln Pro Gly Phe Thr Gly
    50                  55                  60

Ala Arg Cys Thr Glu Asn Val Pro Met Lys Val Gln Asn Gln Glu Lys
65                  70                  75                  80

Ala Glu Glu Leu Tyr Gln Lys Arg Val Leu Thr Ile Thr Gly Ile Cys
                85                  90                  95

Ile Ala Leu Leu Val Val Gly Ile Met Cys Val Val Ala Tyr Cys Lys
```

```
                100             105             110
Thr Lys Lys Gln Arg Lys Lys Leu His Asp Arg Leu Arg Gln Ser Leu
            115                 120                 125
Arg Ser Glu Arg Asn Asn Met Met Asn Ile Ala Asn Gly Pro His His
        130                 135                 140
Pro Asn Pro Pro Pro Glu Asn Val Gln Leu Val Asn Gln Tyr Val Ser
145                 150                 155                 160
Lys Asn Val Ile Ser Ser Glu His Ile Val Glu Arg Glu Ala Glu Thr
                165                 170                 175
Ser Phe Ser Thr Ser His Tyr Thr Ser Thr Ala His His Ser Thr Thr
            180                 185                 190
Val Thr Gln Thr Pro Ser His Ser Trp Ser Asn Gly His Thr Glu Ser
        195                 200                 205
Ile Leu Ser Glu Ser His Ser Val Ile Val Met Ser Ser Val Glu Asn
        210                 215                 220
Ser Arg His Ser Ser Pro Thr Gly Gly Pro Arg Gly Arg Leu Asn Gly
225                 230                 235                 240
Thr Gly Gly Pro Arg Glu Cys Asn Ser Phe Leu Arg His Ala Arg Glu
                245                 250                 255
Thr Pro Asp Ser Tyr Arg Asp Ser Pro His Ser Glu Arg His Asn Leu
            260                 265                 270
Ile Ala Glu Leu Arg Arg Asn Lys Ala His Arg Ser Lys Cys Met Gln
        275                 280                 285
Ile Gln Leu Ser Ala Thr His Leu Arg Ser Ser Ile Pro His Leu
    290                 295                 300
Gly Phe Ile Leu
305

<210> SEQ ID NO 3
<211> LENGTH: 624
<212> TYPE: PRT
<213> ORGANISM: Homo sapiens

<400> SEQUENCE: 3

Met Gly Lys Gly Arg Ala Gly Arg Val Gly Thr Thr Ala Leu Pro Pro
1               5                   10                  15
Arg Leu Lys Glu Met Lys Ser Gln Glu Ser Ala Ala Gly Ser Lys Leu
            20                  25                  30
Val Leu Arg Cys Glu Thr Ser Ser Glu Tyr Ser Ser Leu Arg Phe Lys
        35                  40                  45
Trp Phe Lys Asn Gly Asn Glu Leu Asn Arg Lys Asn Lys Pro Gln Asn
    50                  55                  60
Ile Lys Ile Gln Lys Lys Pro Gly Lys Ser Glu Leu Arg Ile Asn Lys
65                  70                  75                  80
Ala Ser Leu Ala Asp Ser Gly Glu Tyr Met Cys Lys Val Ile Ser Lys
                85                  90                  95
Leu Gly Asn Asp Ser Ala Ser Ala Asn Ile Thr Ile Val Glu Ser Asn
            100                 105                 110
Glu Ile Ile Thr Gly Met Pro Ala Ser Thr Glu Gly Ala Tyr Val Ser
        115                 120                 125
Ser Glu Ser Pro Ile Arg Ile Ser Val Ser Thr Glu Gly Ala Asn Thr
    130                 135                 140
Ser Ser Ser Thr Ser Thr Ser Thr Thr Gly Thr Ser His Leu Val Lys
145                 150                 155                 160
```

```
Cys Ala Glu Lys Glu Lys Thr Phe Cys Val Asn Gly Gly Glu Cys Phe
            165                 170                 175
Met Val Lys Asp Leu Ser Asn Pro Ser Arg Tyr Leu Cys Lys Cys Pro
        180                 185                 190
Asn Glu Phe Thr Gly Asp Arg Cys Gln Asn Tyr Val Met Ala Ser Phe
            195                 200                 205
Tyr Lys His Leu Gly Ile Glu Phe Met Glu Ala Glu Leu Tyr Gln
        210                 215                 220
Lys Arg Val Leu Thr Ile Thr Gly Ile Cys Ile Ala Leu Leu Val Val
225                 230                 235                 240
Gly Ile Met Cys Val Val Ala Tyr Cys Lys Thr Lys Lys Gln Arg Lys
                245                 250                 255
Lys Leu His Asp Arg Leu Arg Gln Ser Leu Arg Ser Glu Arg Asn Asn
            260                 265                 270
Met Met Asn Ile Ala Asn Gly Pro His His Pro Asn Pro Pro Pro Glu
        275                 280                 285
Asn Val Gln Leu Val Asn Gln Tyr Val Ser Lys Asn Val Ile Ser Ser
        290                 295                 300
Glu His Ile Val Glu Arg Glu Ala Glu Thr Ser Phe Ser Thr Ser His
305                 310                 315                 320
Tyr Thr Ser Thr Ala His His Ser Thr Thr Val Thr Gln Thr Pro Ser
                325                 330                 335
His Ser Trp Ser Asn Gly His Thr Glu Ser Ile Leu Ser Glu Ser His
            340                 345                 350
Ser Val Ile Val Met Ser Ser Val Glu Asn Ser Arg His Ser Ser Pro
        355                 360                 365
Thr Gly Gly Pro Arg Gly Arg Leu Asn Gly Thr Gly Gly Pro Arg Glu
    370                 375                 380
Cys Asn Ser Phe Leu Arg His Ala Arg Glu Thr Pro Asp Ser Tyr Arg
385                 390                 395                 400
Asp Ser Pro His Ser Glu Arg Tyr Val Ser Ala Met Thr Thr Pro Ala
                405                 410                 415
Arg Met Ser Pro Val Asp Phe His Thr Pro Ser Ser Pro Lys Ser Pro
            420                 425                 430
Pro Ser Glu Met Ser Pro Pro Val Ser Ser Met Thr Val Ser Met Pro
        435                 440                 445
Ser Met Ala Val Ser Pro Phe Met Glu Glu Glu Arg Pro Leu Leu Leu
        450                 455                 460
Val Thr Pro Pro Arg Leu Arg Glu Lys Lys Phe Asp His His Pro Gln
465                 470                 475                 480
Gln Phe Ser Ser Phe His His Asn Pro Ala His Asp Ser Asn Ser Leu
                485                 490                 495
Pro Ala Ser Pro Leu Arg Ile Val Glu Asp Glu Glu Tyr Glu Thr Thr
            500                 505                 510
Gln Glu Tyr Glu Pro Ala Gln Glu Pro Val Lys Lys Leu Ala Asn Ser
        515                 520                 525
Arg Arg Ala Lys Arg Thr Lys Pro Asn Gly His Ile Ala Asn Arg Leu
530                 535                 540
Glu Val Asp Ser Asn Thr Ser Ser Gln Ser Ser Asn Ser Glu Ser Glu
545                 550                 555                 560
Thr Glu Asp Glu Arg Val Gly Glu Asp Thr Pro Phe Leu Gly Ile Gln
                565                 570                 575
Asn Pro Leu Ala Ala Ser Leu Glu Ala Thr Pro Ala Phe Arg Leu Ala
```

```
                    580             585             590
Asp Ser Arg Thr Asn Pro Ala Gly Arg Phe Ser Thr Gln Glu Glu Ile
        595                 600                 605
Gln Ala Arg Leu Ser Ser Val Ile Ala Asn Gln Asp Pro Ile Ala Val
        610                 615                 620

<210> SEQ ID NO 4
<211> LENGTH: 590
<212> TYPE: PRT
<213> ORGANISM: Homo sapiens

<400> SEQUENCE: 4

Met Gly Lys Gly Arg Ala Gly Arg Val Gly Thr Thr Ala Leu Pro Pro
1               5                   10                  15
Arg Leu Lys Glu Met Lys Ser Gln Glu Ser Ala Ala Gly Ser Lys Leu
            20                  25                  30
Val Leu Arg Cys Glu Thr Ser Ser Glu Tyr Ser Ser Leu Arg Phe Lys
        35                  40                  45
Trp Phe Lys Asn Gly Asn Glu Leu Asn Arg Lys Asn Lys Pro Gln Asn
    50                  55                  60
Ile Lys Ile Gln Lys Lys Pro Gly Lys Ser Glu Leu Arg Ile Asn Lys
65                  70                  75                  80
Ala Ser Leu Ala Asp Ser Gly Glu Tyr Met Cys Lys Val Ile Ser Lys
                85                  90                  95
Leu Gly Asn Asp Ser Ala Ser Ala Asn Ile Thr Ile Val Glu Ser Asn
            100                 105                 110
Ala Thr Ser Thr Ser Thr Thr Gly Thr Ser His Leu Val Lys Cys Ala
        115                 120                 125
Glu Lys Glu Lys Thr Phe Cys Val Asn Gly Gly Glu Cys Phe Met Val
    130                 135                 140
Lys Asp Leu Ser Asn Pro Ser Arg Tyr Leu Cys Lys Cys Pro Asn Glu
145                 150                 155                 160
Phe Thr Gly Asp Arg Cys Gln Asn Tyr Val Met Ala Ser Phe Tyr Lys
                165                 170                 175
His Leu Gly Ile Glu Phe Met Glu Ala Glu Leu Tyr Gln Lys Arg
            180                 185                 190
Val Leu Thr Ile Thr Gly Ile Cys Ile Ala Leu Leu Val Val Gly Ile
        195                 200                 205
Met Cys Val Val Ala Tyr Cys Lys Thr Lys Lys Gln Arg Lys Lys Leu
    210                 215                 220
His Asp Arg Leu Arg Gln Ser Leu Arg Ser Glu Arg Asn Asn Met Met
225                 230                 235                 240
Asn Ile Ala Asn Gly Pro His His Pro Asn Pro Pro Pro Glu Asn Val
                245                 250                 255
Gln Leu Val Asn Gln Tyr Val Ser Lys Asn Val Ile Ser Ser Glu His
            260                 265                 270
Ile Val Glu Arg Glu Ala Glu Thr Ser Phe Ser Thr Ser His Tyr Thr
        275                 280                 285
Ser Thr Ala His His Ser Thr Thr Val Thr Gln Thr Pro Ser His Ser
    290                 295                 300
Trp Ser Asn Gly His Thr Glu Ser Ile Leu Ser Glu Ser His Ser Val
305                 310                 315                 320
Ile Val Met Ser Ser Val Glu Asn Ser Arg His Ser Ser Pro Thr Gly
                325                 330                 335
```

```
Gly Pro Arg Gly Arg Leu Asn Gly Thr Gly Pro Arg Glu Cys Asn
            340                 345                 350

Ser Phe Leu Arg His Ala Arg Glu Thr Pro Asp Ser Tyr Arg Asp Ser
        355                 360                 365

Pro His Ser Glu Arg Tyr Val Ser Ala Met Thr Thr Pro Ala Arg Met
    370                 375                 380

Ser Pro Val Asp Phe His Thr Pro Ser Ser Pro Lys Ser Pro Pro Ser
385                 390                 395                 400

Glu Met Ser Pro Pro Val Ser Ser Met Thr Val Ser Met Pro Ser Met
                405                 410                 415

Ala Val Ser Pro Phe Met Glu Glu Arg Pro Leu Leu Leu Val Thr
            420                 425                 430

Pro Pro Arg Leu Arg Glu Lys Lys Phe Asp His His Pro Gln Gln Phe
    435                 440                 445

Ser Ser Phe His His Asn Pro Ala His Asp Ser Asn Ser Leu Pro Ala
        450                 455                 460

Ser Pro Leu Arg Ile Val Glu Asp Glu Glu Tyr Glu Thr Thr Gln Glu
465                 470                 475                 480

Tyr Glu Pro Ala Gln Glu Pro Val Lys Lys Leu Ala Asn Ser Arg Arg
                485                 490                 495

Ala Lys Arg Thr Lys Pro Asn Gly His Ile Ala Asn Arg Leu Glu Val
            500                 505                 510

Asp Ser Asn Thr Ser Ser Gln Ser Asn Ser Glu Ser Glu Thr Glu
        515                 520                 525

Asp Glu Arg Val Gly Asp Thr Pro Phe Leu Gly Ile Gln Asn Pro
    530                 535                 540

Leu Ala Ala Ser Leu Glu Ala Thr Pro Ala Phe Arg Leu Ala Asp Ser
545                 550                 555                 560

Arg Thr Asn Pro Ala Gly Arg Phe Ser Thr Gln Glu Ile Gln Ala
            565                 570                 575

Arg Leu Ser Ser Val Ile Ala Asn Gln Asp Pro Ile Ala Val
        580                 585                 590

<210> SEQ ID NO 5
<211> LENGTH: 194
<212> TYPE: PRT
<213> ORGANISM: Homo sapiens

<400> SEQUENCE: 5

Met Ser Glu Arg Lys Glu Gly Arg Gly Lys Gly Lys Gly Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125
```

```
Ile Val Glu Ser Asn Glu Ile Ile Thr Gly Met Pro Ala Ser Thr Glu
    130                 135                 140

Gly Ala Tyr Val Ser Ser Ala Thr Ser Thr Ser Thr Thr Gly Thr Ser
145                 150                 155                 160

His Leu Val Lys Cys Ala Glu Lys Glu Lys Thr Phe Cys Val Asn Gly
                165                 170                 175

Gly Glu Cys Phe Met Val Lys Asp Leu Ser Asn Pro Ser Arg Tyr Leu
            180                 185                 190

Cys Lys

<210> SEQ ID NO 6
<211> LENGTH: 459
<212> TYPE: PRT
<213> ORGANISM: Homo sapiens

<400> SEQUENCE: 6

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
    130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
        195                 200                 205

Leu Cys Lys Cys Pro Asn Glu Phe Thr Gly Asp Arg Cys Gln Asn Tyr
    210                 215                 220

Val Met Ala Ser Phe Tyr Lys Ala Glu Glu Leu Tyr Gln Lys Arg Val
225                 230                 235                 240

Leu Thr Ile Thr Gly Ile Cys Ile Ala Leu Leu Val Val Gly Ile Met
                245                 250                 255

Cys Val Val Ala Tyr Cys Lys Thr Lys Lys Gln Arg Lys Lys Leu His
            260                 265                 270

Asp Arg Leu Arg Gln Ser Leu Arg Ser Glu Arg Asn Asn Met Met Asn
        275                 280                 285

Ile Ala Asn Gly Pro His His Pro Asn Pro Pro Pro Glu Asn Val Gln
    290                 295                 300
```

Leu Val Asn Gln Tyr Val Ser Lys Asn Val Ile Ser Glu His Ile
305                 310                 315                 320

Val Glu Arg Glu Ala Glu Thr Ser Phe Ser Thr Ser His Tyr Thr Ser
            325                 330                 335

Thr Ala His His Ser Thr Thr Val Thr Gln Thr Pro Ser His Ser Trp
            340                 345                 350

Ser Asn Gly His Thr Glu Ser Ile Leu Ser Glu Ser His Ser Val Ile
            355                 360                 365

Val Met Ser Ser Val Glu Asn Ser Arg His Ser Ser Pro Thr Gly Gly
370                 375                 380

Pro Arg Gly Arg Leu Asn Gly Thr Gly Gly Pro Arg Glu Cys Asn Ser
385                 390                 395                 400

Phe Leu Arg His Ala Arg Glu Thr Pro Asp Ser Tyr Arg Asp Ser Pro
            405                 410                 415

His Ser Glu Arg His Asn Leu Ile Ala Glu Leu Arg Arg Asn Lys Ala
            420                 425                 430

His Arg Ser Lys Cys Met Gln Ile Gln Leu Ser Ala Thr His Leu Arg
            435                 440                 445

Ser Ser Ser Ile Pro His Leu Gly Phe Ile Leu
            450                 455

<210> SEQ ID NO 7
<211> LENGTH: 207
<212> TYPE: PRT
<213> ORGANISM: Homo sapiens

<400> SEQUENCE: 7

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Ala Thr Ser Thr Ser Thr Thr Gly Thr Ser His
130                 135                 140

Leu Val Lys Cys Ala Glu Lys Glu Lys Thr Phe Cys Val Asn Gly Gly
145                 150                 155                 160

Glu Cys Phe Met Val Lys Asp Leu Ser Asn Pro Ser Arg Tyr Leu Cys
                165                 170                 175

Lys Cys Pro Asn Glu Phe Thr Gly Asp Arg Cys Gln Asn Tyr Val Met
            180                 185                 190

Ala Ser Phe Tyr Ser Thr Ser Thr Pro Phe Leu Ser Leu Pro Glu
        195                 200                 205

-continued

```
<210> SEQ ID NO 8
<211> LENGTH: 177
<212> TYPE: PRT
<213> ORGANISM: Homo sapiens

<400> SEQUENCE: 8

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Ala Thr Ser Thr Ser Thr Thr Gly Thr Ser His
    130                 135                 140

Leu Val Lys Cys Ala Glu Lys Glu Lys Thr Phe Cys Val Asn Gly Gly
145                 150                 155                 160

Glu Cys Phe Met Val Lys Asp Leu Ser Asn Pro Ser Arg Tyr Leu Cys
                165                 170                 175

Lys

<210> SEQ ID NO 9
<211> LENGTH: 420
<212> TYPE: PRT
<213> ORGANISM: Homo sapiens

<400> SEQUENCE: 9

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
    130                 135                 140

Gly Ala Tyr Val Ser Ser Glu Ser Pro Ile Arg Ile Ser Val Ser Thr
145                 150                 155                 160
```

```
Glu Gly Ala Asn Thr Ser Ser Ser Thr Ser Thr Thr Gly Thr
                165                 170                 175

Ser His Leu Val Lys Cys Ala Glu Lys Thr Phe Cys Val Asn
            180                 185                 190

Gly Gly Glu Cys Phe Met Val Lys Asp Leu Ser Asn Pro Ser Arg Tyr
        195                 200                 205

Leu Cys Lys Cys Pro Asn Glu Phe Thr Gly Asp Arg Cys Gln Asn Tyr
    210                 215                 220

Val Met Ala Ser Phe Tyr Lys Ala Glu Glu Leu Tyr Gln Lys Arg Val
225                 230                 235                 240

Leu Thr Ile Thr Gly Ile Cys Ile Ala Leu Leu Val Val Gly Ile Met
                245                 250                 255

Cys Val Val Ala Tyr Cys Lys Thr Lys Lys Gln Arg Lys Lys Leu His
            260                 265                 270

Asp Arg Leu Arg Gln Ser Leu Arg Ser Glu Arg Asn Asn Met Met Asn
        275                 280                 285

Ile Ala Asn Gly Pro His His Pro Asn Pro Pro Pro Glu Asn Val Gln
    290                 295                 300

Leu Val Asn Gln Tyr Val Ser Lys Asn Val Ile Ser Ser Glu His Ile
305                 310                 315                 320

Val Glu Arg Glu Ala Glu Thr Ser Phe Ser Thr Ser His Tyr Thr Ser
                325                 330                 335

Thr Ala His His Ser Thr Thr Val Thr Gln Thr Pro Ser His Ser Trp
            340                 345                 350

Ser Asn Gly His Thr Glu Ser Ile Leu Ser Glu Ser His Ser Val Ile
        355                 360                 365

Val Met Ser Ser Val Glu Asn Ser Arg His Ser Ser Pro Thr Gly Gly
    370                 375                 380

Pro Arg Gly Arg Leu Asn Gly Thr Gly Gly Pro Arg Glu Cys Asn Ser
385                 390                 395                 400

Phe Leu Arg His Ala Arg Glu Thr Pro Asp Ser Tyr Arg Asp Ser Pro
                405                 410                 415

His Ser Glu Arg
            420

<210> SEQ ID NO 10
<211> LENGTH: 211
<212> TYPE: PRT
<213> ORGANISM: Homo sapiens

<400> SEQUENCE: 10

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
```

```
              100                 105                 110
Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
    130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Val Lys Cys Ala Glu Lys Glu Lys Thr Phe Cys Val Asn
                180                 185                 190

Gly Gly Glu Cys Phe Met Val Lys Asp Leu Ser Asn Pro Ser Arg Tyr
            195                 200                 205

Leu Cys Lys
        210

<210> SEQ ID NO 11
<211> LENGTH: 645
<212> TYPE: PRT
<213> ORGANISM: Homo sapiens

<400> SEQUENCE: 11

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
    130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Val Lys Cys Ala Glu Lys Glu Lys Thr Phe Cys Val Asn
                180                 185                 190

Gly Gly Glu Cys Phe Met Val Lys Asp Leu Ser Asn Pro Ser Arg Tyr
            195                 200                 205

Leu Cys Lys Cys Pro Asn Glu Phe Thr Gly Asp Arg Cys Gln Asn Tyr
        210                 215                 220

Val Met Ala Ser Phe Tyr Lys His Leu Gly Ile Glu Phe Met Glu Ala
225                 230                 235                 240

Glu Glu Leu Tyr Gln Lys Arg Val Leu Thr Ile Thr Gly Ile Cys Ile
                245                 250                 255
```

Ala Leu Leu Val Val Gly Ile Met Cys Val Ala Tyr Cys Lys Thr
                260                 265                 270

Lys Lys Gln Arg Lys Lys Leu His Asp Arg Leu Arg Gln Ser Leu Arg
            275                 280                 285

Ser Glu Arg Asn Asn Met Met Asn Ile Ala Asn Gly Pro His His Pro
290                 295                 300

Asn Pro Pro Glu Asn Val Gln Leu Val Asn Gln Tyr Val Ser Lys
305                 310                 315                 320

Asn Val Ile Ser Ser Glu His Ile Val Glu Arg Glu Ala Glu Thr Ser
                325                 330                 335

Phe Ser Thr Ser His Tyr Thr Ser Thr Ala His His Ser Thr Thr Val
                340                 345                 350

Thr Gln Thr Pro Ser His Ser Trp Ser Asn Gly His Thr Glu Ser Ile
            355                 360                 365

Leu Ser Glu Ser His Ser Val Ile Val Met Ser Ser Val Glu Asn Ser
370                 375                 380

Arg His Ser Ser Pro Thr Gly Gly Pro Arg Gly Arg Leu Asn Gly Thr
385                 390                 395                 400

Gly Gly Pro Arg Glu Cys Asn Ser Phe Leu Arg His Ala Arg Glu Thr
                405                 410                 415

Pro Asp Ser Tyr Arg Asp Ser Pro His Ser Glu Arg Tyr Val Ser Ala
                420                 425                 430

Met Thr Thr Pro Ala Arg Met Ser Pro Val Asp Phe His Thr Pro Ser
            435                 440                 445

Ser Pro Lys Ser Pro Pro Ser Glu Met Ser Pro Val Ser Ser Met
450                 455                 460

Thr Val Ser Met Pro Ser Met Ala Val Ser Pro Phe Met Glu Glu Glu
465                 470                 475                 480

Arg Pro Leu Leu Leu Val Thr Pro Pro Arg Leu Arg Glu Lys Lys Phe
                485                 490                 495

Asp His His Pro Gln Gln Phe Ser Ser Phe His His Asn Pro Ala His
                500                 505                 510

Asp Ser Asn Ser Leu Pro Ala Ser Pro Leu Arg Ile Val Glu Asp Glu
            515                 520                 525

Glu Tyr Glu Thr Thr Gln Glu Tyr Glu Pro Ala Gln Glu Pro Val Lys
530                 535                 540

Lys Leu Ala Asn Ser Arg Arg Ala Lys Arg Thr Lys Pro Asn Gly His
545                 550                 555                 560

Ile Ala Asn Arg Leu Glu Val Asp Ser Asn Thr Ser Ser Gln Ser Ser
                565                 570                 575

Asn Ser Glu Ser Glu Thr Glu Asp Glu Arg Val Gly Glu Asp Thr Pro
            580                 585                 590

Phe Leu Gly Ile Gln Asn Pro Leu Ala Ala Ser Leu Glu Ala Thr Pro
            595                 600                 605

Ala Phe Arg Leu Ala Asp Ser Arg Thr Asn Pro Ala Gly Arg Phe Ser
            610                 615                 620

Thr Gln Glu Glu Ile Gln Ala Arg Leu Ser Ser Val Ile Ala Asn Gln
625                 630                 635                 640

Asp Pro Ile Ala Val
                645

<210> SEQ ID NO 12
<211> LENGTH: 637
<212> TYPE: PRT

-continued

<213> ORGANISM: Homo sapiens

<400> SEQUENCE: 12

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
    130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
        195                 200                 205

Leu Cys Lys Cys Pro Asn Glu Phe Thr Gly Asp Arg Cys Gln Asn Tyr
    210                 215                 220

Val Met Ala Ser Phe Tyr Lys Ala Glu Glu Leu Tyr Gln Lys Arg Val
225                 230                 235                 240

Leu Thr Ile Thr Gly Ile Cys Ile Ala Leu Leu Val Val Gly Ile Met
                245                 250                 255

Cys Val Val Ala Tyr Cys Lys Thr Lys Lys Gln Arg Lys Lys Leu His
            260                 265                 270

Asp Arg Leu Arg Gln Ser Leu Arg Ser Glu Arg Asn Asn Met Met Asn
        275                 280                 285

Ile Ala Asn Gly Pro His His Pro Asn Pro Pro Pro Glu Asn Val Gln
    290                 295                 300

Leu Val Asn Gln Tyr Val Ser Lys Asn Val Ile Ser Ser Glu His Ile
305                 310                 315                 320

Val Glu Arg Glu Ala Glu Thr Ser Phe Ser Thr Ser His Tyr Thr Ser
                325                 330                 335

Thr Ala His His Ser Thr Thr Val Thr Gln Thr Pro Ser His Ser Trp
            340                 345                 350

Ser Asn Gly His Thr Glu Ser Ile Leu Ser Glu Ser His Ser Val Ile
        355                 360                 365

Val Met Ser Ser Val Glu Asn Ser Arg His Ser Ser Pro Thr Gly Gly
    370                 375                 380

Pro Arg Gly Arg Leu Asn Gly Thr Gly Gly Pro Arg Glu Cys Asn Ser
385                 390                 395                 400

```
Phe Leu Arg His Ala Arg Glu Thr Pro Asp Ser Tyr Arg Asp Ser Pro
                405                 410                 415

His Ser Glu Arg Tyr Val Ser Ala Met Thr Thr Pro Ala Arg Met Ser
            420                 425                 430

Pro Val Asp Phe His Thr Pro Ser Ser Pro Lys Ser Pro Pro Ser Glu
        435                 440                 445

Met Ser Pro Pro Val Ser Ser Met Thr Val Ser Met Pro Ser Met Ala
    450                 455                 460

Val Ser Pro Phe Met Glu Glu Arg Pro Leu Leu Val Thr Pro
465                 470                 475                 480

Pro Arg Leu Arg Glu Lys Lys Phe Asp His His Pro Gln Gln Phe Ser
                485                 490                 495

Ser Phe His His Asn Pro Ala His Asp Ser Asn Ser Leu Pro Ala Ser
            500                 505                 510

Pro Leu Arg Ile Val Glu Asp Glu Glu Tyr Glu Thr Thr Gln Glu Tyr
        515                 520                 525

Glu Pro Ala Gln Glu Pro Val Lys Lys Leu Ala Asn Ser Arg Arg Ala
    530                 535                 540

Lys Arg Thr Lys Pro Asn Gly His Ile Ala Asn Arg Leu Glu Val Asp
545                 550                 555                 560

Ser Asn Thr Ser Ser Gln Ser Ser Asn Ser Glu Ser Glu Thr Glu Asp
                565                 570                 575

Glu Arg Val Gly Glu Asp Thr Pro Phe Leu Gly Ile Gln Asn Pro Leu
            580                 585                 590

Ala Ala Ser Leu Glu Ala Thr Pro Ala Phe Arg Leu Ala Asp Ser Arg
        595                 600                 605

Thr Asn Pro Ala Gly Arg Phe Ser Thr Gln Glu Glu Ile Gln Ala Arg
    610                 615                 620

Leu Ser Ser Val Ile Ala Asn Gln Asp Pro Ile Ala Val
625                 630                 635

<210> SEQ ID NO 13
<211> LENGTH: 241
<212> TYPE: PRT
<213> ORGANISM: Homo sapiens

<400> SEQUENCE: 13

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
    130                 135                 140
```

Gly Ala Tyr Val Ser Ser Glu Ser Pro Ile Arg Ile Ser Val Ser Thr
145                 150                 155                 160

Glu Gly Ala Asn Thr Ser Ser Thr Ser Thr Ser Thr Thr Gly Thr
                165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
        195                 200                 205

Leu Cys Lys Cys Pro Asn Glu Phe Thr Gly Asp Arg Cys Gln Asn Tyr
    210                 215                 220

Val Met Ala Ser Phe Tyr Ser Thr Ser Thr Pro Phe Leu Ser Leu Pro
225                 230                 235                 240

Glu

<210> SEQ ID NO 14
<211> LENGTH: 296
<212> TYPE: PRT
<213> ORGANISM: Homo sapiens

<400> SEQUENCE: 14

Met Glu Ile Tyr Ser Pro Asp Met Ser Glu Val Ala Ala Glu Arg Ser
1               5                   10                  15

Ser Ser Pro Ser Thr Gln Leu Ser Ala Asp Pro Ser Leu Asp Gly Leu
                20                  25                  30

Pro Ala Ala Glu Asp Met Pro Glu Pro Gln Thr Glu Asp Gly Arg Thr
            35                  40                  45

Pro Gly Leu Val Gly Leu Ala Val Pro Cys Cys Ala Cys Leu Glu Ala
    50                  55                  60

Glu Arg Leu Arg Gly Cys Leu Asn Ser Glu Lys Ile Cys Ile Val Pro
65                  70                  75                  80

Ile Leu Ala Cys Leu Val Ser Leu Cys Leu Cys Ile Ala Gly Leu Lys
                85                  90                  95

Trp Val Phe Val Asp Lys Ile Phe Glu Tyr Asp Ser Pro Thr His Leu
                100                 105                 110

Asp Pro Gly Gly Leu Gly Gln Asp Pro Ile Ile Ser Leu Asp Ala Thr
            115                 120                 125

Ala Ala Ser Ala Val Trp Val Ser Ser Glu Ala Tyr Thr Ser Pro Val
    130                 135                 140

Ser Arg Ala Gln Ser Glu Ser Glu Val Gln Val Thr Val Gln Gly Asp
145                 150                 155                 160

Lys Ala Val Val Ser Phe Glu Pro Ser Ala Ala Pro Thr Pro Lys Asn
                165                 170                 175

Arg Ile Phe Ala Phe Ser Phe Leu Pro Ser Thr Ala Pro Ser Phe Pro
            180                 185                 190

Ser Pro Thr Arg Asn Pro Glu Val Arg Thr Pro Lys Ser Ala Thr Gln
    195                 200                 205

Pro Gln Thr Thr Glu Thr Asn Leu Gln Thr Ala Pro Lys Leu Ser Thr
210                 215                 220

Ser Thr Ser Thr Thr Gly Thr Ser His Leu Val Lys Cys Ala Glu Lys
225                 230                 235                 240

Glu Lys Thr Phe Cys Val Asn Gly Gly Glu Cys Phe Met Val Lys Asp
                245                 250                 255

Leu Ser Asn Pro Ser Arg Tyr Leu Cys Lys Cys Pro Asn Glu Phe Thr
            260                 265                 270

```
Gly Asp Arg Cys Gln Asn Tyr Val Met Ala Ser Phe Tyr Ser Thr Ser
        275                 280                 285

Thr Pro Phe Leu Ser Leu Pro Glu
    290                 295

<210> SEQ ID NO 15
<211> LENGTH: 462
<212> TYPE: PRT
<213> ORGANISM: Homo sapiens

<400> SEQUENCE: 15

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
    130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
        195                 200                 205

Leu Cys Lys Cys Gln Pro Gly Phe Thr Gly Ala Arg Cys Thr Glu Asn
    210                 215                 220

Val Pro Met Lys Val Gln Asn Gln Glu Lys Ala Glu Glu Leu Tyr Gln
225                 230                 235                 240

Lys Arg Val Leu Thr Ile Thr Gly Ile Cys Ile Ala Leu Leu Val Val
                245                 250                 255

Gly Ile Met Cys Val Val Ala Tyr Cys Lys Thr Lys Lys Gln Arg Lys
            260                 265                 270

Lys Leu His Asp Arg Leu Arg Gln Ser Leu Arg Ser Glu Arg Asn Asn
        275                 280                 285

Met Met Asn Ile Ala Asn Gly Pro His His Pro Asn Pro Pro Pro Glu
    290                 295                 300

Asn Val Gln Leu Val Asn Gln Tyr Val Ser Lys Asn Val Ile Ser Ser
305                 310                 315                 320

Glu His Ile Val Glu Arg Glu Ala Glu Thr Ser Phe Ser Thr Ser His
                325                 330                 335

Tyr Thr Ser Thr Ala His His Ser Thr Thr Val Thr Gln Thr Pro Ser
```

```
                340             345             350
His Ser Trp Ser Asn Gly His Thr Glu Ser Ile Leu Ser Glu Ser His
            355             360             365
Ser Val Ile Val Met Ser Val Glu Asn Ser Arg His Ser Ser Pro
        370             375             380
Thr Gly Gly Pro Arg Gly Arg Leu Asn Gly Thr Gly Pro Arg Glu
385             390             395             400
Cys Asn Ser Phe Leu Arg His Ala Arg Glu Thr Pro Asp Ser Tyr Arg
            405             410             415
Asp Ser Pro His Ser Glu Arg His Asn Leu Ile Ala Glu Leu Arg Arg
            420             425             430
Asn Lys Ala His Arg Ser Lys Cys Met Gln Ile Gln Leu Ser Ala Thr
            435             440             445
His Leu Arg Ser Ser Ser Ile Pro His Leu Gly Phe Ile Leu
            450             455             460

<210> SEQ ID NO 16
<211> LENGTH: 422
<212> TYPE: PRT
<213> ORGANISM: Homo sapiens

<400> SEQUENCE: 16

Met Arg Trp Arg Arg Ala Pro Arg Arg Ser Gly Arg Pro Gly Pro Arg
1               5                   10                  15
Ala Gln Arg Pro Gly Ser Ala Ala Arg Ser Ser Pro Leu Pro Leu
            20                  25                  30
Leu Pro Leu Leu Leu Leu Leu Gly Thr Ala Ala Leu Ala Pro Gly Ala
        35                  40                  45
Ala Ala Gly Asn Glu Ala Ala Pro Ala Gly Ala Ser Val Cys Tyr Ser
50                  55                  60
Ser Pro Pro Ser Val Gly Ser Val Gln Glu Leu Ala Gln Arg Ala Ala
65                  70                  75                  80
Val Val Ile Glu Gly Lys Val His Pro Gln Arg Arg Gln Gln Gly Ala
            85                  90                  95
Leu Asp Arg Lys Ala Ala Ala Ala Gly Glu Ala Gly Ala Trp Gly
            100                 105                 110
Gly Asp Arg Glu Pro Pro Ala Ala Gly Pro Arg Ala Leu Gly Pro Pro
        115                 120                 125
Ala Glu Glu Pro Leu Leu Ala Ala Asn Gly Thr Val Pro Ser Trp Pro
130                 135                 140
Thr Ala Pro Val Pro Ser Ala Gly Glu Pro Gly Glu Glu Ala Pro Tyr
145                 150                 155                 160
Leu Val Lys Val His Gln Val Trp Ala Val Lys Ala Gly Gly Leu Lys
            165                 170                 175
Lys Asp Ser Leu Leu Thr Val Arg Leu Gly Thr Trp Gly His Pro Ala
            180                 185                 190
Phe Pro Ser Cys Gly Arg Leu Lys Glu Asp Ser Arg Tyr Ile Phe Phe
        195                 200                 205
Met Glu Pro Asp Ala Asn Ser Thr Ser Arg Ala Pro Ala Ala Phe Arg
210                 215                 220
Ala Ser Phe Pro Pro Leu Glu Thr Gly Arg Asn Leu Lys Lys Glu Val
225                 230                 235                 240
Ser Arg Val Leu Cys Lys Arg Cys Ala Leu Pro Pro Arg Leu Lys Glu
            245                 250                 255
```

-continued

Met Lys Ser Gln Glu Ser Ala Ala Gly Ser Lys Leu Val Leu Arg Cys
                260                 265                 270

Glu Thr Ser Ser Glu Tyr Ser Ser Leu Arg Phe Lys Trp Phe Lys Asn
            275                 280                 285

Gly Asn Glu Leu Asn Arg Lys Asn Lys Pro Gln Asn Ile Lys Ile Gln
        290                 295                 300

Lys Lys Pro Gly Lys Ser Glu Leu Arg Ile Asn Lys Ala Ser Leu Ala
305                 310                 315                 320

Asp Ser Gly Glu Tyr Met Cys Lys Val Ile Ser Lys Leu Gly Asn Asp
                325                 330                 335

Ser Ala Ser Ala Asn Ile Thr Ile Val Glu Ser Asn Ala Thr Ser Thr
            340                 345                 350

Ser Thr Thr Gly Thr Ser His Leu Val Lys Cys Ala Glu Lys Glu Lys
        355                 360                 365

Thr Phe Cys Val Asn Gly Gly Glu Cys Phe Met Val Lys Asp Leu Ser
370                 375                 380

Asn Pro Ser Arg Tyr Leu Cys Lys Cys Pro Asn Glu Phe Thr Gly Asp
385                 390                 395                 400

Arg Cys Gln Asn Tyr Val Met Ala Ser Phe Tyr Ser Thr Ser Thr Pro
                405                 410                 415

Phe Leu Ser Leu Pro Glu
            420

<210> SEQ ID NO 17
<211> LENGTH: 640
<212> TYPE: PRT
<213> ORGANISM: Homo sapiens

<400> SEQUENCE: 17

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
    130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
        195                 200                 205

```
Leu Cys Lys Cys Gln Pro Gly Phe Thr Gly Ala Arg Cys Thr Glu Asn
        210                 215                 220
Val Pro Met Lys Val Gln Asn Gln Glu Lys Ala Glu Glu Leu Tyr Gln
225                 230                 235                 240
Lys Arg Val Leu Thr Ile Thr Gly Ile Cys Ile Ala Leu Leu Val Val
                    245                 250                 255
Gly Ile Met Cys Val Val Ala Tyr Cys Lys Thr Lys Lys Gln Arg Lys
            260                 265                 270
Lys Leu His Asp Arg Leu Arg Gln Ser Leu Arg Ser Glu Arg Asn Asn
        275                 280                 285
Met Met Asn Ile Ala Asn Gly Pro His His Pro Asn Pro Pro Pro Glu
290                 295                 300
Asn Val Gln Leu Val Asn Gln Tyr Val Ser Lys Asn Val Ile Ser Ser
305                 310                 315                 320
Glu His Ile Val Glu Arg Glu Ala Glu Thr Ser Phe Ser Thr Ser His
                    325                 330                 335
Tyr Thr Ser Thr Ala His His Ser Thr Thr Val Thr Gln Thr Pro Ser
            340                 345                 350
His Ser Trp Ser Asn Gly His Thr Glu Ser Ile Leu Ser Glu Ser His
        355                 360                 365
Ser Val Ile Val Met Ser Ser Val Glu Asn Ser Arg His Ser Ser Pro
370                 375                 380
Thr Gly Gly Pro Arg Gly Arg Leu Asn Gly Thr Gly Gly Pro Arg Glu
385                 390                 395                 400
Cys Asn Ser Phe Leu Arg His Ala Arg Glu Thr Pro Asp Ser Tyr Arg
                    405                 410                 415
Asp Ser Pro His Ser Glu Arg Tyr Val Ser Ala Met Thr Thr Pro Ala
            420                 425                 430
Arg Met Ser Pro Val Asp Phe His Thr Pro Ser Ser Pro Lys Ser Pro
        435                 440                 445
Pro Ser Glu Met Ser Pro Pro Val Ser Ser Met Thr Val Ser Met Pro
450                 455                 460
Ser Met Ala Val Ser Pro Phe Met Glu Glu Arg Pro Leu Leu Leu
465                 470                 475                 480
Val Thr Pro Pro Arg Leu Arg Glu Lys Lys Phe Asp His His Pro Gln
                    485                 490                 495
Gln Phe Ser Ser Phe His His Asn Pro Ala His Asp Ser Asn Ser Leu
            500                 505                 510
Pro Ala Ser Pro Leu Arg Ile Val Glu Asp Glu Glu Tyr Glu Thr Thr
        515                 520                 525
Gln Glu Tyr Glu Pro Ala Gln Glu Pro Val Lys Lys Leu Ala Asn Ser
530                 535                 540
Arg Arg Ala Lys Arg Thr Lys Pro Asn Gly His Ile Ala Asn Arg Leu
545                 550                 555                 560
Glu Val Asp Ser Asn Thr Ser Ser Gln Ser Ser Asn Ser Glu Ser Glu
                    565                 570                 575
Thr Glu Asp Glu Arg Val Gly Glu Asp Thr Pro Phe Leu Gly Ile Gln
            580                 585                 590
Asn Pro Leu Ala Ala Ser Leu Glu Ala Thr Pro Ala Phe Arg Leu Ala
        595                 600                 605
Asp Ser Arg Thr Asn Pro Ala Gly Arg Phe Ser Thr Gln Glu Glu Ile
610                 615                 620
```

-continued

Gln Ala Arg Leu Ser Ser Val Ile Ala Asn Gln Asp Pro Ile Ala Val
625                 630                 635                 640

<210> SEQ ID NO 18
<211> LENGTH: 784
<212> TYPE: PRT
<213> ORGANISM: Homo sapiens

<400> SEQUENCE: 18

Met Arg Gln Val Cys Cys Ser Ala Leu Pro Pro Pro Leu Glu Lys
1               5                   10                  15

Gly Arg Cys Ser Ser Tyr Ser Asp Ser Ser Ser Ser Ser Glu Arg
                20                  25                  30

Ser Ser Ser Ser Ser Ser Ser Ser Glu Ser Gly Ser Ser Ser Arg
            35                  40                  45

Ser Ser Ser Asn Asn Ser Ser Ile Ser Arg Pro Ala Ala Pro Pro Glu
50                  55                  60

Pro Arg Pro Gln Gln Gln Pro Gln Pro Arg Ser Pro Ala Ala Arg Arg
65                  70                  75                  80

Ala Ala Ala Arg Ser Arg Ala Ala Ala Gly Gly Met Arg Arg Asp
                85                  90                  95

Pro Ala Pro Gly Phe Ser Met Leu Leu Phe Gly Val Ser Leu Ala Cys
                100                 105                 110

Tyr Ser Pro Ser Leu Lys Ser Val Gln Asp Gln Ala Tyr Lys Ala Pro
                115                 120                 125

Val Val Val Glu Gly Lys Val Gln Gly Leu Val Pro Ala Gly Gly Ser
                130                 135                 140

Ser Ser Asn Ser Thr Arg Glu Pro Pro Ala Ser Gly Arg Val Ala Leu
145                 150                 155                 160

Val Lys Val Leu Asp Lys Trp Pro Leu Arg Ser Gly Gly Leu Gln Arg
                165                 170                 175

Glu Gln Val Ile Ser Val Gly Ser Cys Val Pro Leu Glu Arg Asn Gln
                180                 185                 190

Arg Tyr Ile Phe Phe Leu Glu Pro Thr Glu Gln Pro Leu Val Phe Lys
                195                 200                 205

Thr Ala Phe Ala Pro Leu Asp Thr Asn Gly Lys Asn Leu Lys Lys Glu
                210                 215                 220

Val Gly Lys Ile Leu Cys Thr Asp Cys Ala Thr Arg Pro Lys Leu Lys
225                 230                 235                 240

Lys Met Lys Ser Gln Thr Gly Gln Val Gly Glu Lys Gln Ser Leu Lys
                245                 250                 255

Cys Glu Ala Ala Ala Gly Asn Pro Gln Pro Ser Tyr Arg Trp Phe Lys
                260                 265                 270

Asp Gly Lys Glu Leu Asn Arg Ser Arg Asp Ile Arg Ile Lys Tyr Gly
                275                 280                 285

Asn Gly Arg Lys Asn Ser Arg Leu Gln Phe Asn Lys Val Lys Val Glu
                290                 295                 300

Asp Ala Gly Glu Tyr Val Cys Glu Ala Glu Asn Ile Leu Gly Lys Asp
305                 310                 315                 320

Thr Val Arg Gly Arg Leu Tyr Val Asn Ser Glu Ala Glu Leu Tyr
                325                 330                 335

Gln Lys Arg Val Leu Thr Ile Thr Gly Ile Cys Val Ala Leu Leu Val
                340                 345                 350

Val Gly Ile Val Cys Val Val Ala Tyr Cys Lys Thr Lys Lys Gln Arg
                355                 360                 365

-continued

```
Lys Gln Met His Asn His Leu Arg Gln Asn Met Cys Pro Ala His Gln
    370             375                 380

Asn Arg Ser Leu Ala Asn Gly Pro Ser His Pro Arg Leu Asp Pro Glu
385                 390                 395                 400

Glu Ile Gln Met Ala Asp Tyr Ile Ser Lys Asn Val Pro Ala Thr Asp
                405                 410                 415

His Val Ile Arg Arg Glu Thr Glu Thr Thr Phe Ser Gly Ser His Ser
                420                 425                 430

Cys Ser Pro Ser His His Cys Ser Thr Ala Thr Pro Thr Ser Ser His
                435                 440                 445

Arg His Glu Ser His Thr Trp Ser Leu Glu Arg Ser Glu Ser Leu Thr
    450                 455                 460

Ser Asp Ser Gln Ser Gly Ile Met Leu Ser Ser Val Gly Thr Ser Lys
465                 470                 475                 480

Cys Asn Ser Pro Ala Cys Val Glu Ala Arg Ala Arg Arg Ala Ala Ala
                485                 490                 495

Tyr Asn Leu Glu Glu Arg Arg Ala Thr Ala Pro Pro Tyr His Asp
                500                 505                 510

Ser Val Asp Ser Leu Arg Asp Ser Pro His Ser Glu Arg Tyr Val Ser
    515                 520                 525

Ala Leu Thr Thr Pro Ala Arg Leu Ser Pro Val Asp Phe His Tyr Ser
    530                 535                 540

Leu Ala Thr Gln Val Pro Thr Phe Glu Ile Thr Ser Pro Asn Ser Ala
545                 550                 555                 560

His Ala Val Ser Leu Pro Pro Ala Ala Pro Ile Ser Tyr Arg Leu Ala
                565                 570                 575

Glu Gln Gln Pro Leu Leu Arg His Pro Ala Pro Pro Gly Pro Gly Pro
                580                 585                 590

Gly Pro Gly Pro Gly Pro Gly Pro Gly Ala Asp Met Gln Arg Ser Tyr
    595                 600                 605

Asp Ser Tyr Tyr Tyr Pro Ala Ala Gly Pro Gly Pro Arg Arg Gly Thr
    610                 615                 620

Cys Ala Leu Gly Gly Ser Leu Gly Ser Leu Pro Ala Ser Pro Phe Arg
625                 630                 635                 640

Ile Pro Glu Asp Asp Glu Tyr Glu Thr Thr Gln Glu Cys Ala Pro Pro
                645                 650                 655

Pro Pro Pro Arg Pro Arg Ala Arg Gly Ala Ser Arg Arg Thr Ser Ala
                660                 665                 670

Gly Pro Arg Arg Trp Arg Arg Ser Arg Leu Asn Gly Leu Ala Ala Gln
    675                 680                 685

Arg Ala Arg Ala Ala Arg Asp Ser Leu Ser Leu Ser Ser Gly Ser Gly
    690                 695                 700

Gly Gly Ser Ala Ser Ala Ser Asp Asp Ala Asp Asp Ala Asp Gly
705                 710                 715                 720

Ala Leu Ala Ala Glu Ser Thr Pro Phe Leu Gly Leu Arg Gly Ala His
                725                 730                 735

Asp Ala Leu Arg Ser Asp Ser Pro Pro Leu Cys Pro Ala Ala Asp Ser
                740                 745                 750

Arg Thr Tyr Tyr Ser Leu Asp Ser His Ser Thr Arg Ala Ser Ser Arg
    755                 760                 765

His Ser Arg Gly Pro Pro Arg Ala Lys Gln Asp Ser Ala Pro Leu
    770                 775                 780
```

<210> SEQ ID NO 19
<211> LENGTH: 850
<212> TYPE: PRT
<213> ORGANISM: Homo sapiens

<400> SEQUENCE: 19

```
Met Arg Gln Val Cys Cys Ser Ala Leu Pro Pro Pro Leu Glu Lys
1               5                   10                  15

Gly Arg Cys Ser Ser Tyr Ser Asp Ser Ser Ser Ser Ser Glu Arg
                20                  25                  30

Ser Ser Ser Ser Ser Ser Ser Ser Glu Ser Gly Ser Ser Ser Arg
            35                  40                  45

Ser Ser Ser Asn Asn Ser Ser Ile Ser Arg Pro Ala Ala Pro Glu
50                  55                  60

Pro Arg Pro Gln Gln Gln Pro Gln Pro Arg Ser Pro Ala Ala Arg Arg
65                  70                  75                  80

Ala Ala Ala Arg Ser Arg Ala Ala Ala Ala Gly Gly Met Arg Arg Asp
                85                  90                  95

Pro Ala Pro Gly Phe Ser Met Leu Leu Phe Gly Val Ser Leu Ala Cys
                100                 105                 110

Tyr Ser Pro Ser Leu Lys Ser Val Gln Asp Gln Ala Tyr Lys Ala Pro
                115                 120                 125

Val Val Val Glu Gly Lys Val Gln Gly Leu Val Pro Ala Gly Gly Ser
130                 135                 140

Ser Ser Asn Ser Thr Arg Glu Pro Pro Ala Ser Gly Arg Val Ala Leu
145                 150                 155                 160

Val Lys Val Leu Asp Lys Trp Pro Leu Arg Ser Gly Gly Leu Gln Arg
                165                 170                 175

Glu Gln Val Ile Ser Val Gly Ser Cys Val Pro Leu Glu Arg Asn Gln
                180                 185                 190

Arg Tyr Ile Phe Phe Leu Glu Pro Thr Glu Gln Pro Leu Val Phe Lys
                195                 200                 205

Thr Ala Phe Ala Pro Leu Asp Thr Asn Gly Lys Asn Leu Lys Lys Glu
210                 215                 220

Val Gly Lys Ile Leu Cys Thr Asp Cys Ala Thr Arg Pro Lys Leu Lys
225                 230                 235                 240

Lys Met Lys Ser Gln Thr Gly Gln Val Gly Glu Lys Gln Ser Leu Lys
                245                 250                 255

Cys Glu Ala Ala Ala Gly Asn Pro Gln Pro Ser Tyr Arg Trp Phe Lys
                260                 265                 270

Asp Gly Lys Glu Leu Asn Arg Ser Arg Asp Ile Arg Ile Lys Tyr Gly
                275                 280                 285

Asn Gly Arg Lys Asn Ser Arg Leu Gln Phe Asn Lys Val Lys Val Glu
                290                 295                 300

Asp Ala Gly Glu Tyr Val Cys Glu Ala Glu Asn Ile Leu Gly Lys Asp
305                 310                 315                 320

Thr Val Arg Gly Arg Leu Tyr Val Asn Ser Val Ser Thr Thr Leu Ser
                325                 330                 335

Ser Trp Ser Gly His Ala Arg Lys Cys Asn Glu Thr Ala Lys Ser Tyr
                340                 345                 350

Cys Val Asn Gly Gly Val Cys Tyr Tyr Ile Glu Gly Ile Asn Gln Leu
                355                 360                 365

Ser Cys Lys Cys Pro Asn Gly Phe Phe Gly Gln Arg Cys Leu Glu Lys
370                 375                 380
```

```
Leu Pro Leu Arg Leu Tyr Met Pro Asp Pro Lys Gln Lys Ala Glu Glu
385                 390                 395                 400

Leu Tyr Gln Lys Arg Val Leu Thr Ile Thr Gly Ile Cys Val Ala Leu
            405                 410                 415

Leu Val Val Gly Ile Val Cys Val Ala Tyr Cys Lys Thr Lys Lys
        420                 425                 430

Gln Arg Lys Gln Met His Asn His Leu Arg Gln Asn Met Cys Pro Ala
            435                 440                 445

His Gln Asn Arg Ser Leu Ala Asn Gly Pro Ser His Pro Arg Leu Asp
            450                 455                 460

Pro Glu Glu Ile Gln Met Ala Asp Tyr Ile Ser Lys Asn Val Pro Ala
465                 470                 475                 480

Thr Asp His Val Ile Arg Arg Glu Thr Glu Thr Thr Phe Ser Gly Ser
            485                 490                 495

His Ser Cys Ser Pro Ser His His Cys Ser Thr Ala Thr Pro Thr Ser
            500                 505                 510

Ser His Arg His Glu Ser His Thr Trp Ser Leu Glu Arg Ser Glu Ser
            515                 520                 525

Leu Thr Ser Asp Ser Gln Ser Gly Ile Met Leu Ser Ser Val Gly Thr
530                 535                 540

Ser Lys Cys Asn Ser Pro Ala Cys Val Glu Ala Arg Ala Arg Arg Ala
545                 550                 555                 560

Ala Ala Tyr Asn Leu Glu Arg Arg Arg Ala Thr Ala Pro Pro Tyr
            565                 570                 575

His Asp Ser Val Asp Ser Leu Arg Asp Ser Pro His Ser Glu Arg Tyr
            580                 585                 590

Val Ser Ala Leu Thr Thr Pro Ala Arg Leu Ser Pro Val Asp Phe His
            595                 600                 605

Tyr Ser Leu Ala Thr Gln Val Pro Thr Phe Glu Ile Thr Ser Pro Asn
            610                 615                 620

Ser Ala His Ala Val Ser Leu Pro Pro Ala Ala Pro Ile Ser Tyr Arg
625                 630                 635                 640

Leu Ala Glu Gln Gln Pro Leu Leu Arg His Pro Ala Pro Pro Gly Pro
            645                 650                 655

Gly Pro Gly Pro Gly Pro Gly Pro Gly Pro Gly Ala Asp Met Gln Arg
            660                 665                 670

Ser Tyr Asp Ser Tyr Tyr Pro Ala Ala Gly Pro Gly Pro Arg Arg
            675                 680                 685

Gly Thr Cys Ala Leu Gly Gly Ser Leu Gly Ser Leu Pro Ala Ser Pro
            690                 695                 700

Phe Arg Ile Pro Glu Asp Asp Glu Tyr Glu Thr Thr Gln Glu Cys Ala
705                 710                 715                 720

Pro Pro Pro Pro Arg Pro Ala Arg Gly Ala Ser Arg Thr
                725                 730                 735

Ser Ala Gly Pro Arg Arg Trp Arg Arg Ser Arg Leu Asn Gly Leu Ala
            740                 745                 750

Ala Gln Arg Ala Arg Ala Ala Arg Asp Ser Leu Ser Leu Ser Ser Gly
            755                 760                 765

Ser Gly Gly Gly Ser Ala Ser Ala Ser Asp Asp Ala Asp Asp Ala
            770                 775                 780

Asp Gly Ala Leu Ala Ala Glu Ser Thr Pro Phe Leu Gly Leu Arg Gly
785                 790                 795                 800
```

```
Ala His Asp Ala Leu Arg Ser Asp Ser Pro Pro Leu Cys Pro Ala Ala
                805                 810                 815

Asp Ser Arg Thr Tyr Tyr Ser Leu Asp Ser His Ser Thr Arg Ala Ser
            820                 825                 830

Ser Arg His Ser Arg Gly Pro Pro Arg Ala Lys Gln Asp Ser Ala
        835                 840                 845

Pro Leu
    850

<210> SEQ ID NO 20
<211> LENGTH: 844
<212> TYPE: PRT
<213> ORGANISM: Homo sapiens

<400> SEQUENCE: 20

Met Arg Gln Val Cys Cys Ser Ala Leu Pro Pro Pro Leu Glu Lys
1               5                   10                  15

Gly Arg Cys Ser Ser Tyr Ser Asp Ser Ser Ser Ser Ser Glu Arg
                20                  25                  30

Ser Ser Ser Ser Ser Ser Ser Ser Glu Ser Gly Ser Ser Ser Arg
            35                  40                  45

Ser Ser Ser Asn Asn Ser Ser Ile Ser Arg Pro Ala Ala Pro Glu
50                  55                  60

Pro Arg Pro Gln Gln Gln Pro Gln Pro Arg Ser Pro Ala Ala Arg Arg
65                  70                  75                  80

Ala Ala Ala Arg Ser Arg Ala Ala Ala Gly Gly Met Arg Arg Asp
                85                  90                  95

Pro Ala Pro Gly Phe Ser Met Leu Leu Phe Gly Val Ser Leu Ala Cys
                100                 105                 110

Tyr Ser Pro Ser Leu Lys Ser Val Gln Asp Gln Ala Tyr Lys Ala Pro
                115                 120                 125

Val Val Val Glu Gly Lys Val Gln Gly Leu Val Pro Ala Gly Gly Ser
            130                 135                 140

Ser Ser Asn Ser Thr Arg Glu Pro Pro Ala Ser Gly Arg Val Ala Leu
145                 150                 155                 160

Val Lys Val Leu Asp Lys Trp Pro Leu Arg Ser Gly Gly Leu Gln Arg
                165                 170                 175

Glu Gln Val Ile Ser Val Gly Ser Cys Val Pro Leu Glu Arg Asn Gln
                180                 185                 190

Arg Tyr Ile Phe Phe Leu Glu Pro Thr Glu Gln Pro Leu Val Phe Lys
            195                 200                 205

Thr Ala Phe Ala Pro Leu Asp Thr Asn Gly Lys Asn Leu Lys Lys Glu
        210                 215                 220

Val Gly Lys Ile Leu Cys Thr Asp Cys Ala Thr Arg Pro Lys Leu Lys
225                 230                 235                 240

Lys Met Lys Ser Gln Thr Gly Gln Val Gly Glu Lys Gln Ser Leu Lys
                245                 250                 255

Cys Glu Ala Ala Ala Gly Asn Pro Gln Pro Ser Tyr Arg Trp Phe Lys
                260                 265                 270

Asp Gly Lys Glu Leu Asn Arg Ser Arg Asp Ile Arg Ile Lys Tyr Gly
            275                 280                 285

Asn Gly Arg Lys Asn Ser Arg Leu Gln Phe Asn Lys Val Lys Val Glu
        290                 295                 300

Asp Ala Gly Glu Tyr Val Cys Glu Ala Glu Asn Ile Leu Gly Lys Asp
305                 310                 315                 320
```

```
Thr Val Arg Gly Arg Leu Tyr Val Asn Ser Val Ser Thr Thr Leu Ser
            325                 330                 335

Ser Trp Ser Gly His Ala Arg Lys Cys Asn Glu Thr Ala Lys Ser Tyr
            340                 345                 350

Cys Val Asn Gly Val Cys Tyr Tyr Ile Glu Gly Ile Asn Gln Leu
            355                 360                 365

Ser Cys Lys Cys Pro Val Gly Tyr Thr Gly Asp Arg Cys Gln Gln Phe
    370                 375                 380

Ala Met Val Asn Phe Ser Lys Ala Glu Glu Leu Tyr Gln Lys Arg Val
385                 390                 395                 400

Leu Thr Ile Thr Gly Ile Cys Val Ala Leu Leu Val Val Gly Ile Val
                405                 410                 415

Cys Val Val Ala Tyr Cys Lys Thr Lys Lys Gln Arg Lys Gln Met His
                420                 425                 430

Asn His Leu Arg Gln Asn Met Cys Pro Ala His Gln Asn Arg Ser Leu
            435                 440                 445

Ala Asn Gly Pro Ser His Pro Arg Leu Asp Pro Glu Glu Ile Gln Met
    450                 455                 460

Ala Asp Tyr Ile Ser Lys Asn Val Pro Ala Thr Asp His Val Ile Arg
465                 470                 475                 480

Arg Glu Thr Glu Thr Thr Phe Ser Gly Ser His Ser Cys Ser Pro Ser
                485                 490                 495

His His Cys Ser Thr Ala Thr Pro Thr Ser Ser His Arg His Glu Ser
            500                 505                 510

His Thr Trp Ser Leu Glu Arg Ser Glu Ser Leu Thr Ser Asp Ser Gln
            515                 520                 525

Ser Gly Ile Met Leu Ser Ser Val Gly Thr Ser Lys Cys Asn Ser Pro
    530                 535                 540

Ala Cys Val Glu Ala Arg Ala Arg Arg Ala Ala Ala Tyr Asn Leu Glu
545                 550                 555                 560

Glu Arg Arg Arg Ala Thr Ala Pro Pro Tyr His Asp Ser Val Asp Ser
                565                 570                 575

Leu Arg Asp Ser Pro His Ser Glu Arg Tyr Val Ser Ala Leu Thr Thr
            580                 585                 590

Pro Ala Arg Leu Ser Pro Val Asp Phe His Tyr Ser Leu Ala Thr Gln
    595                 600                 605

Val Pro Thr Phe Glu Ile Thr Ser Pro Asn Ser Ala His Ala Val Ser
    610                 615                 620

Leu Pro Pro Ala Ala Pro Ile Ser Tyr Arg Leu Ala Glu Gln Gln Pro
625                 630                 635                 640

Leu Leu Arg His Pro Ala Pro Pro Gly Pro Gly Pro Gly Pro Gly Pro
                645                 650                 655

Gly Pro Gly Pro Gly Ala Asp Met Gln Arg Ser Tyr Asp Ser Tyr Tyr
            660                 665                 670

Tyr Pro Ala Ala Gly Pro Gly Pro Arg Arg Gly Thr Cys Ala Leu Gly
            675                 680                 685

Gly Ser Leu Gly Ser Leu Pro Ala Ser Pro Phe Arg Ile Pro Glu Asp
    690                 695                 700

Asp Glu Tyr Glu Thr Thr Gln Glu Cys Ala Pro Pro Pro Pro Arg
705                 710                 715                 720

Pro Arg Ala Arg Gly Ala Ser Arg Arg Thr Ser Ala Gly Pro Arg Arg
                725                 730                 735
```

```
Trp Arg Arg Ser Arg Leu Asn Gly Leu Ala Ala Gln Arg Ala Arg Ala
                740                 745                 750

Ala Arg Asp Ser Leu Ser Leu Ser Ser Gly Ser Gly Gly Gly Ser Ala
                755                 760                 765

Ser Ala Ser Asp Asp Ala Asp Asp Ala Asp Gly Ala Leu Ala Ala
            770                 775                 780

Glu Ser Thr Pro Phe Leu Gly Leu Arg Gly Ala His Asp Ala Leu Arg
785                 790                 795                 800

Ser Asp Ser Pro Pro Leu Cys Pro Ala Ala Asp Ser Arg Thr Tyr Tyr
                805                 810                 815

Ser Leu Asp Ser His Ser Thr Arg Ala Ser Ser Arg His Ser Arg Gly
                820                 825                 830

Pro Pro Pro Arg Ala Lys Gln Asp Ser Ala Pro Leu
                835                 840

<210> SEQ ID NO 21
<211> LENGTH: 858
<212> TYPE: PRT
<213> ORGANISM: Homo sapiens

<400> SEQUENCE: 21

Met Arg Gln Val Cys Cys Ser Ala Leu Pro Pro Pro Leu Glu Lys
1               5                   10                  15

Gly Arg Cys Ser Ser Tyr Ser Asp Ser Ser Ser Ser Ser Glu Arg
                20                  25                  30

Ser Ser Ser Ser Ser Ser Ser Ser Glu Ser Gly Ser Ser Ser Arg
                35                  40                  45

Ser Ser Ser Asn Asn Ser Ser Ile Ser Arg Pro Ala Ala Pro Pro Glu
50                  55                  60

Pro Arg Pro Gln Gln Pro Gln Pro Arg Ser Pro Ala Ala Arg Arg
65                  70                  75                  80

Ala Ala Ala Arg Ser Arg Ala Ala Ala Gly Gly Met Arg Arg Asp
                85                  90                  95

Pro Ala Pro Gly Phe Ser Met Leu Leu Phe Gly Val Ser Leu Ala Cys
                100                 105                 110

Tyr Ser Pro Ser Leu Lys Ser Val Gln Asp Gln Ala Tyr Lys Ala Pro
                115                 120                 125

Val Val Glu Gly Lys Val Gln Gly Leu Val Pro Ala Gly Gly Ser
            130                 135                 140

Ser Ser Asn Ser Thr Arg Glu Pro Pro Ala Ser Gly Arg Val Ala Leu
145                 150                 155                 160

Val Lys Val Leu Asp Lys Trp Pro Leu Arg Ser Gly Gly Leu Gln Arg
                165                 170                 175

Glu Gln Val Ile Ser Val Gly Ser Cys Val Pro Leu Glu Arg Asn Gln
                180                 185                 190

Arg Tyr Ile Phe Phe Leu Glu Pro Thr Glu Gln Pro Leu Val Phe Lys
                195                 200                 205

Thr Ala Phe Ala Pro Leu Asp Thr Asn Gly Lys Asn Leu Lys Lys Glu
            210                 215                 220

Val Gly Lys Ile Leu Cys Thr Asp Cys Ala Thr Arg Pro Lys Leu Lys
225                 230                 235                 240

Lys Met Lys Ser Gln Thr Gly Gln Val Gly Glu Lys Gln Ser Leu Lys
                245                 250                 255

Cys Glu Ala Ala Ala Gly Asn Pro Gln Pro Ser Tyr Arg Trp Phe Lys
                260                 265                 270
```

```
Asp Gly Lys Glu Leu Asn Arg Ser Arg Asp Ile Arg Ile Lys Tyr Gly
        275                 280                 285

Asn Gly Arg Lys Asn Ser Arg Leu Gln Phe Asn Lys Val Lys Val Glu
    290                 295                 300

Asp Ala Gly Glu Tyr Val Cys Glu Ala Glu Asn Ile Leu Gly Lys Asp
305                 310                 315                 320

Thr Val Arg Gly Arg Leu Tyr Val Asn Ser Val Ser Thr Thr Leu Ser
                325                 330                 335

Ser Trp Ser Gly His Ala Arg Lys Cys Asn Glu Thr Ala Lys Ser Tyr
                340                 345                 350

Cys Val Asn Gly Gly Val Cys Tyr Tyr Ile Glu Gly Ile Asn Gln Leu
                355                 360                 365

Ser Cys Lys Cys Pro Asn Gly Phe Phe Gly Gln Arg Cys Leu Glu Lys
        370                 375                 380

Leu Pro Leu Arg Leu Tyr Met Pro Asp Pro Lys Gln Lys His Leu Gly
385                 390                 395                 400

Phe Glu Leu Lys Glu Ala Glu Leu Tyr Gln Lys Arg Val Leu Thr
                405                 410                 415

Ile Thr Gly Ile Cys Val Ala Leu Leu Val Val Gly Ile Val Cys Val
                420                 425                 430

Val Ala Tyr Cys Lys Thr Lys Lys Gln Arg Lys Gln Met His Asn His
                435                 440                 445

Leu Arg Gln Asn Met Cys Pro Ala His Gln Asn Arg Ser Leu Ala Asn
        450                 455                 460

Gly Pro Ser His Pro Arg Leu Asp Pro Glu Glu Ile Gln Met Ala Asp
465                 470                 475                 480

Tyr Ile Ser Lys Asn Val Pro Ala Thr Asp His Val Ile Arg Arg Glu
                485                 490                 495

Thr Glu Thr Thr Phe Ser Gly Ser His Ser Cys Ser Pro Ser His His
                500                 505                 510

Cys Ser Thr Ala Thr Pro Thr Ser Ser His Arg His Glu Ser His Thr
            515                 520                 525

Trp Ser Leu Glu Arg Ser Glu Ser Leu Thr Ser Asp Ser Gln Ser Gly
        530                 535                 540

Ile Met Leu Ser Ser Val Gly Thr Ser Lys Cys Asn Ser Pro Ala Cys
545                 550                 555                 560

Val Glu Ala Arg Ala Arg Arg Ala Ala Ala Tyr Asn Leu Glu Glu Arg
                565                 570                 575

Arg Arg Ala Thr Ala Pro Pro Tyr His Asp Ser Val Asp Ser Leu Arg
            580                 585                 590

Asp Ser Pro His Ser Glu Arg Tyr Val Ser Ala Leu Thr Thr Pro Ala
            595                 600                 605

Arg Leu Ser Pro Val Asp Phe His Tyr Ser Leu Ala Thr Gln Val Pro
610                 615                 620

Thr Phe Glu Ile Thr Ser Pro Asn Ser Ala His Ala Val Ser Leu Pro
625                 630                 635                 640

Pro Ala Ala Pro Ile Ser Tyr Arg Leu Ala Glu Gln Gln Pro Leu Leu
                645                 650                 655

Arg His Pro Ala Pro Pro Gly Pro Gly Pro Gly Pro Gly Pro Gly Pro
            660                 665                 670

Gly Pro Gly Ala Asp Met Gln Arg Ser Tyr Asp Ser Tyr Tyr Tyr Pro
        675                 680                 685
```

```
Ala Ala Gly Pro Gly Pro Arg Arg Gly Thr Cys Ala Leu Gly Gly Ser
        690                 695                 700

Leu Gly Ser Leu Pro Ala Ser Pro Phe Arg Ile Pro Glu Asp Asp Glu
705                 710                 715                 720

Tyr Glu Thr Thr Gln Glu Cys Ala Pro Pro Pro Arg Pro Arg
                725                 730                 735

Ala Arg Gly Ala Ser Arg Arg Thr Ser Ala Gly Pro Arg Arg Trp Arg
                740                 745                 750

Arg Ser Arg Leu Asn Gly Leu Ala Gln Arg Ala Arg Ala Ala Arg
            755                 760                 765

Asp Ser Leu Ser Leu Ser Ser Gly Ser Gly Gly Ser Ala Ser Ala
770                 775                 780

Ser Asp Asp Asp Ala Asp Ala Asp Gly Ala Leu Ala Ala Glu Ser
785                 790                 795                 800

Thr Pro Phe Leu Gly Leu Arg Gly Ala His Asp Ala Leu Arg Ser Asp
                805                 810                 815

Ser Pro Pro Leu Cys Pro Ala Ala Asp Ser Arg Thr Tyr Tyr Ser Leu
                820                 825                 830

Asp Ser His Ser Thr Arg Ala Ser Ser Arg His Ser Arg Gly Pro Pro
            835                 840                 845

Pro Arg Ala Lys Gln Asp Ser Ala Pro Leu
850                 855

<210> SEQ ID NO 22
<211> LENGTH: 852
<212> TYPE: PRT
<213> ORGANISM: Homo sapiens

<400> SEQUENCE: 22

Met Arg Gln Val Cys Cys Ser Ala Leu Pro Pro Pro Leu Glu Lys
1               5                   10                  15

Gly Arg Cys Ser Ser Tyr Ser Asp Ser Ser Ser Ser Ser Glu Arg
                20                  25                  30

Ser Ser Ser Ser Ser Ser Ser Glu Ser Gly Ser Ser Ser Arg
            35                  40                  45

Ser Ser Ser Asn Asn Ser Ser Ile Ser Arg Pro Ala Ala Pro Pro Glu
50                  55                  60

Pro Arg Pro Gln Gln Gln Pro Gln Pro Arg Ser Pro Ala Ala Arg Arg
65                  70                  75                  80

Ala Ala Ala Arg Ser Arg Ala Ala Ala Gly Gly Met Arg Arg Asp
                85                  90                  95

Pro Ala Pro Gly Phe Ser Met Leu Leu Phe Gly Val Ser Leu Ala Cys
                100                 105                 110

Tyr Ser Pro Ser Leu Lys Ser Val Gln Asp Gln Ala Tyr Lys Ala Pro
            115                 120                 125

Val Val Val Glu Gly Lys Val Gln Gly Leu Val Pro Ala Gly Gly Ser
            130                 135                 140

Ser Ser Asn Ser Thr Arg Glu Pro Pro Ala Ser Gly Arg Val Ala Leu
145                 150                 155                 160

Val Lys Val Leu Asp Lys Trp Pro Leu Arg Ser Gly Gly Leu Gln Arg
                165                 170                 175

Glu Gln Val Ile Ser Val Gly Ser Cys Val Pro Leu Glu Arg Asn Gln
            180                 185                 190

Arg Tyr Ile Phe Phe Leu Glu Pro Thr Glu Gln Pro Leu Val Phe Lys
            195                 200                 205
```

```
Thr Ala Phe Ala Pro Leu Asp Thr Asn Gly Lys Asn Leu Lys Lys Glu
        210                 215                 220
Val Gly Lys Ile Leu Cys Thr Asp Cys Ala Thr Arg Pro Lys Leu Lys
225                 230                 235                 240
Lys Met Lys Ser Gln Thr Gly Gln Val Gly Glu Lys Gln Ser Leu Lys
                245                 250                 255
Cys Glu Ala Ala Ala Gly Asn Pro Gln Pro Ser Tyr Arg Trp Phe Lys
            260                 265                 270
Asp Gly Lys Glu Leu Asn Arg Ser Arg Asp Ile Arg Ile Lys Tyr Gly
        275                 280                 285
Asn Gly Arg Lys Asn Ser Arg Leu Gln Phe Asn Lys Val Lys Val Glu
    290                 295                 300
Asp Ala Gly Glu Tyr Val Cys Glu Ala Glu Asn Ile Leu Gly Lys Asp
305                 310                 315                 320
Thr Val Arg Gly Arg Leu Tyr Val Asn Ser Val Ser Thr Thr Leu Ser
                325                 330                 335
Ser Trp Ser Gly His Ala Arg Lys Cys Asn Glu Thr Ala Lys Ser Tyr
            340                 345                 350
Cys Val Asn Gly Gly Val Cys Tyr Tyr Ile Glu Gly Ile Asn Gln Leu
        355                 360                 365
Ser Cys Lys Cys Pro Val Gly Tyr Thr Gly Asp Arg Cys Gln Gln Phe
    370                 375                 380
Ala Met Val Asn Phe Ser Lys His Leu Gly Phe Glu Leu Lys Glu Ala
385                 390                 395                 400
Glu Glu Leu Tyr Gln Lys Arg Val Leu Thr Ile Thr Gly Ile Cys Val
                405                 410                 415
Ala Leu Leu Val Val Gly Ile Val Cys Val Val Ala Tyr Cys Lys Thr
            420                 425                 430
Lys Lys Gln Arg Lys Gln Met His Asn His Leu Arg Gln Asn Met Cys
        435                 440                 445
Pro Ala His Gln Asn Arg Ser Leu Ala Asn Gly Pro Ser His Pro Arg
    450                 455                 460
Leu Asp Pro Glu Glu Ile Gln Met Ala Asp Tyr Ile Ser Lys Asn Val
465                 470                 475                 480
Pro Ala Thr Asp His Val Ile Arg Arg Glu Thr Glu Thr Thr Phe Ser
                485                 490                 495
Gly Ser His Ser Cys Ser Pro Ser His His Cys Ser Thr Ala Thr Pro
            500                 505                 510
Thr Ser His Arg His Glu Ser His Thr Trp Ser Leu Glu Arg Ser
        515                 520                 525
Glu Ser Leu Thr Ser Asp Ser Gln Ser Gly Ile Met Leu Ser Ser Val
    530                 535                 540
Gly Thr Ser Lys Cys Asn Ser Pro Ala Cys Val Glu Ala Arg Ala Arg
545                 550                 555                 560
Arg Ala Ala Ala Tyr Asn Leu Glu Glu Arg Arg Arg Ala Thr Ala Pro
                565                 570                 575
Pro Tyr His Asp Ser Val Asp Ser Leu Arg Asp Ser Pro His Ser Glu
            580                 585                 590
Arg Tyr Val Ser Ala Leu Thr Thr Pro Ala Arg Leu Ser Pro Val Asp
        595                 600                 605
Phe His Tyr Ser Leu Ala Thr Gln Val Pro Thr Phe Glu Ile Thr Ser
    610                 615                 620
```

```
Pro Asn Ser Ala His Ala Val Ser Leu Pro Pro Ala Pro Ile Ser
625                 630                 635                 640

Tyr Arg Leu Ala Glu Gln Gln Pro Leu Leu Arg His Pro Ala Pro Pro
            645                 650                 655

Gly Pro Gly Pro Gly Pro Gly Pro Gly Pro Gly Pro Gly Ala Asp Met
                660                 665                 670

Gln Arg Ser Tyr Asp Ser Tyr Tyr Pro Ala Ala Gly Pro Gly Pro
            675                 680                 685

Arg Arg Gly Thr Cys Ala Leu Gly Gly Ser Leu Ser Leu Pro Ala
690                 695                 700

Ser Pro Phe Arg Ile Pro Glu Asp Asp Glu Tyr Glu Thr Thr Gln Glu
705                 710                 715                 720

Cys Ala Pro Pro Pro Pro Arg Pro Arg Ala Arg Gly Ala Ser Arg
            725                 730                 735

Arg Thr Ser Ala Gly Pro Arg Arg Trp Arg Arg Ser Arg Leu Asn Gly
            740                 745                 750

Leu Ala Ala Gln Arg Ala Arg Ala Ala Arg Asp Ser Leu Ser Leu Ser
            755                 760                 765

Ser Gly Ser Gly Gly Gly Ser Ala Ser Ala Ser Asp Asp Asp Ala Asp
770                 775                 780

Asp Ala Asp Gly Ala Leu Ala Ala Glu Ser Thr Pro Phe Leu Gly Leu
785                 790                 795                 800

Arg Gly Ala His Asp Ala Leu Arg Ser Asp Ser Pro Leu Cys Pro
            805                 810                 815

Ala Ala Asp Ser Arg Thr Tyr Tyr Ser Leu Asp Ser His Ser Thr Arg
            820                 825                 830

Ala Ser Ser Arg His Ser Arg Gly Pro Pro Pro Arg Ala Lys Gln Asp
            835                 840                 845

Ser Ala Pro Leu
850

<210> SEQ ID NO 23
<211> LENGTH: 696
<212> TYPE: PRT
<213> ORGANISM: Homo sapiens

<400> SEQUENCE: 23

Met Ser Glu Gly Ala Ala Ala Ser Pro Gly Ala Ala Ser Ala
1               5                   10                  15

Ala Ala Ser Ala Glu Glu Gly Thr Ala Ala Ala Ala Ala
            20                  25                  30

Ala Ala Gly Gly Gly Pro Asp Gly Gly Gly Glu Gly Ala Ala Glu Pro
            35                  40                  45

Pro Arg Glu Leu Arg Cys Ser Asp Cys Ile Val Trp Asn Arg Gln Gln
        50                  55                  60

Thr Trp Leu Cys Val Val Pro Leu Phe Ile Gly Phe Ile Gly Leu Gly
65                  70                  75                  80

Leu Ser Leu Met Leu Leu Lys Trp Ile Val Val Gly Ser Val Lys Glu
                85                  90                  95

Tyr Val Pro Thr Asp Leu Val Asp Ser Lys Gly Met Gly Gln Asp Pro
            100                 105                 110

Phe Phe Leu Ser Lys Pro Ser Ser Phe Pro Lys Ala Met Glu Thr Thr
        115                 120                 125

Thr Thr Thr Thr Ser Thr Thr Ser Pro Ala Thr Pro Ser Ala Gly Gly
        130                 135                 140
```

```
Ala Ala Ser Ser Arg Thr Pro Asn Arg Ile Ser Thr Arg Leu Thr Thr
145                 150                 155                 160

Ile Thr Arg Ala Pro Thr Arg Phe Pro Gly His Arg Val Pro Ile Arg
            165                 170                 175

Ala Ser Pro Arg Ser Thr Thr Ala Arg Asn Thr Ala Ala Pro Ala Thr
            180                 185                 190

Val Pro Ser Thr Thr Ala Pro Phe Phe Ser Ser Thr Leu Gly Ser
        195                 200                 205

Arg Pro Pro Val Pro Gly Thr Pro Ser Thr Gln Ala Met Pro Ser Trp
210                 215                 220

Pro Thr Ala Ala Tyr Ala Thr Ser Ser Tyr Leu His Asp Ser Thr Pro
225                 230                 235                 240

Ser Trp Thr Leu Ser Pro Phe Gln Asp Ala Ala Ser Ser Ser Ser Ser
            245                 250                 255

Ser Ser Ser Ser Ala Thr Thr Thr Pro Glu Thr Ser Thr Ser Pro
        260                 265                 270

Lys Phe His Thr Thr Thr Tyr Ser Thr Glu Arg Ser Glu His Phe Lys
            275                 280                 285

Pro Cys Arg Asp Lys Asp Leu Ala Tyr Cys Leu Asn Asp Gly Glu Cys
        290                 295                 300

Phe Val Ile Glu Thr Leu Thr Gly Ser His Lys His Cys Arg Cys Lys
305                 310                 315                 320

Glu Gly Tyr Gln Gly Val Arg Cys Asp Gln Phe Leu Pro Lys Thr Asp
            325                 330                 335

Ser Ile Leu Ser Asp Pro Thr Asp His Leu Gly Ile Glu Phe Met Glu
            340                 345                 350

Ser Glu Glu Val Tyr Gln Arg Gln Val Leu Ser Ile Ser Cys Ile Ile
            355                 360                 365

Phe Gly Ile Val Ile Val Gly Met Phe Cys Ala Ala Phe Tyr Phe Lys
            370                 375                 380

Ser Lys Lys Gln Ala Lys Gln Ile Gln Glu Gln Leu Lys Val Pro Gln
385                 390                 395                 400

Asn Gly Lys Ser Tyr Ser Leu Lys Ala Ser Ser Thr Met Ala Lys Ser
            405                 410                 415

Glu Asn Leu Val Lys Ser His Val Gln Leu Gln Asn Tyr Ser Lys Val
            420                 425                 430

Glu Arg His Pro Val Thr Ala Leu Glu Lys Met Met Glu Ser Ser Phe
            435                 440                 445

Val Gly Pro Gln Ser Phe Pro Glu Val Pro Ser Pro Asp Arg Gly Ser
            450                 455                 460

Gln Ser Val Lys His His Arg Ser Leu Ser Ser Cys Cys Ser Pro Gly
465                 470                 475                 480

Gln Arg Ser Gly Met Leu His Arg Asn Ala Phe Arg Arg Thr Pro Pro
            485                 490                 495

Ser Pro Arg Ser Arg Leu Gly Gly Ile Val Gly Pro Ala Tyr Gln Gln
            500                 505                 510

Leu Glu Glu Ser Arg Ile Pro Asp Gln Asp Thr Ile Pro Cys Gln Gly
            515                 520                 525

Tyr Ser Ser Ser Gly Leu Lys Thr Gln Arg Asn Thr Ser Ile Asn Met
            530                 535                 540

Gln Leu Pro Ser Arg Glu Thr Asn Pro Tyr Phe Asn Ser Leu Glu Gln
545                 550                 555                 560
```

-continued

```
Lys Asp Leu Val Gly Tyr Ser Ser Thr Arg Ala Ser Ser Val Pro Ile
                565                 570                 575

Ile Pro Ser Val Gly Leu Glu Glu Thr Cys Leu Gln Met Pro Gly Ile
            580                 585                 590

Ser Glu Val Lys Ser Ile Lys Trp Cys Lys Asn Ser Tyr Ser Ala Asp
        595                 600                 605

Val Val Asn Val Ser Ile Pro Val Ser Asp Cys Leu Ile Ala Glu Gln
    610                 615                 620

Gln Glu Val Lys Ile Leu Leu Glu Thr Val Gln Glu Gln Ile Arg Ile
625                 630                 635                 640

Leu Thr Asp Ala Arg Arg Ser Glu Asp Tyr Glu Leu Ala Ser Val Glu
                645                 650                 655

Thr Glu Asp Ser Ala Ser Glu Asn Thr Ala Phe Leu Pro Leu Ser Pro
            660                 665                 670

Thr Ala Lys Ser Glu Arg Glu Ala Gln Phe Val Leu Arg Asn Glu Ile
        675                 680                 685

Gln Arg Asp Ser Ala Leu Thr Lys
    690                 695

<210> SEQ ID NO 24
<211> LENGTH: 695
<212> TYPE: PRT
<213> ORGANISM: Homo sapiens

<400> SEQUENCE: 24

Met Ser Glu Gly Ala Ala Ala Ser Pro Pro Gly Ala Ala Ser Ala
1               5                   10                  15

Ala Ala Ala Ser Ala Glu Glu Gly Thr Ala Ala Ala Ala Ala Ala
                20                  25                  30

Ala Ala Gly Gly Gly Pro Asp Gly Gly Glu Gly Ala Ala Glu Pro
            35                  40                  45

Pro Arg Glu Leu Arg Cys Ser Asp Cys Ile Val Trp Asn Arg Gln Gln
    50                  55                  60

Thr Trp Leu Cys Val Val Pro Leu Phe Ile Gly Phe Ile Gly Leu Gly
65                  70                  75                  80

Leu Ser Leu Met Leu Leu Lys Trp Ile Val Val Gly Ser Val Lys Glu
                85                  90                  95

Tyr Val Pro Thr Asp Leu Val Asp Ser Lys Gly Met Gly Gln Asp Pro
            100                 105                 110

Phe Phe Leu Ser Lys Pro Ser Ser Phe Pro Lys Ala Met Glu Thr Thr
        115                 120                 125

Thr Thr Thr Thr Ser Thr Thr Ser Pro Ala Thr Pro Ser Ala Gly Gly
    130                 135                 140

Ala Ala Ser Ser Arg Thr Pro Asn Arg Ile Ser Thr Arg Leu Thr Thr
145                 150                 155                 160

Ile Thr Arg Ala Pro Thr Arg Phe Pro Gly His Arg Val Pro Ile Arg
                165                 170                 175

Ala Ser Pro Arg Ser Thr Thr Ala Arg Asn Thr Ala Ala Pro Ala Thr
            180                 185                 190

Val Pro Ser Thr Thr Ala Pro Phe Phe Ser Ser Ser Thr Leu Gly Ser
        195                 200                 205

Arg Pro Pro Val Pro Gly Thr Pro Ser Thr Gln Ala Met Pro Ser Trp
    210                 215                 220

Pro Thr Ala Ala Tyr Ala Thr Ser Ser Tyr Leu His Asp Ser Thr Pro
225                 230                 235                 240
```

```
Ser Trp Thr Leu Ser Pro Phe Gln Asp Ala Ser Ser Ser Ser
            245                 250                 255

Ser Ser Ser Ser Ala Thr Thr Thr Pro Glu Thr Ser Thr Ser Pro
            260                 265                 270

Lys Phe His Thr Thr Thr Tyr Ser Thr Glu Arg Ser Glu His Phe Lys
            275                 280                 285

Pro Cys Arg Asp Lys Asp Leu Ala Tyr Cys Leu Asn Asp Gly Glu Cys
290                 295                 300

Phe Val Ile Glu Thr Leu Thr Gly Ser His Lys His Cys Arg Cys Lys
305                 310                 315                 320

Glu Gly Tyr Gln Gly Val Arg Cys Asp Gln Phe Leu Pro Lys Thr Asp
            325                 330                 335

Ser Ile Leu Ser Asp Pro Asn His Leu Gly Ile Glu Phe Met Glu Ser
            340                 345                 350

Glu Glu Val Tyr Gln Arg Gln Val Leu Ser Ile Ser Cys Ile Ile Phe
            355                 360                 365

Gly Ile Val Ile Val Gly Met Phe Cys Ala Ala Phe Tyr Phe Lys Ser
            370                 375                 380

Lys Lys Gln Ala Lys Gln Ile Gln Glu Gln Leu Lys Val Pro Gln Asn
385                 390                 395                 400

Gly Lys Ser Tyr Ser Leu Lys Ala Ser Ser Thr Met Ala Lys Ser Glu
            405                 410                 415

Asn Leu Val Lys Ser His Val Gln Leu Gln Asn Tyr Ser Lys Val Glu
            420                 425                 430

Arg His Pro Val Thr Ala Leu Glu Lys Met Met Glu Ser Ser Phe Val
            435                 440                 445

Gly Pro Gln Ser Phe Pro Glu Val Pro Ser Pro Asp Arg Gly Ser Gln
450                 455                 460

Ser Val Lys His His Arg Ser Leu Ser Ser Cys Cys Ser Pro Gly Gln
465                 470                 475                 480

Arg Ser Gly Met Leu His Arg Asn Ala Phe Arg Arg Thr Pro Pro Ser
            485                 490                 495

Pro Arg Ser Arg Leu Gly Gly Ile Val Gly Pro Ala Tyr Gln Gln Leu
            500                 505                 510

Glu Glu Ser Arg Ile Pro Asp Gln Asp Thr Ile Pro Cys Gln Gly Tyr
            515                 520                 525

Ser Ser Ser Gly Leu Lys Thr Gln Arg Asn Thr Ser Ile Asn Met Gln
530                 535                 540

Leu Pro Ser Arg Glu Thr Asn Pro Tyr Phe Asn Ser Leu Glu Gln Lys
545                 550                 555                 560

Asp Leu Val Gly Tyr Ser Ser Thr Arg Ala Ser Ser Val Pro Ile Ile
            565                 570                 575

Pro Ser Val Gly Leu Glu Glu Thr Cys Leu Gln Met Pro Gly Ile Ser
            580                 585                 590

Glu Val Lys Ser Ile Lys Trp Cys Lys Asn Ser Tyr Ser Ala Asp Val
            595                 600                 605

Val Asn Val Ser Ile Pro Val Ser Asp Cys Leu Ile Ala Glu Gln Gln
            610                 615                 620

Glu Val Lys Ile Leu Leu Glu Thr Val Gln Glu Gln Ile Arg Ile Leu
625                 630                 635                 640

Thr Asp Ala Arg Arg Ser Glu Asp Tyr Glu Leu Ala Ser Val Glu Thr
            645                 650                 655
```

```
Glu Asp Ser Ala Ser Glu Asn Thr Ala Phe Leu Pro Leu Ser Pro Thr
            660                 665                 670

Ala Lys Ser Glu Arg Glu Ala Gln Phe Val Leu Arg Asn Glu Ile Gln
            675                 680                 685

Arg Asp Ser Ala Leu Thr Lys
            690                 695

<210> SEQ ID NO 25
<211> LENGTH: 499
<212> TYPE: PRT
<213> ORGANISM: Homo sapiens

<400> SEQUENCE: 25

Met Glu Cys Gly Ile Pro Pro Thr Leu Val Cys Val Arg Gly Gly Gly
 1               5                  10                  15

Gly Leu His Thr Ile Asn Ile Ile Trp Tyr Tyr Phe Pro Ser Ala
                20                  25                  30

Trp Arg Thr Cys Phe Asn Ile Ser Ser Val Gly Leu Leu Leu Thr
                35                  40                  45

Asn Ser Tyr Lys Phe Tyr Thr Thr Tyr Ser Thr Glu Arg Ser Glu
 50                  55                  60

His Phe Lys Pro Cys Arg Asp Lys Asp Leu Ala Tyr Cys Leu Asn Asp
 65                  70                  75                  80

Gly Glu Cys Phe Val Ile Glu Thr Leu Thr Gly Ser His Lys His Cys
                85                  90                  95

Arg Cys Lys Glu Gly Tyr Gln Gly Val Arg Cys Asp Gln Phe Leu Pro
                100                 105                 110

Lys Thr Asp Ser Ile Leu Ser Asp Pro Thr Asp His Leu Gly Ile Glu
                115                 120                 125

Phe Met Glu Ser Glu Glu Val Tyr Gln Arg Gln Val Leu Ser Ile Ser
            130                 135                 140

Cys Ile Ile Phe Gly Ile Val Ile Val Gly Met Phe Cys Ala Ala Phe
145                 150                 155                 160

Tyr Phe Lys Ser Lys Lys Gln Ala Lys Gln Ile Gln Glu Gln Leu Lys
                165                 170                 175

Val Pro Gln Asn Gly Lys Ser Tyr Ser Leu Lys Ala Ser Ser Thr Met
                180                 185                 190

Ala Lys Ser Glu Asn Leu Val Lys Ser His Val Gln Leu Gln Asn Tyr
            195                 200                 205

Ser Lys Val Glu Arg His Pro Val Thr Ala Leu Glu Lys Met Met Glu
210                 215                 220

Ser Ser Phe Val Gly Pro Gln Ser Phe Pro Glu Val Pro Ser Pro Asp
225                 230                 235                 240

Arg Gly Ser Gln Ser Val Lys His His Arg Ser Leu Ser Ser Cys Cys
                245                 250                 255

Ser Pro Gly Gln Arg Ser Gly Met Leu His Arg Asn Ala Phe Arg Arg
                260                 265                 270

Thr Pro Pro Ser Pro Arg Ser Arg Leu Gly Gly Ile Val Gly Pro Ala
            275                 280                 285

Tyr Gln Gln Leu Glu Glu Ser Arg Ile Pro Asp Gln Asp Thr Ile Pro
            290                 295                 300

Cys Gln Gly Ile Glu Val Arg Lys Thr Ile Ser His Leu Pro Ile Gln
305                 310                 315                 320

Leu Trp Cys Val Glu Arg Pro Leu Asp Leu Lys Tyr Ser Ser Gly
                325                 330                 335
```

```
Leu Lys Thr Gln Arg Asn Thr Ser Ile Asn Met Gln Leu Pro Ser Arg
            340                 345                 350

Glu Thr Asn Pro Tyr Phe Asn Ser Leu Glu Gln Lys Asp Leu Val Gly
        355                 360                 365

Tyr Ser Ser Thr Arg Ala Ser Ser Val Pro Ile Ile Pro Ser Val Gly
    370                 375                 380

Leu Glu Glu Thr Cys Leu Gln Met Pro Gly Ile Ser Glu Val Lys Ser
385                 390                 395                 400

Ile Lys Trp Cys Lys Asn Ser Tyr Ser Ala Asp Val Val Asn Val Ser
                405                 410                 415

Ile Pro Val Ser Asp Cys Leu Ile Ala Glu Gln Gln Glu Val Lys Ile
                420                 425                 430

Leu Leu Glu Thr Val Gln Glu Gln Ile Arg Ile Leu Thr Asp Ala Arg
            435                 440                 445

Arg Ser Glu Asp Tyr Glu Leu Ala Ser Val Glu Thr Glu Asp Ser Ala
        450                 455                 460

Ser Glu Asn Thr Ala Phe Leu Pro Leu Ser Pro Thr Ala Lys Ser Glu
465                 470                 475                 480

Arg Glu Ala Gln Phe Val Leu Arg Asn Glu Ile Gln Arg Asp Ser Ala
                485                 490                 495

Leu Thr Lys

<210> SEQ ID NO 26
<211> LENGTH: 115
<212> TYPE: PRT
<213> ORGANISM: Homo sapiens

<400> SEQUENCE: 26

Met Pro Thr Asp His Glu Glu Pro Cys Gly Pro Ser His Lys Ser Phe
1               5                   10                  15

Cys Leu Asn Gly Gly Leu Cys Tyr Val Ile Pro Thr Ile Pro Ser Pro
            20                  25                  30

Phe Cys Arg Cys Val Glu Asn Tyr Thr Gly Ala Arg Cys Glu Glu Val
        35                  40                  45

Phe Leu Pro Gly Ser Ser Ile Gln Thr Lys Ser Asn Leu Phe Glu Ala
    50                  55                  60

Phe Val Ala Leu Ala Val Leu Val Thr Leu Ile Ile Gly Ala Phe Tyr
65                  70                  75                  80

Phe Leu Cys Arg Lys Gly His Phe Gln Arg Ala Ser Ser Val Gln Tyr
                85                  90                  95

Asp Ile Asn Leu Val Glu Thr Ser Ser Thr Ser Ala His His Ser His
                100                 105                 110

Glu Gln His
        115

<210> SEQ ID NO 27
<211> LENGTH: 65
<212> TYPE: PRT
<213> ORGANISM: Artificial Sequence
<220> FEATURE:
<223> OTHER INFORMATION: Recombinant human neuregulin 1beta

<400> SEQUENCE: 27

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
```

```
                    20                  25                  30
Leu Cys Lys Cys Pro Asn Glu Phe Thr Gly Asp Arg Cys Gln Asn Tyr
                35                  40                  45
Val Met Ala Ser Phe Tyr Lys His Leu Gly Ile Glu Phe Met Glu Ala
            50                  55                  60
Glu
65

<210> SEQ ID NO 28
<211> LENGTH: 210
<212> TYPE: PRT
<213> ORGANISM: Artificial Sequence
<220> FEATURE:
<223> OTHER INFORMATION: Furin domain fragment 1

<400> SEQUENCE: 28

Met Arg Leu Gly Leu Cys Val Val Ala Leu Val Leu Ser Trp Thr His
1               5                   10                  15
Leu Thr Ile Ser Ser Arg Gly Ile Lys Gly Lys Arg Gln Arg Arg Ile
                20                  25                  30
Ser Ala Glu Gly Ser Gln Ala Cys Ala Lys Gly Cys Glu Leu Cys Ser
                35                  40                  45
Glu Val Asn Gly Cys Leu Lys Cys Ser Pro Lys Leu Phe Ile Leu Leu
            50                  55                  60
Glu Arg Asn Asp Ile Arg Gln Val Gly Val Cys Leu Pro Ser Cys Pro
65                  70                  75                  80
Pro Gly Tyr Phe Asp Ala Arg Asn Pro Asp Met Asn Lys Cys Ile Lys
                85                  90                  95
Cys Lys Ile Glu His Cys Glu Ala Cys Phe Ser His Asn Phe Cys Thr
                100                 105                 110
Lys Cys Lys Glu Gly Leu Tyr Leu His Lys Gly Arg Cys Tyr Pro Ala
            115                 120                 125
Cys Pro Glu Gly Ser Ser Ala Ala Asn Gly Thr Met Glu Cys Ser Ser
        130                 135                 140
Pro Ala Gln Cys Glu Met Ser Glu Trp Ser Pro Trp Gly Pro Cys Ser
145                 150                 155                 160
Lys Lys Gln Gln Leu Cys Gly Phe Arg Arg Gly Ser Glu Glu Arg Thr
                165                 170                 175
Arg Arg Val Leu His Ala Pro Val Gly Asp His Ala Ala Cys Ser Asp
                180                 185                 190
Thr Lys Glu Thr Arg Arg Cys Thr Val Arg Arg Val Pro Cys Pro Glu
            195                 200                 205
Gly Gln
    210

<210> SEQ ID NO 29
<211> LENGTH: 146
<212> TYPE: PRT
<213> ORGANISM: Artificial Sequence
<220> FEATURE:
<223> OTHER INFORMATION: Furin domain fragment 2

<400> SEQUENCE: 29

Met Arg Leu Gly Leu Cys Val Val Ala Leu Val Leu Ser Trp Thr His
1               5                   10                  15
Leu Thr Ile Ser Ser Arg Gly Ile Lys Gly Lys Arg Gln Arg Arg Ile
                20                  25                  30
```

```
Ser Ala Glu Gly Ser Gln Ala Cys Ala Lys Gly Cys Glu Leu Cys Ser
        35                  40                  45

Glu Val Asn Gly Cys Leu Lys Cys Ser Pro Lys Leu Phe Ile Leu Leu
    50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
        115                 120                 125

Cys Pro Glu Gly Ser Ser Ala Ala Asn Gly Thr Met Glu Cys Ser Ser
    130                 135                 140

Pro Ala
145

<210> SEQ ID NO 30
<211> LENGTH: 118
<212> TYPE: PRT
<213> ORGANISM: Artificial Sequence
<220> FEATURE:
<223> OTHER INFORMATION: Furin domain fragment 3

<400> SEQUENCE: 30

Gly Gly Ser Gly Gly Ser Ile Ser Ala Glu Gly Ser Gln Ala Cys Ala
1               5                   10                  15

Lys Gly Cys Glu Leu Cys Ser Glu Val Asn Gly Cys Leu Lys Cys Ser
            20                  25                  30

Pro Lys Leu Phe Ile Leu Leu Glu Arg Asn Asp Ile Arg Gln Val Gly
        35                  40                  45

Val Cys Leu Pro Ser Cys Pro Pro Gly Tyr Phe Ala Arg Asn Pro Asp
    50                  55                  60

Met Asn Lys Cys Ile Lys Cys Lys Ile Glu His Cys Glu Ala Cys Phe
65                  70                  75                  80

Ser His Asn Phe Cys Thr Lys Cys Lys Glu Gly Leu Tyr Leu His Lys
                85                  90                  95

Gly Arg Cys Tyr Pro Ala Cys Pro Glu Gly Ser Ser Ala Ala Asn Gly
            100                 105                 110

Thr Met Glu Cys Ser Ser
        115

<210> SEQ ID NO 31
<211> LENGTH: 100
<212> TYPE: PRT
<213> ORGANISM: Artificial Sequence
<220> FEATURE:
<223> OTHER INFORMATION: Furin domain fragment 4

<400> SEQUENCE: 31

Ala Glu Gly Ser Gln Ala Cys Ala Lys Gly Cys Glu Leu Cys Ser Glu
1               5                   10                  15

Val Asn Gly Cys Leu Lys Cys Ser Pro Lys Leu Phe Ile Leu Leu Glu
            20                  25                  30

Arg Asn Asp Ile Arg Gln Val Gly Val Cys Leu Pro Ser Cys Pro Pro
        35                  40                  45

Gly Tyr Phe Ala Arg Asn Pro Asp Met Asn Lys Cys Ile Lys Cys Lys
    50                  55                  60
```

```
Ile Glu His Cys Glu Ala Cys Phe Ser His Asn Phe Cys Thr Lys Cys
 65                  70                  75                  80

Lys Glu Gly Leu Tyr Leu His Lys Gly Arg Cys Tyr Pro Ala Cys Pro
                 85                  90                  95

Glu Gly Ser Ser
            100

<210> SEQ ID NO 32
<211> LENGTH: 105
<212> TYPE: PRT
<213> ORGANISM: Artificial Sequence
<220> FEATURE:
<223> OTHER INFORMATION: VL antibody
<220> FEATURE:
<221> NAME/KEY: Xaa
<222> LOCATION: 4
<223> OTHER INFORMATION: Xaa can be any amino acid

<400> SEQUENCE: 32

Met Thr Gln Xaa Pro Thr Ser Met Ser Ile Ser Ile Gly Asp Arg Val
  1               5                  10                  15

Thr Met Asn Cys Lys Ala Ser Gln Asn Val Asp Ser Asn Val Asp Trp
                 20                  25                  30

Tyr Gln Gln Lys Thr Gly Gln Ser Pro Lys Leu Leu Ile Tyr Lys Ala
             35                  40                  45

Ser Asn Arg Tyr Thr Gly Val Pro Asp Arg Phe Thr Gly Ser Gly Ser
 50                  55                  60

Gly Thr Asp Phe Thr Phe Thr Ile Ser Asn Met Gln Ala Glu Asp Leu
 65                  70                  75                  80

Ala Val Tyr Tyr Cys Met Gln Ser Asn Ser Tyr Pro Leu Thr Phe Gly
                 85                  90                  95

Ser Gly Thr Lys Leu Glu Ile Lys Arg
            100                 105

<210> SEQ ID NO 33
<211> LENGTH: 118
<212> TYPE: PRT
<213> ORGANISM: Artificial Sequence
<220> FEATURE:
<223> OTHER INFORMATION: VH antibody

<400> SEQUENCE: 33

Glu Val Lys Leu Gln Glu Ser Gly Ala Ala Leu Val Lys Pro Gly Ala
  1               5                  10                  15

Ser Val Lys Leu Ser Cys Lys Ala Ser Gly Tyr Thr Phe Thr Asp Tyr
                 20                  25                  30

Tyr Ile His Trp Val Lys Gln Ser His Gly Lys Ser Leu Glu Trp Ile
             35                  40                  45

Gly Tyr Ile Asn Pro Asn Ser Gly Tyr Thr Tyr Asn Glu Lys Phe
 50                  55                  60

Lys Ser Lys Ala Thr Leu Thr Val Asp Lys Ser Thr Asn Thr Ala Tyr
 65                  70                  75                  80

Met Glu Leu Ser Arg Leu Thr Ser Glu Asp Ser Ala Thr Tyr Tyr Cys
                 85                  90                  95

Thr Arg Phe Gly Ser Tyr Trp Tyr Phe Asp Phe Trp Gly Gln Gly Thr
            100                 105                 110

Thr Val Thr Val Ser Ser
            115
```